(12) United States Patent
Son et al.

(10) Patent No.: US 12,203,108 B2
(45) Date of Patent: Jan. 21, 2025

(54) PSICOSE-6-PHOSPHATE PHOSPHATASE, COMPOSITION FOR PRODUCING PSICOSE INCLUDING SAID ENZYME, METHOD FOR PRODUCING PSICOSE USING SAID ENZYME

(71) Applicant: CJ CHEILJEDANG CORPORATION, Seoul (KR)

(72) Inventors: Byung-Sam Son, Ansan-Si (KR); Hyun Kug Cho, Suwon-Si (KR); Sung Jae Yang, Suwon-Si (KR); Seong Bo Kim, Seongnam-Si (KR); Seung Hwan Kim, Seoul (KR); Hyun June Park, Suwon-Si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 362 days.

(21) Appl. No.: 16/635,474

(22) PCT Filed: Jul. 25, 2018

(86) PCT No.: PCT/KR2018/008396
§ 371 (c)(1),
(2) Date: Jan. 30, 2020

(87) PCT Pub. No.: WO2019/027173
PCT Pub. Date: Feb. 7, 2019

(65) Prior Publication Data
US 2021/0355461 A1    Nov. 18, 2021

(30) Foreign Application Priority Data
Jul. 31, 2017 (KR) .................. 10-2017-0097334

(51) Int. Cl.
| | |
|---|---|
| *C12N 9/16* | (2006.01) |
| *C12N 9/10* | (2006.01) |
| *C12N 9/12* | (2006.01) |
| *C12N 9/26* | (2006.01) |
| *C12N 9/34* | (2006.01) |
| *C12N 9/44* | (2006.01) |
| *C12N 9/90* | (2006.01) |
| *C12P 19/02* | (2006.01) |

(52) U.S. Cl.
CPC ............. *C12N 9/16* (2013.01); *C12N 9/1051* (2013.01); *C12N 9/1205* (2013.01); *C12N 9/2414* (2013.01); *C12N 9/2428* (2013.01); *C12N 9/2457* (2013.01); *C12N 9/246* (2013.01); *C12N 9/90* (2013.01); *C12P 19/02* (2013.01); *C12Y 204/01001* (2013.01); *C12Y 204/01007* (2013.01); *C12Y 207/01002* (2013.01); *C12Y 301/03025* (2013.01); *C12Y 501/03* (2013.01); *C12Y 503/01009* (2013.01); *C12Y 504/02002* (2013.01)

(58) Field of Classification Search
CPC .... C12Y 504/02002; C12Y 503/01009; C12Y 501/03; C12Y 301/03025; C12Y 207/01002; C12Y 204/01007; C12Y 204/01001; C12P 19/02; C12N 9/90; C12N 9/246; C12N 9/2457; C12N 9/2428; C12N 9/2414; C12N 9/1205; C12N 9/1051; C12N 9/16
See application file for complete search history.

(56) References Cited

U.S. PATENT DOCUMENTS

| | | |
|---|---|---|
| 5,411,880 A | 5/1995 | Izumori et al. |
| 5,679,562 A | 10/1997 | Izumori et al. |
| 8,178,704 B2 | 5/2012 | Bazin et al. |
| 8,735,106 B2 | 5/2014 | Hong et al. |
| 9,505,795 B2 | 11/2016 | Konishi et al. |
| 9,701,953 B2 | 7/2017 | Han et al. |
| 9,951,361 B2 | 4/2018 | Ahn et al. |
| 9,988,618 B2 | 6/2018 | Kim et al. |
| 11,053,528 B2 * | 7/2021 | Wichelecki ............. C12P 19/02 |
| 2008/0261237 A1 | 10/2008 | Bazin et al. |
| 2012/0244580 A1 | 9/2012 | Hung et al. |
| 2014/0370549 A1 | 12/2014 | Konishi et al. |
| 2015/0110940 A1 | 4/2015 | Lee et al. |
| 2016/0304853 A1 | 10/2016 | Han et al. |
| 2017/0101637 A1 | 4/2017 | Kim et al. |
| 2017/0211109 A1 | 7/2017 | Ahn et al. |

FOREIGN PATENT DOCUMENTS

| | | |
|---|---|---|
| EP | 3 135 762 A1 | 3/2017 |
| JP | H06-125776 A | 5/1994 |
| JP | 2008-521867 A | 6/2008 |
| JP | 2013-501519 A | 1/2013 |
| KR | 10-2014-0021974 A | 2/2014 |

(Continued)

OTHER PUBLICATIONS

NCBI Blast results, NCBI, [retrieved on Dec. 8, 2021] retrieved from the internet <URL: https://www.ncbi.nlm.nih.gov/protein/WP_012842901.1?report=genbank&log$=protalign&blast_rank=1&RID=V222EHMX013>.*

(Continued)

*Primary Examiner* — Robert J Yamasaki
*Assistant Examiner* — Trevor Kane
(74) *Attorney, Agent, or Firm* — Morgan, Lewis & Bockius LLP

(57) ABSTRACT

The present application relates to a psicose-6-phosphate phosphatase comprising motif A and motif B, a composition for producing D-psicose comprising the enzyme, and a method for producing D-psicose using the enzyme.

15 Claims, 6 Drawing Sheets
Specification includes a Sequence Listing.

(56) References Cited

FOREIGN PATENT DOCUMENTS

| KR | 10-2014-0140215 A | 2/2014 |
|---|---|---|
| KR | 10-2014-0123284 A | 10/2014 |
| RU | 2664311 C2 | 8/2018 |
| WO | 2013-115012 A1 | 8/2013 |
| WO | 2015/099256 A1 | 7/2015 |
| WO | 2017/002978 A1 | 1/2017 |

OTHER PUBLICATIONS

Stec, B., Yang, H., Johnson, K. A., Chen, L., & Roberts, M. F. (2000). MJ0109 is an enzyme that is both an inositol monophosphatase and the 'missing' archaeal fructose-1, 6-bisphosphatase. Nature structural biology, 7(11), 1046-1050 (Year: 2000).*
Chin J., Alexander D.H., Marks P., Korlach J., Clum A., Copeland A.; Directly Submitted (Apr. 2013) to the EMBL/GenBank/DDBJ databases (Year: 2013).*
Russian Decision of Grant mailed Aug. 13, 2021 for RU Application No. 2020104267 (10 pages).
Office Action issued in corresponding Taiwanese patent application No. , mailed Mar. 9, 2020.
"D0ME65", UniProtKB, published Dec. 15, 2009. Available Online at: https://www.uniprot.org/uniprot/D0ME65.
"A8F809", UniProtKB, published Nov. 13, 2007. Available Online at: https://www.uniprot.org/uniprot/A8F809.
"AGK03362.1", Ncbi GenBank, published May 5, 2017. Available Online at: https://www.ncbi.nlm.nih.gov/protein/AGK03362.1.
Russian Office Action for corresponding Russian Patent Application No. 2020104267/10(006612) mailed Oct. 15, 2020, 17 pages.
NCBI, GenPept accession No. WP_012583263.1.
NCBI, GenPept accession No. WP_013012427.1.
NCBI, GenPept accession No. WP_012003769.1.
NCBI, GenPept accession No. WP_012842901.1.
NCBI GenBank Accession No. CP005385.1.
Andrew F. Neuwald et al., "Diverse proteins homologous to inositol monophosphatase", Federation of European Biochemical Societies, Dec. 1991, vol. 294, No. 1,2, pp. 16-18.
Kui K. Chan et al., "Structural basis for substrate specificity in phosphate binding (beta/alpha)8-barrels: D-allulose 6-phosphate 3-epimerase from *Escherichia coli* K-12", Biochemistry 2008, vol. 47, No. 36, pp. 9608-9617.

International Search Report from International Application No. PCT/KR2018/008393, mailed Feb. 8, 2019.
Written Opinion from International Application No. PCT/KR2018/008393, mailed Feb. 8, 2019.
Extended European Search Report for European Patent Application No. 18841900.6 issued Mar. 31, 2021, 10 pages.
Japanese Office Action for Japanese Patent Application No. 2020-505148 issued Mar. 23, 2021, 5 pages.
Anonymous, "030298", Jan. 23, 2002. Available online at: URL:www.uniprot.org_uniprot_030298.txt.
Anonymous, "B8E151 (B8E151_DICTD)", UniProtKB. Available online at: https://www.uniprot.org/uniprot/B8E151.
Anonymous, "C8WRN6", Nov. 3, 2009. Available online at: www.uniprot.org_uniprot_C8WRN6.txt.
Anonymous, "D3PL12 (D3PL12_MEIRD)", UniProtKB. Available online at: https://www.uniprot.org/uniprot/D3PL12.
Anonymous, "D7BF71 ", Aug. 10, 2010. Available online at: www.uniprot.org_uniprot_D7BF71.txt.
Anonymous, "E8N218", Apr. 5, 2011. Available online at: www.uniprot.org_uniprot_E8N218.txt.
Anonymous, "G2MXM6", Nov. 16, 2011. Available online at: URL:https://www.uniprot.org/uniprot/G2MXM6.txt.
Anonymous, "G7VES3", Jan. 25, 2012. Available online at: https://www.uniprot.org/uniprot/G7VES3.txt.
Anonymous, "H3ZPX7", Apr. 18, 2012. Available online at: https://www.uniprot.org/uniprot/H3ZPX7.txt.
Anonymous, "L7ZWR5", Apr. 3, 2013. Available online at: www.uniprot.org_uniprot_L7ZWR5.txt.
Anonymous, "M113U1 ", May 1, 2013. Available online at: www.uniprot.org_uniprot_M113U1.txt.
Anonymous, "Q72GCO", Jul. 5, 2004. Available online at: https://www.uniprot.org/uniprot/Q72GCO.txt.
Anonymous, "Q8TZH9", Jun. 1, 2002. Available online at: www.uniprot.org_uniprot_Q8TZH9.txt.
Anonymous, "WP_027883570", Oct. 19, 2015. Available online at: https://www.ncbi.nlm.nih.gov/protein/ WP_027883570.
Anonymous, "WP_068549149", Aug. 26, 2016. Available online at: https://www.ncbi.nlm.nih.gov/protein/WP_068549149.
Mu, Wanmeng et al., "Recent advances on applications and biotechnological production of D-psicose", Applied Microbiology and Biotechnology, 2012, pp. 1461-1467, vol. 94, No. 6.
Nolan, M. et al., Inositol-phosphate phosphatase [Rhodothermus marinus DSM 4252], Genebank ACY47289.1, Dec. 11, 2013.

* cited by examiner

PSICOSE-6-PHOSPHATE PHOSPHATASE, COMPOSITION FOR PRODUCING PSICOSE INCLUDING SAID ENZYME, METHOD FOR PRODUCING PSICOSE USING SAID ENZYME

This application is a National Stage Application of International Application No. PCT/KR2018/008396, filed Jul. 25, 2018, which claims benefit of Serial No. 10-2017-0097334, filed Jul. 31, 2017 in Korea and which applications are incorporated herein by reference. To the extent appropriate, a claim of priority is made to each of the above disclosed applications.

TECHNICAL FIELD

The present application relates to a novel psicose-6-phosphate phosphatase, a composition for producing D-psicose including the enzyme, and methods for producing D-psicose using the enzyme.

BACKGROUND ART

D-psicose-3-epimerase (EC 5.1.3.30) and D-tagatose-3-epimerase (EC 5.1.3.31) are known as enzymes that catalyze the 3-epimerization of D-fructose to produce D-psicose. When D-psicose is produced through a single enzymatic reaction using the enzyme, reaction equilibrium between the substrate (i.e. D-fructose) and the product (i.e. D-psicose) exists at a constant level (product/substrate=−20-35%). Thus, the production of high-purity D-psicose requires an additional process for separating and removing a relatively high concentration of D-fructose from the enzymatic reaction product.

On the other hand, Chan et al. (2008. Biochemistry. 47:9608-9617) reported D-ribulose-5-phosphate-3-epimerase (EC 5.1.3.1) derived from *Streptococcus pyogenes* and D-psicose 6-phosphate-3-epimerase (EC 5.1.3.-) derived from *E. coli* capable of catalyzing the 3-epimerization of D-fructose-6-phosphate and D-psicose-6-phosphate. However, these enzymes are not industrially applicable due to their poor thermoresistance.

Under such circumstances, the present inventors have earnestly conducted research to develop a method for increasing the conversion rate of D-psicose on an industrial scale in an economical manner. As a result, the present inventors have found that, after sucrose or starch (e.g., maltodextrin) as an inexpensive raw material is converted to D-psicose-6-phosphate, the use of a psicose-6-phosphate phosphatase specific to the D-psicose-6-phosphate and participating in the irreversible reaction pathway enables the production of D-psicose through one-pot enzymatic conversions with two or more enzymes involved in the D-psicose production pathways and can significantly increase the conversion rate to D-psicose. The present application has been accomplished based on this finding.

DISCLOSURE

Technical Problem

It is one object of the present application to provide a novel psicose-6-phosphate phosphatase comprising motif A and motif B.

It is another object of the present application to provide a nucleic acid encoding the psicose-6-phosphate phosphatase described herein and a transformant comprising the nucleic acid.

It is a further object of the present application to provide a composition for producing D-psicose comprising an inositol-mono-phosphatase, a microorganism expressing the inositol-mono-phosphatase or a culture of the microorganism.

It is yet another object of the present application to provide a method for producing D-psicose comprising contacting an inositol-mono-phosphatase, a microorganism expressing the inositol-mono-phosphatase or a culture of the microorganism with D-psicose-6-phosphate to convert the D-psicose-6-phosphate to D-psicose.

Technical Solution

The present application will now be described in detail. Meanwhile, the explanations of aspects and embodiments disclosed in the present application may also be applied to explanations of other aspects and embodiments. In addition, all combinations of various elements disclosed in the present application fall within the scope of the present application. Furthermore, it is not considered that the scope of the present application is limited by the following detailed description.

In order to achieve the above and other objects of the present application, one aspect of the present application provides a psicose-6-phosphate phosphatase comprising motif A represented by $X_{a1}$-$X_{a2}$-$X_{a3}$-DPLDG-$X_{a4}$ wherein $X_{a1}$ is W, F, V, I or A, $X_{a2}$ is I, F, V, A or a gap, $X_{a3}$ is V, I or L, and $X_{a4}$ is T or S and motif B represented by $Y_{a1}$-D-$Y_{a2}$-$W_{a1}$-$Y_{a3}$-$W_{a2}$-$Y_{a4}$-$W_{a3}$ wherein $Y_{a1}$ is W, Y, T, L or V, $Y_{a2}$ is V, I, C, F or A, $W_{a1}$ is AAG, AAS, SAG, APG, APF, AGG, APL or AGA, $Y_{a3}$ is W, I, P, M, V, Y, F, R, L, T or S, $W_{a2}$ is LLV, LIV, LLI, LII, ILI, FIA, ALV, IIA, VLV, VIL, TIG, NFC or PIF, $Y_{a4}$ is E, R, S, T, L, K or P, and $W_{a3}$ is EAGG, EGGG, EAKG, KAGG, AAGG, YVDG, EAGA or RLGV.

Specifically, in motif A, $X_{a1}$ may be W or F, $X_{a2}$ may be I or V, $X_{a3}$ may be V or I, and $X_{a4}$ may be T. Specifically, in motif B, $Y_{a1}$ may be W, $Y_{a2}$ may be V or I, $W_{a1}$ may be AAG, $Y_{a3}$ may be W, I or V, $W_{a2}$ may be LLV, LIV, LII or LLI, $Y_{a4}$ may be E, R or S, and $W_{a3}$ may be EAGG or EGGG.

One or more amino acids may be present between motif A and motif B, at one end of motif A or at one end of motif B. The amino acid sequences other than motif A and motif B may be defined from the sequences of known inositol-mono-phosphatases (for example, the sequences other than motif A and motif B in the sequences set forth in SEQ ID NOS: 1 to 20).

Motif A and/or motif B is an active site in the sequence of the inositol-mono-phosphatase. Motif A and/or motif B is also known as a binding site of inositol phosphate as a substrate of the enzyme (=Federation of European Biochemical Societies, Volume 294, number 1, 2, 16-18, December 1991). The present inventors have found that the inositol-mono-phosphatase exhibits a psicose-6-phosphate phosphatase activity. The present inventors have also found that motif A and/or motif B of the inositol-mono-phosphatase may be a substrate binding site of the phosphatase.

The psicose-6-phosphate phosphatase may comprise for example any one of the amino acid sequences set forth in SEQ ID NOS: 1 to 20.

The psicose-6-phosphate phosphatase of the present application may be an enzyme that has the functions of known inositol-mono-phosphatases.

The psicose-6-phosphate phosphatase of the present application more selectively catalyzes the dephosphorylation of D-psicose-6-phosphate and may be non-specific for D-glucose-1-phosphate, D-glucose-6-phosphate or D-fructose-6-phosphate.

The psicose-6-phosphate phosphatase of the present application may be produced by transforming a strain with the enzyme as it is or DNA expressing the enzyme (for example, SEQ ID NOS: 21 to 40), culturing the transformed strain, disrupting the culture, followed by purification. The purification can be performed by column chromatography. The strain may be, for example, *Escherichia coli, Corynebacterium glutamicum, Aspergillus oryzae* or *Bacillus subtilis*.

According to one embodiment of the present application, the psicose-6-phosphate phosphatase of the present application may include an enzyme that has a homology, similarity or identity of at least 90%, at least 95%, at least 97%, at least 99% or 100% to the sequence of motif A and/or motif B and exhibits psicose-6-phosphate phosphatase activity. Alternatively, the psicose-6-phosphate phosphatase of the present application may be an enzyme that has a homology, similarity or identity of at least 70%, at least 75%, at least 80%, at least 85%, at least 90%, at least 95%, at least 97%, at least 99% or 100% to the sequences other than motif A and/or motif B. In one embodiment, the psicose-6-phosphate phosphatase of the present application may include a protein consisting of a sequence that has a homology, similarity or identity of at least 90%, at least 95%, at least 97%, at least 99% or 100% to the sequence of motif A and/or motif B in the sequences set forth in SEQ ID NOS: 1 to 20 and has a homology, similarity or identity of at least 70%, at least 75%, at least 80%, at least 85%, at least 90%, at least 95%, at least 97%, at least 99% or 100% to an amino acid sequence other than motif A and/or motif B in the sequences set forth in SEQ ID NOS: 1 to 20 or a homology, similarity or identity in the range defined by any two of the above values. For example, any amino acid sequence that has the homology, similarity or identity defined above and exhibits an efficacy corresponding to that of the psicose-6-phosphate phosphatase protein, for example, a protein consisting of any one of the sequences set forth in SEQ ID NOS: 1 to 20, and is partially deleted, modified, substituted or added is also within the scope of the present application.

Proteins in which irrelevant sequences are added upstream and downstream of the sequences of motif A and motif B are within the scope of the present application and naturally occurring mutations or silent mutations thereof are not excluded from the scope of the present application as long as they have an activity corresponding to that of the psicose-6-phosphate phosphatase comprising motif A and motif B. Particularly, proteins in which irrelevant sequences are added upstream and downstream of any one of the amino acid sequences set forth in SEQ ID NOS: 1 to 20, naturally occurring mutations, and silent mutations thereof are not excluded from the scope of the present application as long as they have an activity corresponding to that of the psicose-6-phosphate phosphatase comprising motif A and motif B. Proteins comprising motif A and motif B or proteins comprising the amino acid sequences set forth in SEQ ID NOS: 1 to 20 are also within the scope of the present application as long as they have an activity corresponding to that of the psicose-6-phosphate phosphatase comprising motif A and motif B.

Another aspect of the present application provides a nucleic acid encoding the psicose-6-phosphate phosphatase.

As used herein, the term "nucleic acid" encompasses DNA and RNA molecules, and a nucleotide as a basic unit of the nucleic acid includes a natural nucleotide as well as an analogue with a modified sugar or base (see Scheit, Nucleotide Analogs, John Wiley, New York (1980); Uhlman and Peyman, Chemical Reviews, 90:543-584(1990)).

Specifically, the nucleic acid encoding the psicose-6-phosphate phosphatase may include sequences including nucleotides that can be translated into motif A and motif B. In one embodiment, the nucleic acid of the present application may consist of any one of the nucleotide sequences set forth in SEQ ID NOS: 21 to 40. More specifically, the nucleic acid of the present application may include a nucleic acid that has a homology, similarity or identity of at least 90%, at least 95%, at least 99% or 100% to nucleotides that can be translated into motif A and motif B and can exhibit the desired enzyme activity after translation. Specifically, the nucleic acid of the present application may include a nucleic acid that has a homology, similarity or identity of at least 90%, at least 95%, at least 99% or 100% to nucleotides that can be translated into motif A and motif B in the sequences set forth in SEQ ID NOS: 21 to 40. Alternatively, the nucleic acid of the present application may be a nucleic acid that has a homology, similarity or identity of at least 80%, at least 90%, at least 95%, at least 97% or at least 99% to nucleotides that can be translated into motifs other than motif A and motif B in the sequences set forth in SEQ ID NOS: 21 to 40. Proteins that can be translated into proteins including motif A and motif B due to codon degeneracy, specifically, proteins consisting of any one of the amino acid sequences set forth in SEQ ID NOS: 1 to 20 or polynucleotides that can be translated into proteins having a homology, similarity or identity to the proteins consisting of any one of the amino acid sequences set forth in SEQ ID NOS: 1 to 20 are also within the scope of the present application.

The enzyme comprising motif A and motif B according to the present application may be derived from a thermoresistant or thermophilic strain. Specifically, the enzyme consisting of any one of the amino acid sequences set forth in SEQ ID NOS: 1 to 20 may be an enzyme derived from *Rhodothermus marinus, Thermotoga lettingae, Meiothermus ruber, Dictyoglomus turgidum, Pyrobaculum ferrireducens, Thermoanaerobacter wiegelii, Thermus thermophilus, Thermococcus litoralis, Geobacillus stearothermophilus, Anaerolinea thermophila, Sulfolobus acidocaldarius, Thermosulfidibacter takai, Pyrococcus furiosus, Archaeoglobus fulgidus, Alicyclobacillus acidocaldarius, Meiothermus silvanus, Meiothermus rufus, Meiothermus taiwanensis, Meiothermus chliarophilus* or *Meiothermus cerbereus*.

As used herein, the term "homology" or "identity" indicates the degree of relatedness between two given amino acid sequences or nucleotide sequences, which can be expressed as a percentage.

The terms "homology" and "identity" are often used interchangeably.

The sequence homology or identity of conserved polynucleotides or polypeptides is determined by standard alignment algorithms and can be used with default gap penalties established by programs used. Substantially, homologous, or identical sequence would hybridize typically at moderate stringency or at high stringency all along at least about 50%, 60%, 70%, 80% or 90% of the full-length polynucleotide or polypeptide of interest. Also contemplated are polynucleotides that contain degenerate codons in place of codons in the hybridizing polynucleotides.

Whether any two polynucleotide or polypeptide sequences are homologous, similar or identical can be determined using known computer algorithms such as the "FASTA" program, using for example, the default parameters as in Pearson et al. (1988), Proc. Natl. Acad. Sci. USA 85: 2444. Alternatively, the sequence homology, similarity or identity may be determined using the Needleman-Wunsch algorithm (Needleman and Wunsch, 1970, *J. Mol. Biol.* 48, 443453) as implemented in the Needle program of the EMBOSS package (EMBOSS: The European Molecular Biology Open Software Suite, Rice et al., 2000, *Trends Genet.* 16: 276-277), version 5.0.0 or later. Other programs include the GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO et al.] (1988) SIAM J Applied Math 48: 1073). For instance, the BLAST tool of the NCBI database can be used to determine homology, similarity or identity. Other commercially or publicly available programs such as ClustalW may also be used.

Percent homology, similarity or identity of polynucleotides or polypeptides can be determined, for example, by comparing sequence information using a GAP computer program (e g. Needleman et al., (1970) J. Mol. Biol. 48:443, as revised by Smith and Waterman, Adv. Appl. Math (1981) 2:482) Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) Nucl. Acids Res. 14:6745, as described by Schwartz and Dayhoff, eds., Atlas Of Protein Sequence And Structure, National Biomedical Research Foundation, pp. 353-358 (1979); (2) a penalty of 3.0 for each gap and an additional 0.10 penalty for each symbol in each gap (or gap open penalty 10.0, gap extension penalty 0.5); and (3) no penalty for end gaps Therefore, the terms "homology", or "identity" as used herein indicate comparison between polypeptides or polynucleotides.

A further aspect of the present application provides a vector comprising the nucleic acid encoding the psicose-6-phosphate phosphatase described herein or a transformant comprising the nucleic acid encoding the psicose-6-phosphate phosphatase or the vector comprising the nucleic acid encoding the psicose-6-phosphate phosphatase.

As used herein, the term "vector" refers to any vehicle for the cloning and/or transfer of bases nucleic acid into a host cell. A vector may be a replicon to which another DNA segment may be attached so as to bring about the replication of the attached segment. A "replicon" refers to any genetic element (e.g., plasmid, phage, cosmid, chromosome or virus) that functions as an autonomous unit of DNA replication in vivo, i.e. capable of replication under its own control. The term "vector" may include both viral and nonviral vehicles for introducing nucleic acid into a host cell in vitro, ex vivo or in vivo. The term "vector" may also include minicircle DNAs. Specifically, the vector comprising the nucleic acid encoding the psicose-6-phosphate phosphatase according to the present application may be pET21a-CJ_Rma, pET21a-CJ_Tle, pET21a-CJ_Mrub, pET21a-CJ_Dtu, pET21a-CJ_Msi, pET21a-CJ_Mruf, pET21a-CJ_Mta, pET21a-CJ_Mch, pET21a-CJ_Mce, pBT7-C-His-CJ_Pfe, pBT7-C-His-CJ_Twi, pBT7-C-His-CJ_Tth, pBT7-C-His-CJ_Tli, pBT7-C-His-CJ_Gst, pBT7-C-His-CJ_Ath, pBT7-C-His-CJ_Sac, pBT7-C-His-CJ_Tta, pBT7-C-His-CJ_Pfu, pBT7-C-His-CJ_Afu or pBT7-C-His-CJ_Aac.

As used herein, the term "transformation" refers to the introduction of a vector including a nucleic acid encoding a target protein into a host cell to express the protein encoded by the nucleic acid in the host cell. The transformed nucleic acid may be either inserted into and located in the chromosome of the host cell or may exist extrachromosomally as long as it can be expressed in the host cell. The nucleic acid includes DNA and RNA encoding the target protein. The nucleic acid may be introduced in any form as long as it can be introduced into and expressed in the host cell. For example, the nucleic acid may be introduced into the host cell in the form of an expression cassette, which is a gene construct including all elements required for its autonomous expression, but its form is not limited thereto. Typically, the expression cassette includes a promoter operably linked to the nucleic acid, a transcription termination signal, a ribosome-binding domain, and a translation termination signal. The expression cassette may be in the form of a self-replicable expression vector. The nucleic acid as it is may be introduced into the host cell and operably linked to sequence required for expression in the host cell.

As used herein, the term "operably linked" refers to a functional linkage between a promoter sequence initiating and mediating the transcription of the nucleic acid encoding the target protein of the present application and a gene sequence.

The following abbreviations and names are used for the amino acids mentioned in the present application.

TABLE 1

| Type of amino acid | Abbreviation |
|---|---|
| Alanine | A |
| Arginine | R |
| Asparagine | N |
| Aspartic acid | D |
| Cysteine | C |
| Glutamic acid | E |
| Glutamine | Q |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

Any transformation method for introducing the nucleic acid into a cell may be used. The transformation method may be carried out by a suitable standard technique known in the art depending on the type of host cell. Examples of such transformation methods include, but are not limited to, electroporation, calcium phosphate ($CaPO_4$) precipitation, calcium chloride ($CaCl_2$) precipitation, retroviral infection, microinjection, the polyethylene glycol (PEG) method, the DEAE-dextran method, the cationic liposome method, and the lithium acetate-DMSO method.

The host cells are preferably host cells into which DNA is introduced with high efficiency and in which the introduced DNA is expressed at a high level. Examples of the host cells include, but are not limited to, cells of microorganisms belonging to the genera *Corynebacterium*, *Escherichia*, and *Serratia*. Specifically, the host cells may be *E. coli* cells.

The transformant of the present application may be *E. coli* BL21(DE3)/pET21a-CJ_Rma(*E. coli*_P1_CJ_Rma, KCCM12057P), *E. coli* BL21(DE3)/pET21a-CJ_Tle(*E. coli* P2_CJ_Tle, KCCM12058P), *E. coli* BL21(DE3)/pET21a-CJ_Mrub(*E. coli*_P3_CJ_Mrub, KCCM12059P), *E. coli* BL21(DE3)/pET21a-CJ_Dtu(*E. coli*_P4_CJ_Dtu, KCCM12060P), *E. coli* BL21(DE3)/pBT7-C-His-CJ_Pfe (*E. coli*_P5_CJ_Pfe, KCCM12061P), *E. coli* BL21(DE3)/pBT7-C-His-CJ_Twi(*E. coli*_P6_CJ_Twi, KCCM12062P), *E. coli* BL21(DE3)/pBT7-C-His-CJ_Tth(*E. coli* P7_CJ_Tth, KCCM12063P), *E. coli* BL21(DE3)/pBT7-C-His-CJ_Tli(*E. coli*_P8_CJ_Tli, KCCM12064P), *E. coli* BL21(DE3)/pBT7-C-His-CJ_Gst(*E. coli*_P9_CJ_Gst, KCCM12065P), *E. coli* BL21(DE3)/pBT7-C-His-CJ_Ath(*E. coli*_P10_CJ_Ath, KCCM12066P), *E. coli* BL21(DE3)/pBT7-C-His-CJ_Sac (*E. coli*_P11_CJ_Sac, KCCM12067P), *E. coli* BL21(DE3)/pBT7-C-His-CJ_Tta(*E. coli*_P12_CJ_Tta, KCCM12068P), *E. coli* BL21(DE3)/pBT7-C-His-CJ_Pfu(*E. coli*_P13_CJ_Pfu, KCCM12069P), *E. coli* BL21(DE3)/pBT7-C-His-CJ_Afu(*E. coli*_P14_CJ_Afu, KCCM12070P), *E. coli* BL21(DE3)/pBT7-C-His-CJ_Aac (*E. coli*_P15_CJ_Aac, KCCM12071P), *E. coli* BL21(DE3)/pET21a-CJ_Msi(*E. coli*_P16_CJ_Msi, KCCM12072P), *E. coli* BL21(DE3)/pET21a-CJ_Mruf(*E. coli*_P17_CJ_Mruf, KCCM12073P), *E. coli* BL21(DE3)/pET21a-CJ_Mta(*E. coli*_P18_CJ_Mta, KCCM12074P), *E. coli* BL21(DE3)/pET21a-CJ_Mch(*E. coli*_P19_CJ_Mch, KCCM12075P) or *E. coli* BL21(DE3)/pET21a-CJ_Mce(*E. coli*_P20_CJ_Mce, KCCM12076P).

Another aspect of the present application provides a composition for producing D-psicose comprising an inositol-mono-phosphatase, a microorganism expressing the inositol-mono-phosphatase or a culture of the microorganism expressing the inositol-mono-phosphatase.

The inositol-mono-phosphatase of the present application may include motif A represented by $X_{a1}$-$X_{a2}$-$X_{a3}$-DPLDG-$X_{a4}$ wherein $X_{a1}$ is W, F, V, I or A, $X_{a2}$ is I, F, V, A or a gap, $X_{a3}$ is V, I or L, and $X_{a4}$ is T or S and motif B represented by $Y_{a1}$-D-$Y_{a2}$-$W_{a1}$-$Y_{a3}$-$W_{a2}$-$Y_{a4}$-$W_{a3}$ wherein $Y_{a1}$ is W, Y, T, L or V, $Y_{a2}$ is V, I, C, F or A, $W_{a1}$ is AAG, AAS, SAG, APG, APF, AGG, APL or AGA, $Y_{a3}$ is W, I, P, M, V, Y, F, R, L, T or S, $W_{a2}$ is LLV, LIV, LLI, LII, ILI, FIA, ALV, IIA, VLV, VIL, TIG, NFC or PIF, $Y_{a4}$ is E, R, S, T, L, K or P, and $W_{a3}$ is EAGG, EGGG, EAKG, KAGG, AAGG, YVDG, EAGA or RLGV. That is, the inositol-mono-phosphatase can be used interchangeably with the psicose-6-phosphate phosphatase. Thus, the explanations of the psicose-6-phosphate phosphatase can be applied to the inositol-mono-phosphatase. In one embodiment, the inositol-mono-phosphatase may be an enzyme consisting of any one of the amino acid sequences set forth in SEQ ID NOS: 1 to 20.

The composition of the present application may further comprise an enzyme and/or a substrate involved in the D-psicose production pathway (see FIG. 1) [(i) starch, maltodextrin, sucrose or a combination thereof, (ii) a phosphate; (iii) a D-fructose-6-phosphate-3-epimerase; (iv) a D-glucose-6-phosphate-isomerase; (v) a phosphoglucomutase or a glucokinase; and/or (vi) an α-glucan phosphorylase, a starch phosphorylase, a maltodextrin phosphorylase, a sucrose phosphorylase, an α-amylase, a pullulanase, an isoamylase, a glucoamylase or a sucrase]; a microorganism expressing the enzyme involved in the D-psicose production pathway; or a culture of the microorganism expressing the enzyme involved in the D-psicose production pathway. The additional enzyme and substrate are merely illustrative and are not limited as long as D-psicose can be produced using the psicose-6-phosphate phosphatase of the present application.

The starch/maltodextrin phosphorylase (EC 2.4.1.1) and α-glucan phosphorylase may include any protein that is active in phosphoryl transfer to glucose to produce D-glucose-1-phosphate from starch or maltodextrin. Specifically, the protein active in producing D-glucose-1-phosphate from starch or maltodextrin may consist of the amino acid sequence set forth in SEQ ID NO: 59. The protein active in producing D-glucose-1-phosphate from starch or maltodextrin may be encoded by the sequence set forth in SEQ ID NO: 60.

The sucrose phosphorylase (EC 2.4.1.7) may include any protein that is active in phosphoryl transfer to glucose to produce D-glucose-1-phosphate from sucrose.

The α-amylase (EC 3.2.1.1), pullulanase (EC 3.2.1.41), glucoamylase (EC 3.2.1.3), and isoamylase are starch liquefying enzymes and may include any protein that is active in converting starch or maltodextrin to glucose.

The sucrase (EC 3.2.1.26) may include any protein that is active in converting sucrose to glucose.

The phosphoglucomutase (EC 5.4.2.2) may include any protein that is active in converting D-glucose-1-phosphate to D-glucose-6-phosphate. Specifically, the protein active in converting D-glucose-1-phosphate to D-glucose-6-phosphate may comprise the amino acid sequence set forth in SEQ ID NO: 61. The protein active in converting D-glucose-1-phosphate to D-glucose-6-phosphate may be encoded by the sequence set forth in SEQ ID NO: 62.

The glucokinase may include any protein that is active in phosphoryl transfer to glucose to convert glucose to D-glucose-6-phosphate. Specifically, the glucokinase may be a polyphosphate-dependent glucokinase. More specifically, the glucokinase may be a protein consisting of the amino acid sequence set forth in SEQ ID NO: 77 or 78. The D-glucose-6-phosphate-isomerase may include any protein that is active in converting D-glucose-6-phosphate to D-fructose-6-phosphate. Specifically, the D-glucose-6-phosphate-isomerase may be a protein comprising the amino acid sequence set forth in SEQ ID NO: 63. The D-glucose-6-phosphate-isomerase may be encoded by the sequence set forth in SEQ ID NO: 64.

The D-fructose-6-phosphate-3-epimerase may include any protein that is active in converting D-fructose-6-phosphate to D-psicose-6-phosphate. Specifically, the D-fructose-6-phosphate-3-epimerase may be a protein comprising the amino acid sequence set forth in SEQ ID NO: 65. The D-fructose-6-phosphate-3-epimerase may be encoded by the sequence set forth in SEQ ID NO: 66.

The composition for D-psicose production according to the present application may further include a protein that is active in converting glucose to starch, maltodextrin or sucrose. The protein may be, for example, a 4-α-glucanotransferase. The protein active in converting glucose to starch, maltodextrin or sucrose may be an enzyme comprising the amino acid sequence set forth in SEQ ID NO: 67. Specifically, the protein active in converting glucose to starch, maltodextrin or sucrose may be encoded by the nucleotide sequence set forth in SEQ ID NO: 68. The composition for D-psicose production according to the present application may further include any suitable excipient known in the art. Examples of such excipients include, but are not limited to, preservatives, wetting agents, dispersants, suspending agents, buffers, stabilizers, and isotonic agents.

The composition for D-psicose production according to the present application may further include a metal ion or a metal salt. In one embodiment, the metal ion may be a divalent metal cation. Specifically, the metal ion may be selected from the group consisting of Ni, Mg, Co, Mn, Fe, and Zn ions. More specifically, the composition for D-psicose production according to the present application may further include a metal salt. Even more specifically, the metal salt may be selected from the group consisting of $NiSO_4$, $MgSO_4$, $MgCl_2$, $NiCl_2$, $CoSO_4$, $CoCl_2$, $MnCl_2$, $FeSO_4$, $ZnSO_4$, and mixtures thereof.

Another aspect of the present application provides a method for producing D-psicose comprising contacting an inositol-mono-phosphatase, a microorganism expressing the enzyme or a culture of the microorganism with D-psicose-6-phosphate to convert the D-psicose-6-phosphate to D-psicose.

The inositol-mono-phosphatase may include motif A represented by $X_{a1}$-$X_{a2}$-$X_{a3}$-DPLDG-$X_{a4}$ and motif B represented by $Y_{a1}$-D-$Y_{a2}$-$W_{a1}$-$Y_{a3}$-$W_{a2}$-$Y_{a4}$-$W_{a3}$. Herein, the inositol-mono-phosphatase may be used interchangeably with the psicose-6-phosphate phosphatase.

The method of the present application may further include, prior to the conversion of D-psicose-6-phosphate to D-psicose, bringing a D-fructose-6-phosphate-3-epimerase, a microorganism expressing the D-fructose-6-phosphate-3-epimerase or a culture of the microorganism expressing the D-fructose-6-phosphate-3-epimerase into contact with D-fructose-6-phosphate to convert the D-fructose-6-phosphate to D-psicose-6-phosphate.

The method of the present application may further include, prior to the conversion of D-fructose-6-phosphate to D-psicose-6-phosphate, bringing a D-glucose-6-phosphate-isomerase, a microorganism expressing the D-glucose-6-phosphate-isomerase or a culture of the microorganism expressing the D-glucose-6-phosphate-isomerase into contact with D-glucose-6-phosphate to convert the D-glucose-6-phosphate to D-fructose-6-phosphate.

The method of the present application may further include, prior to the conversion of D-glucose-6-phosphate to D-fructose-6-phosphate, bringing a phosphoglucomutase, a microorganism expressing the phosphoglucomutase or a culture of the microorganism expressing the phosphoglucomutase into contact with D-glucose-1-phosphate to convert the D-glucose-1-phosphate to D-glucose-6-phosphate.

The method of the present application may further include, prior to the conversion of D-glucose-6-phosphate to D-fructose-6-phosphate, bringing a glucokinase, a microorganism expressing the glucokinase or a culture of the microorganism expressing the glucokinase and a phosphate into contact with glucose to convert the glucose to D-glucose-6-phosphate.

The method of the present application may further include, prior to the conversion of D-glucose-1-phosphate to D-glucose-6-phosphate, bringing an α-glucan phosphorylase, a starch phosphorylase, a maltodextrin phosphorylase or a sucrose phosphorylase, a microorganism expressing the phosphorylase or a culture of the microorganism expressing the phosphorylase and a phosphate into contact with starch, maltodextrin, sucrose or a combination thereof to convert the starch, maltodextrin, sucrose or combination thereof to D-glucose-1-phosphate.

The method of the present application may further include, prior to the conversion of glucose to D-glucose-6-phosphate, bringing an α-amylase, a pullulanase, a glucoamylase, a sucrase or an isoamylase, a microorganism expressing the α-amylase, pullulanase, glucoamylase, sucrase or isoamylase or a culture of the microorganism expressing the α-amylase, pullulanase, glucoamylase, sucrase or isoamylase into contact with starch, maltodextrin, sucrose or a combination thereof to convert the starch, maltodextrin, sucrose or combination thereof to glucose.

Yet another aspect of the present application provides a method for producing D-psicose comprising bringing (a) an inositol-mono-phosphatase, a D-fructose-6-phosphate-3-epimerase, a D-glucose-6-phosphate-isomerase, a phosphoglucomutase or a glucokinase and an α-glucan phosphorylase, a starch phosphorylase, a maltodextrin phosphorylase, a sucrose phosphorylase, an α-amylase, a pullulanase, an isoamylase, a glucoamylase or a sucrase or (b) a microorganism expressing the enzymes (a) or a culture of the microorganism into contact with starch, maltodextrin, sucrose or a combination thereof and a phosphate.

In the method of the present application, the contact reaction may be carried out at a pH of 5.0 to 9.0, specifically a pH of 6.0 to 8.0.

In the method of the present application, the contact reaction may be carried out at a temperature of 40° C. to 80° C., specifically a temperature of 40° C. to 60° C. or 50° C. to 60° C.

In the method of the present application, the contact reaction may be carried out for 2 hours to 24 hours, specifically 6 to 24 hours.

In the method of the present application, the contact reaction may be carried out at a pH of 5.0 to 9.0, at a temperature of 40° C. to 80° C. and/or for 2 hours to 24 hours. Specifically, the contact reaction may be carried out at a pH of 6.0 to 8.0, at a temperature of 40° C. to 60° C. or 50° C. to 60° C. and/or for 6 hours to 24 hours.

The method of the present application may further comprise purifying the reaction product D-psicose. There is no particular restriction on the method for purifying D-psicose. D-psicose may be purified by any suitable method known in the art. Non-limiting examples of such purification methods include chromatography, fractional crystallization, and ion purification, which may be carried out alone or in combination. For example, D-psicose may be purified by chromatography. In this case, the target saccharide may be separated based on small differences in binding force between saccharides and metal ions attached to an ionic resin.

Each of the methods according to the present application may further comprise bleaching and/or demineralizing before or after the purification step. The bleaching and/or demineralizing makes D-psicose purer without impurities.

Advantageous Effects

The novel psicose-6-phosphate phosphatase of the present application is a thermoresistant inositol-mono-phosphatase. Due to its thermoresistance, the enzyme of the present application can participate in the pathway for the conversion of D-psicose-6-phosphate to D-psicose, enabling the production of D-psicose on an industrial scale. The use of the enzyme according to the present application allows the pathway for the synthesis of D-psicose from glucose or starch (e.g., maltodextrin) as an inexpensive raw material to proceed. In addition, when the enzyme of the present application is used, D-psicose can be produced through the irreversible dephosphorylation of D-psicose-6-phosphate. Therefore, the use of the enzyme according to the present application considerably increases the conversion rate to D-psicose.

Furthermore, the methods of the present application based on the use of the inositol-mono-phosphatase enable the production of a high concentration of D-psicose at a high conversion rate, simplifying or omitting the separation and purification of the reaction product. Therefore, the methods of the present application can be carried out in a simple manner and are advantageous from an economic viewpoint.

MODE FOR INVENTION

Figure 1:
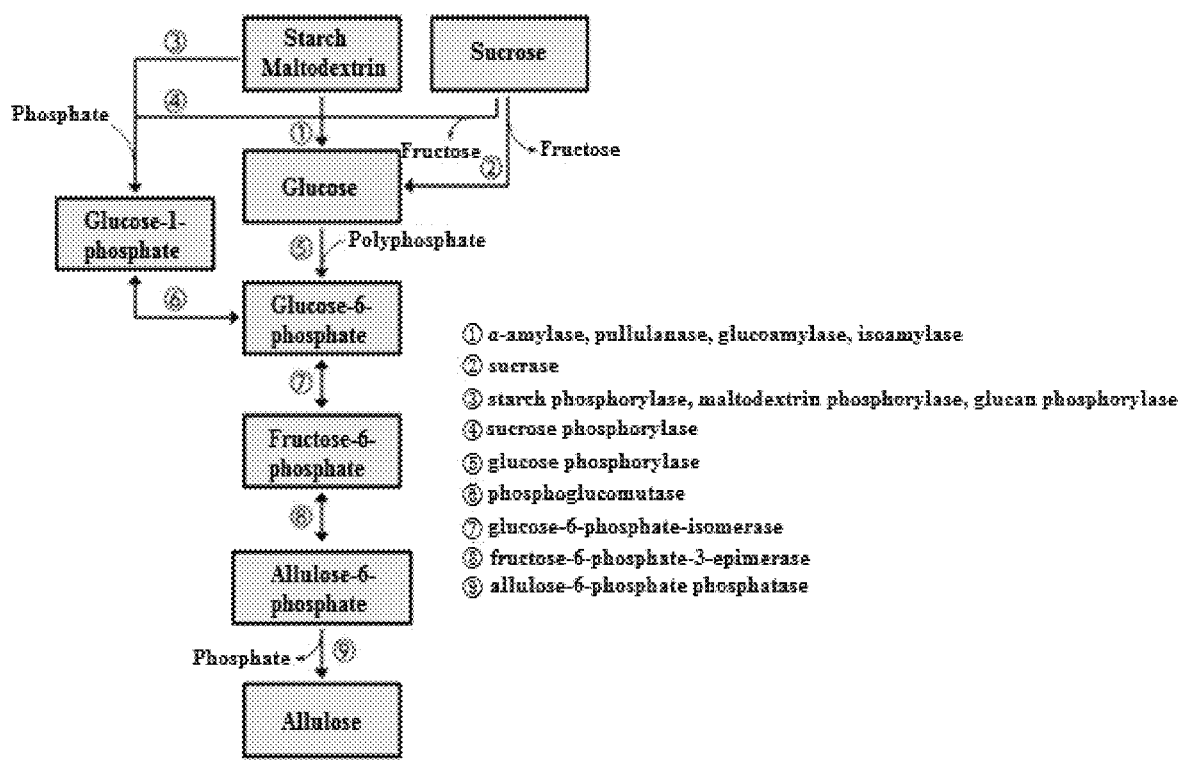
FIG. 1 schematically shows the enzymatic reaction pathways for the production of D-psicose from starch (e.g., maltodextrin) or glucose.

The present application will be explained in detail with reference to the following examples. However, these examples are provided to assist in understanding the present application and do not limit the scope of the present application.

EXAMPLES

Example 1: Production of Recombinant Expression Vectors of Inositol-Mono-Phosphatases and Transformed Microorganisms To provide psicose-6-phosphate phosphatase necessary for the D-psicose production pathway, thermoresistant inositol-mono-phosphatase genes were screened. Specifically, inositol-mono-phosphatase genes (Rma, Tle, Mrub, Dtu, Msi, Mruf, Mta, Mch, and Mce) were screened from the genomic sequences of *Rhodothermus marinus, Thermotoga lettingae, Meiothermus ruber, Dictyoglomus turgidum, Pyrobaculum ferrireducens, Thermoanaerobacter wiegelii, Thermus thermophilus, Thermococcus litoralis, Geobacillus stearothermophilus, Anaerolinea thermophila, Sulfolobus acidocaldarius, Thermosulfidibacter takai, Pyrococcus furiosus, Archaeoglobus fulgidus, Alicyclobacillus acidocaldarius, Meiothermus silvanus, Meiothermus rufus, Meiothermus taiwanensis, Meiothermus chliarophilus*, and *Meiothermus cerbereus* registered in GenBank.

Based on information on the nucleotide sequences (SEQ ID NOS: 21, 22, 23, 24, 36, 37, 38, 39, and 40 in the order of the genes) and the amino acid sequences (SEQ ID NOS: 1, 2, 3, 4, 16, 17, 18, 19, and 20 in the order of the genes) of the screened genes, forward primers (SEQ ID NOS: 41, 43, 45, 47, 49, 51, 53, 55, and 57) and reverse primers (SEQ ID NOS: 42, 44, 46, 48, 50, 52, 54, 56, and 58) were designed. The genes were amplified from the genomic DNAs of *Rhodothermus marinus, Thermotoga lettingae, Meiothermus ruber, Dictyoglomus turgidum, Meiothermus silvanus, Meiothermus rufus, Meiothermus taiwanensis, Meiothermus chliarophilus*, and *Meiothermus cerbereus* by polymerase chain reaction (PCR) using the synthesized primers. The amplified inositol-mono-phosphatase genes were inserted into plasmid vector pET21a (Novagen) for *E. coli* expression using restriction enzymes NdeI and XhoI or SalI to construct recombinant expression vectors, which were named pET21a-CJ_Rma(Nde I/Xho I), pET21a-CJ_Tle(Nde I/Xho I), pET21a-CJ_Mrub(Nde I/Xho I), pET21a-CJ_Dtu(Nde I/Xho I), pET21a-CJ_Msi(Nde I/Sal I), pET21a-CJ_Mruf(Nde I/Sal I), pET21a-CJ_Mta(Nde I/Sal I), pET21a-CJ_Mch(Nde I/Sal I), and pET21a-CJ_Mce (Nde I/Sal I).

Additionally, inositol-mono-phosphatase genes (Pfe, Twi, Tth, Tli, Gst, Ath, Sac, Tta, Pfu, Afu, and Aac) derived from *Pyrobaculum ferrireducens, Thermoanaerobacter wiegelii, Thermus thermophilus, Thermococcus litoralis, Geobacillus stearothermophilus, Anaerolinea thermophila, Sulfolobus acidocaldarius, Thermosulfidibacter takai, Pyrococcus furiosus, Archaeoglobus fulgidus*, and *Alicyclobacillus acidocaldarius* were screened. Based on information on the nucleotide sequences (SEQ ID NOS: 25, 26, 27, 28, 29, 30, 31, 32, 33, 34, and 35 in the order of the genes) and the amino acid sequences (SEQ ID NOS: 5, 6, 7, 8, 9, 10, 11, 12, 13, 14, and 15 in the order of the genes) of the screened genes, DNA synthesis was requested to Bioneer (Korea). The DNAs were inserted into vector pBT7-C-His (Bioneer) to construct recombinant expression vectors, which were named pBT7-C-His-CJ_Pfe, pBT7-C-His-CJ_Twi, pBT7-C-His-CJ_Tth, pBT7-C-His-CJ_Tli, pBT7-C-His-CJ_Gst, pBT7-C-His-CJ_Ath, pBT7-C-His-CJ_Sac, pBT7-C-His-CJ_Tta, pBT7-C-His-CJ_Pfu, pBT7-C-His-CJ_Afu, and pBT7-C-His-CJ_Aac.

The expression vectors were transformed into strain *E. coli* BL21(DE3) by a general transformation technique (see Sambrook et al. 1989) to produce transformed microorganisms, which were named *E. coli* BL21(DE3)/pET21a-CJ_Rma (*E. coli*_P1_CJ_Rma, KCCM12057P), *E. coli* BL21(DE3)/pET21a-CJ_Tle (*E. coli*_P2_CJ_Tle, KCCM12058P), *E. coli* BL21(DE3)/pET21a-CJ_Mrub (*E. coli*_P3_CJ_Mrub, KCCM12059P), *E. coli* BL21(DE3)/pET21a-CJ_Dtu (*E. coli*_P4_CJ_Dtu, KCCM12060P), *E. coli* BL21(DE3)/pBT7-C-His-CJ_Pfe (*E. coli*_P5_CJ_Pfe, KCCM12061P), *E. coli* BL21(DE3)/pBT7-C-His-CJ_Twi (*E. coli*_P6_CJ_Twi, KCCM12062P), *E. coli* BL21(DE3)/pBT7-C-His-CJ_Tth (*E. coli*_P7_CJ_Tth, KCCM12063P), *E. coli* BL21(DE3)/pBT7-C-His-CJ_Tli (*E. coli*_P8_CJ_Tli, KCCM12064P), *E. coli* BL21(DE3)/pBT7-C-His-CJ_Gst (*E. coli*_P9_CJ_Gst, KCCM12065P), *E. coli* BL21(DE3)/pBT7-C-His-CJ_Ath (*E. coli*_P10_CJ_Ath, KCCM12066P), *E. coli* BL21(DE3)/pBT7-C-His-CJ_Sac (*E. coli*_P11_CJ_Sac, KCCM12067P), *E. coli* BL21(DE3)/pBT7-C-His-CJ_Tta (*E. coli*_P12_CJ_Tta, KCCM12068P), *E. coli* BL21(DE3)/pBT7-C-His-CJ_Pfu (*E. coli*_P13_CJ_Pfu, KCCM12069P), *E. coli* BL21(DE3)/pBT7-C-His-CJ_Afu (*E. coli*_P14_CJ_Afu, KCCM12070P), *E. coli* BL21(DE3)/pBT7-C-His-CJ_Aac (*E. coli*_P15_CJ_Aac, KCCM12071P), *E. coli* BL21(DE3)/pET21a-CJ_Msi (*E. coli* P16_CJ_Msi, KCCM12072P), *E. coli* BL21(DE3)/pET21a-CJ_Mruf (*E. coli*_P17_CJ_Mruf, KCCM12073P), *E. coli* BL21(DE3)/pET21a-CJ_Mta (*E. coli*_P18_CJ_Mta, KCCM12074P), *E. coli* BL21(DE3)/pET21a-CJ_Mch (*E. coli*_P19_CJ_Mch, KCCM12075P), and *E. coli* BL21(DE3)/pET21a-CJ_Mce (*E. coli*_P20_CJ_Mce, KCCM12076P).

The transformed strains were deposited at the Korean Culture Center of Microorganisms (KCCM) on Jul. 10, 2017 under the Budapest Treaty (Accession Nos.: KCCM12057P to KCCM12076P).

Example 2: Production of Enzymes Necessary for D-Psicose Production Pathway

To provide an α-glucan phosphorylase, a phosphoglucomutase, a D-glucose-6-phosphate-isomerase, and a D-fructose-6-phosphate-3-epimerase derived from *Thermotoga neapolitana* as thermoresistant enzymes necessary for the D-psicose production pathway, genes corresponding to the enzymes were screened (ct1, ct2, tn1 and fp3e in the order of the enzymes).

Based on the nucleotide sequences (SEQ ID NOS: 60, 62, 64, and 66 in the order of the enzymes) and the amino acid sequences (SEQ ID NOS: 59, 61, 63, and 65 in the order of the enzymes) of the screened genes, forward primers (SEQ ID NOS: 69, 71, 73 and 75) and reverse primers (SEQ ID NOS: 70, 72, 74 and 76) were designed. The enzyme genes were amplified from the genomic DNA of *Thermotoga neapolitana* as a template by polymerase chain reaction (PCR) using the primers. PCR was performed for a total of 25 cycles using the following conditions: denaturization at 95° C. for 30 sec, annealing at 55° C. for 30 sec, and polymerization at 68° C. for 2 min. The amplified enzyme genes were inserted into plasmid vector pET21a (Novagen) for *E. coli* expression using restriction enzymes NdeI and XhoI to construct recombinant expression vectors, which were named pET21a-CJ_ct1, pET21a-CJ_ct2, pET21a-CJ_tn1, and pET21a-CJ_fp3e. The recombinant expression vectors were transformed into strain *E. coli* BL21(DE3) by a general transformation technique (see Sambrook et al. 1989) to produce transformed microorganisms, which were named *E. coli* BL21(DE3)/pET21a-CJ_ct1 (KCCM11990P), *E. coli* BL21(DE3)/pET21a-CJ_ct2 (KCCM11991P), *E. coli* BL21(DE3)/pET21a-CJ_tn1 (KCCM11992P), and *E. coli* BL21(DE3)/CJ_tn_fp3e (KCCM11848P). The strains were deposited at the Korean Culture Center of Microorganisms (KCCM) on Jun. 23, 2016 under the Budapest Treaty.

Example 3: Production of Recombinant Enzymes

In this example, recombinant enzymes were produced. First, a culture tube containing 5 ml of LB liquid medium was inoculated with each of the transformed microorganisms produced in Examples 1 and 2. The inoculum was cultured in a shaking incubator at 37° C. until an absorbance of 2.0 at 600 nm was reached. The culture broth was added to LB liquid medium in a culture flask, followed by main culture. When the absorbance of the culture at 600 nm reached 2.0, 1 mM IPTG was added to induce the expression and production of a recombinant enzyme. The culture temperature was maintained at 37° C. with stirring at 180 rpm. The culture broth was centrifuged at 8,000×g and 4° C. for 20 min to collect bacterial cells. The collected bacterial cells were washed twice with 50 mM Tris-HCl buffer (pH 8.0) and suspended in the same buffer. Then, cells were disrupted using an ultrasonic homogenizer. The cell lysate was centrifuged at 13,000×g and 4° C. for 20 min. The recombinant enzyme was purified from the supernatant by His-tag affinity chromatography. The purified recombinant enzyme was dialyzed against 50 mM Tris-HCl buffer (pH 8.0) and was then used for subsequent reaction. The molecular weight of the purified recombinant enzyme was determined by SDS-PAGE.

Figure 2A:
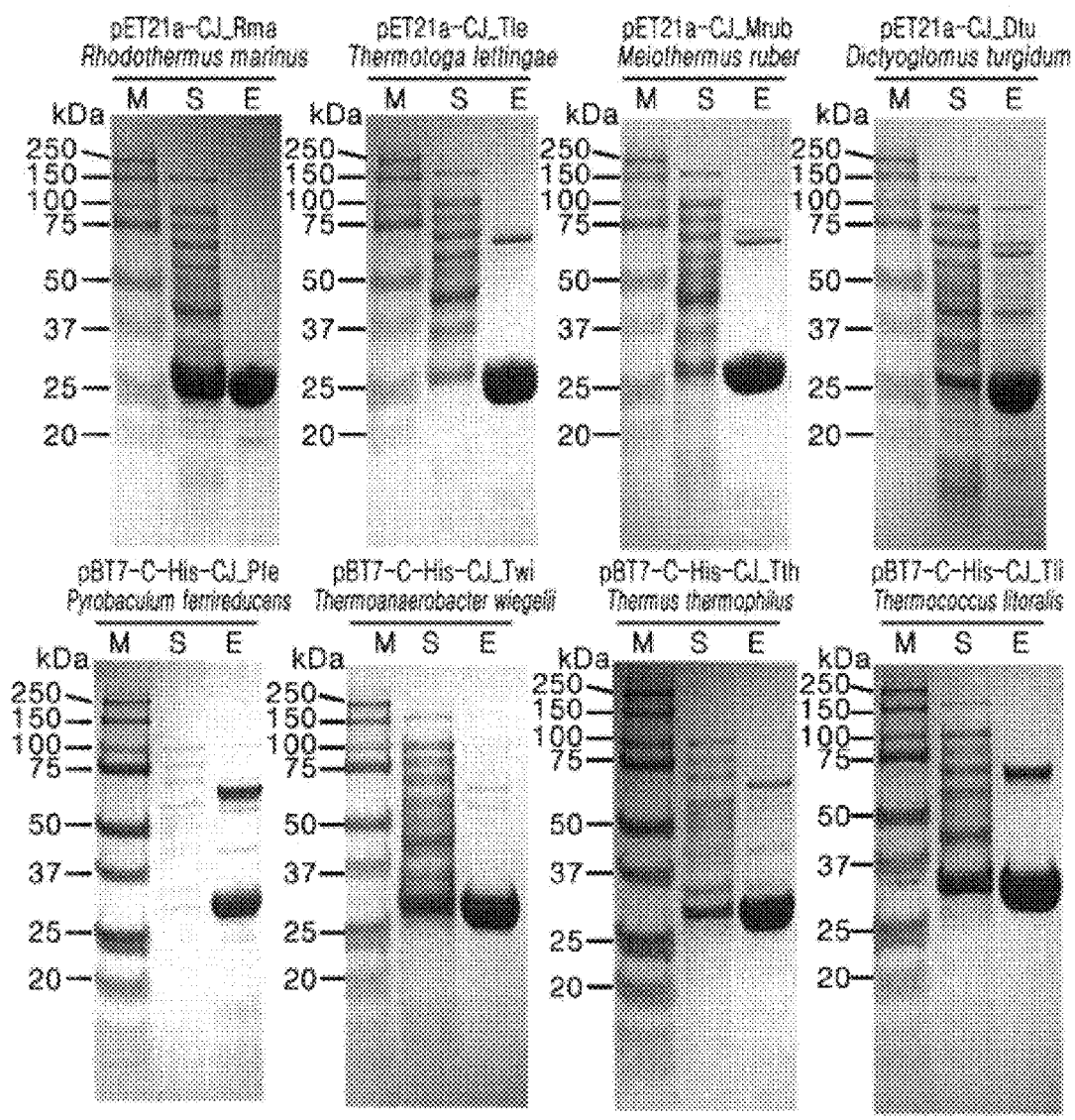
FIGS. 2a, 2b and 2c show SDS-PAGE gel images of size markers (M), expressed coenzymes (S), and purified recombinant enzymes (E) (pET21a-CJ_Rma, pET21a-CJ_Tle, pET21a-CJ_Mrub, pET21a-CJ_Dtu, pBT7-C-His-CJ_Pfe, pBT7-C-His-CJ_Twi, pBT7-C-His-CJ_Tth, pBT7-C-His-CJ_Tli, pBT7-C-His-CJ_Gst, pBT7-C-His-CJ_Ath, pBT7-C-His-CJ_Sac, pBT7-C-His-CJ_Tta, pBT7-C-His-CJ_Pfu, pBT7-C-His-CJ_Afu, pBT7-C-His-CJ_Aac, pET21a-CJ_Msi, pET21a-CJ_Mruf, pET21a-CJ_Mta, pET21a-CJ_Mch, pET21a-CJ_Mce) to determine molecular weights thereof, which were taken after protein electrophoresis.
Figure 2B:
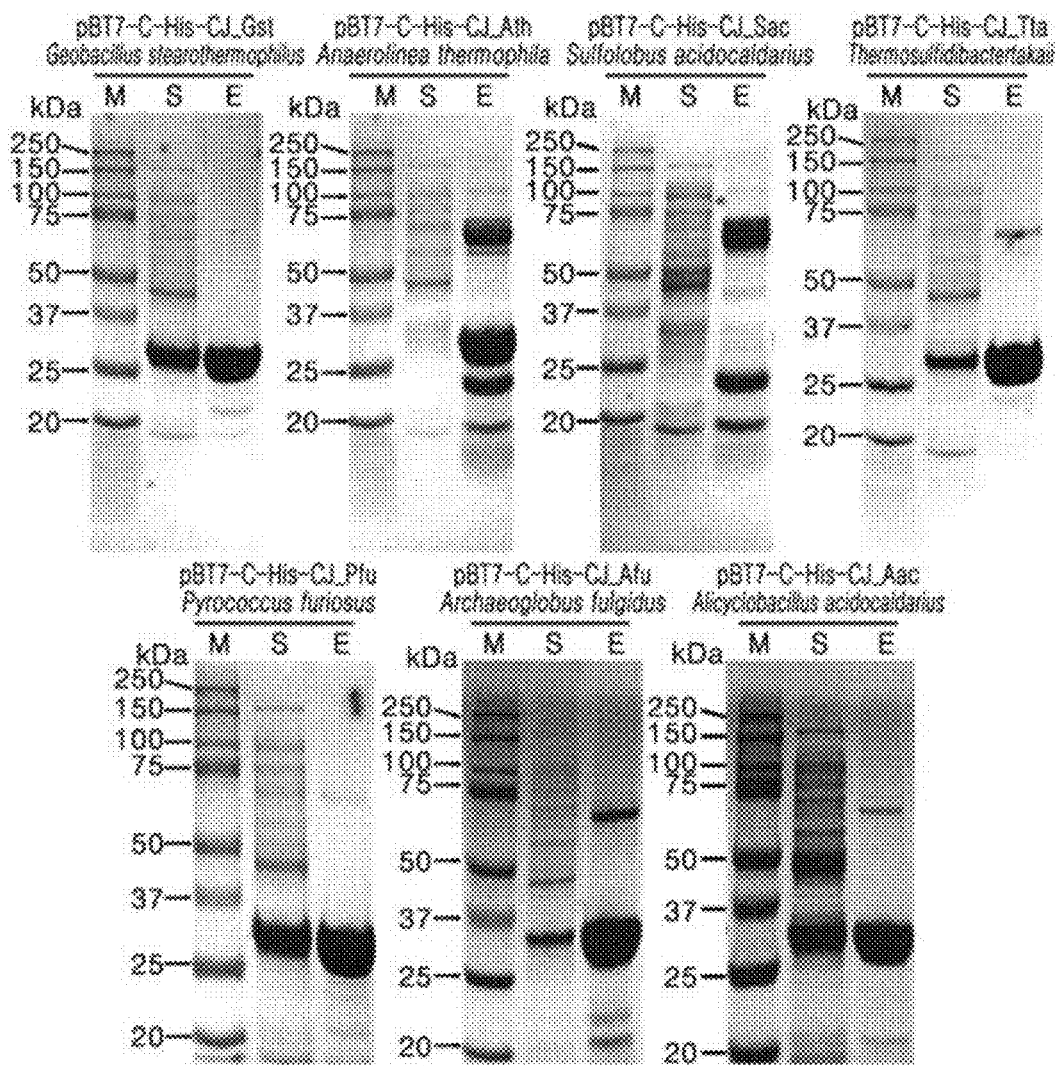
Figure 2C:
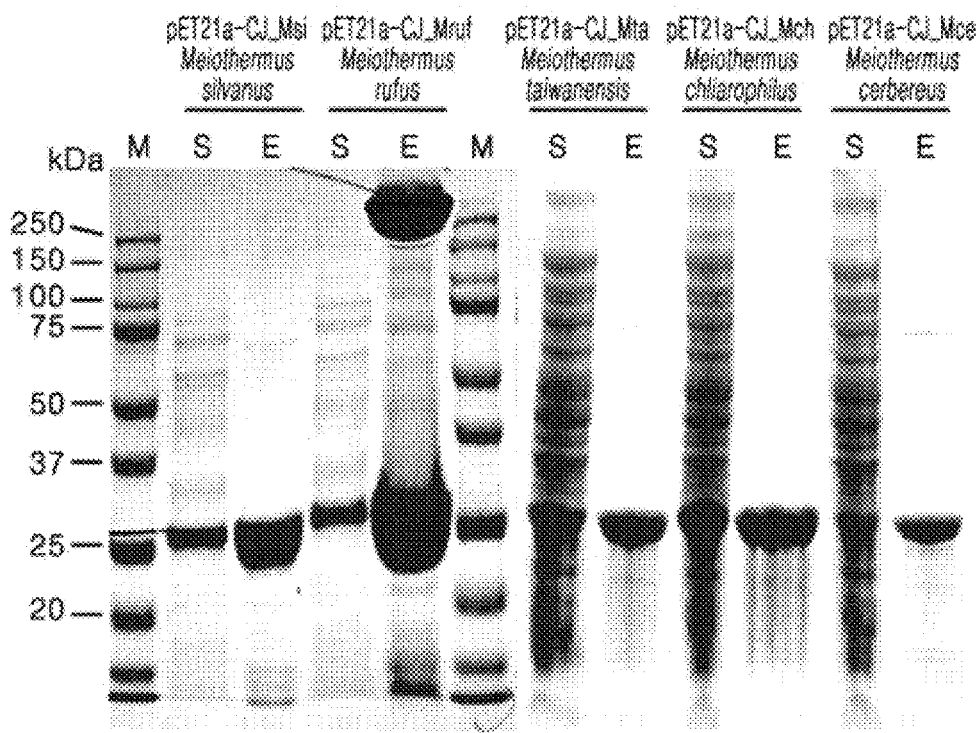

The names and molecular weights of the purified enzymes produced using the transformed microorganisms are as follows (FIGS. 2*a*, 2*b* and 2*c*):

30.3 kDa for the enzyme (RMA) produced from *E. coli* BL21(DE3))/pET21a-CJ_Rma (*E. coli*_P1_CJ_Rma);

28.5 kDa for the enzyme (TLE) produced from *E. coli* BL21(DE3)/pET21a-CJ_Tle (*E. coli*_P2_CJ_Tle);

28 kDa for the enzyme (MRUB) produced from *E. coli* BL21(DE3)/pET21a-CJ_Mrub (*E. coli*_P3_CJ_Mrub);

30.2 kDa for the enzyme (DTU) produced from *E. coli* BL21(DE3)/pET21a-CJ_Dtu (*E. coli*_P4_CJ_Dtu);

kDa for the enzyme (PFE) produced from *E. coli* BL21(DE3)/pBT7-C-His-CJ_Pfe (*E. coli*_P5_CJ_Pfe);

28.8 kDa for the enzyme (TWI) produced from *E. coli* BL21(DE3)/pBT7-C-His-CJ_Twi (*E. coli*_P6_CJ_Twi);

kDa for the enzyme (TTH) produced from *E. coli* BL21(DE3)/pBT7-C-His-CJ_Tth (*E. coli* P7_CJ_Tth);

28 kDa for the enzyme (TLI) produced from *E. coli* BL21(DE3)/pBT7-C-His-CJ_Tli (*E. coli*_P8_CJ_Tli);

kDa for the enzyme (GST) produced from *E. coli* BL21(DE3)/pBT7-C-His-CJ_Gst (*E. coli*_P9_CJ_Gst);

28.7 kDa for the enzyme (ATH) produced from *E. coli* BL21(DE3)/pBT7-C-His-CJ_Ath (*E. coli*_P10_CJ_Ath);

kDa for the enzyme (SAC) produced from *E. coli* BL21(DE3)/pBT7-C-His-CJ_Sac (*E. coli*_P11_CJ_Sac);

28.6 kDa for the enzyme (TTA) produced from *E. coli* BL21(DE3)/pBT7-C-His-CJ_Tta (*E. coli*_P12_CJ_Tta);

27.9 kDa for the enzyme (PFU) produced from *E. coli* BL21(DE3)/pBT7-C-His-CJ_Pfu (*E. coli*_P13_CJ_Pfu);

28 kDa for the enzyme (AFU) produced from *E. coli* BL21(DE3)/pBT7-C-His-CJ_Afu (*E. coli*_P14_CJ_Afu);

29 kDa for the enzyme (AAC) produced from *E. coli* BL21(DE3)/pBT7-C-His-CJ_Aac (*E. coli*_P15_CJ_Aac);

28.1 kDa for the enzyme (MSI) produced from *E. coli* BL21(DE3)/pET21a-CJ_Msi (*E. coli*_P16_CJ_Msi);

28 kDa for the enzyme (MRUF) produced from *E. coli* BL21(DE3)/pET21a-CJ_Mruf (*E. coli*_P17_CJ_Mruf);

28.1 kDa for the enzyme (MTA) produced from *E. coli* BL21(DE3))/pET21a-CJ_Mta (*E. coli*_P18_CJ_Mta);

28.4 kDa for the enzyme (MCH) produced from *E. coli* BL21(DE3))/pET21a-CJ_Mch (*E. coli*_P19_CJ_Mch);

28.1 kDa for the enzyme (MCE) produced from *E. coli* BL21(DE3))/pET21a-CJ_Mce (*E. coli*_P20_CJ_Mce);

The enzyme (CT1) produced from *E. coli* BL21(DE3)/pET21a-CJ_ct1 (KCCM11990P);

The enzyme (CT2) produced from *E. coli* BL21(DE3)/pET21a-CJ_ct2 (KCCM11991P);

The enzyme (TN1) produced from *E. coli* BL21(DE3)/pET21a-CJ_tn1 (KCCM11992P); and The enzyme (FP3E) produced from *E. coli* BL21(DE3)/CJ_tn_fp3e (KCCM11848P).

Example 4: Analysis of Activities of the Inositol-Mono-Phosphatases 4-1. Analysis of Activities of the Psicose-6-Phosphate Phosphatases Psicose-6-phosphate was difficult to purchase. Thus, the inventors directly produced D-psicose-6-phosphate from D-fructose-6-phosphate and investigated the activities of the inositol-mono-phosphatases for D-psicose production.

Specifically, 50 mM D-fructose-6-phosphate was suspended in 50 mM Tris-HCl (pH 7.0), and then the D-fructose-6-phosphate-3-epimerase (FP3E) produced in Example 3 and 0.1 unit/ml of each of the 20 inositol-mono-phosphatases were added thereto. The mixture was allowed to react at 70° C. for 1 h. The production of D-psicose was confirmed by HPLC (SP_0810 column (SHODEX), AMINEX HPX-87C column (BIO-RAD), 80° C., mobile phase flow rate 0.6 ml/min, refractive index detector).

Figure 3A:
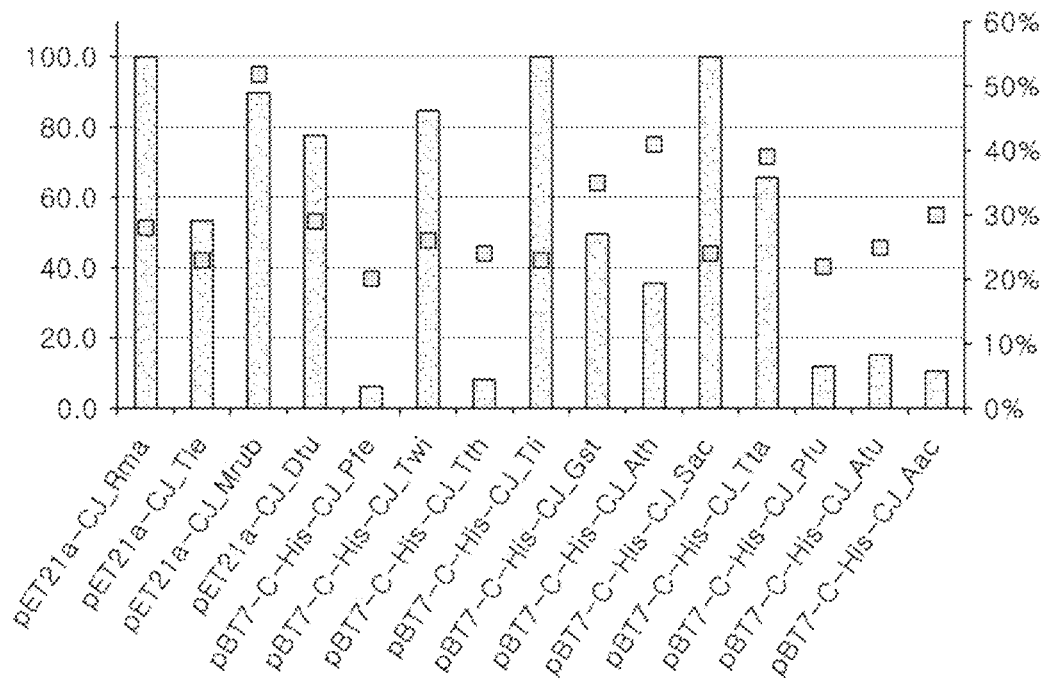
FIG. 3a shows the relative activities of inositol-mono-phosphatases (pET21a-CJ_Rma, pET21a-CJ_Tle, pET21a-CJ_Mrub, pET21a-CJ_Dtu, pBT7-C-His-CJ_Pfe, pBT7-C-His-CJ_Twi, pBT7-C-His-CJ_Tth, pBT7-C-His-CJ_Tli, pBT7-C-His-CJ_Gst, pBT7-C-His-CJ_Ath, pBT7-C-His-CJ_Sac, pBT7-C-His-CJ_Tta, pBT7-C-His-CJ_Pfu, pBT7-C-His-CJ_Afu, pBT7-C-His-CJ_Aac) for dephosphorylation (%, left Y axis, histogram) and the selective dephosphorylation rates by the inositol-mono-phosphatases in a dephosphorylation mixture containing D-glucose-6-phosphate, D-glucose-1-phosphate, D-fructose-6-phosphate, and D-psicose-6-phosphate (%, right Y axis, square dots).
Figure 3B:
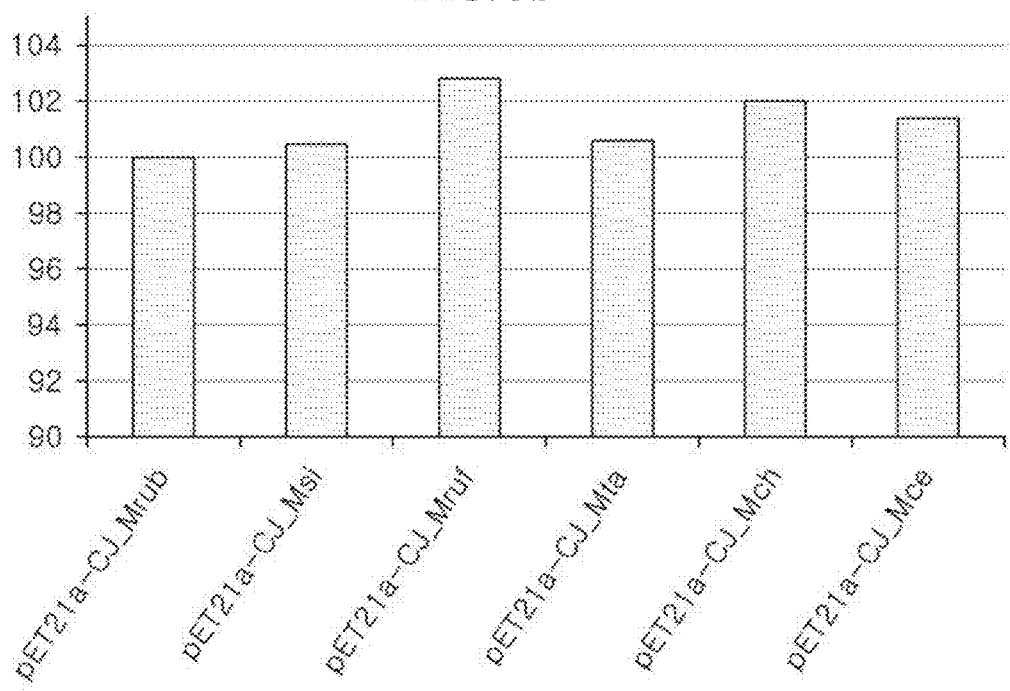
FIG. 3b compares the relative activities (%) of inositol-mono-phosphatases (pET21a-CJ_Mrub, pET21a-CJ_Msi, pET21a-CJ_Mruf, pET21a-CJ_Mta, pET21a-CJ_Mch, pET21a-CJ_Mce) for dephosphorylation.

The dephosphorylation potency of the all 20 inositol-mono-phosphatases for D-psicose-6-phosphate were investigated (FIGS. 3a and 3b).

4-2. Analysis of Activities of the Inositol-Mono-Phosphatases for Specific Dephosphorylation of D-Psicose-6-Phosphate The specific dephosphorylation rates of D-psicose-6-phosphate in a mixture containing D-glucose-6-phosphate, D-glucose-1-phosphate, D-fructose-6-phosphate, and D-psicose-6-phosphate in the presence of the inositol-mono-phosphatases were measured.

Specifically, 0.1 unit/ml of each of the inositol-mono-phosphatases and 5 mM $MgCl_2$ were added to a mixture of 1% (w/v) D-glucose-6-phosphate, D-glucose-1-phosphate, D-fructose-6-phosphate, and D-psicose-6-phosphate. The reaction was allowed to proceed at 50° C. for 12 h. The reaction products were analyzed by HPLC (AMINEX HPX-87C column (BIO-RAD), 80° C., mobile phase flow rate 0.6 ml/min). A refractive index detector was used to detect the production of D-psicose and other saccharides (fructose and glucose).

As a result, the enzyme MRUB showed the highest specific dephosphorylation rate of D-psicose-6-phosphate (FIG. 3a).

Example 5: Analysis of Activities of the Enzymes Through Multiple Enzymatic Reactions For the production of D-psicose from maltodextrin, the enzymes CT1, CT2, TN1, FP3E and MRUB were allowed to simultaneously react with maltodextrin. 5% (w/v) maltodextrin was added to 0.1 unit/ml of each enzyme, 5 mM $MgCl_2$, and 20 mM sodium phosphate (pH 7.0). The mixture was allowed to react at a temperature of 50° C. for 12 h. The reaction products were analyzed by HPLC (AMINEX HPX-87C column (BIO-RAD), 80° C., mobile phase flow rate 0.6 ml/min, refractive index detector).

Figure 4A:
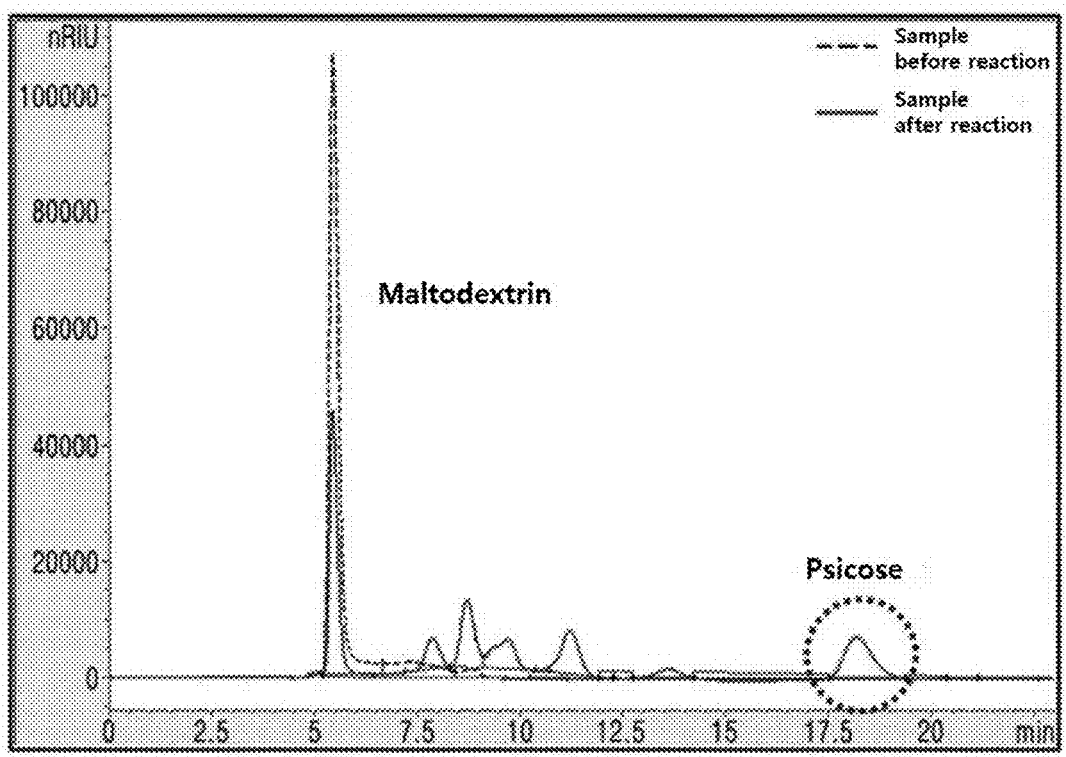
FIG. 4a shows HPLC chromatograms confirming the production of D-psicose from maltodextrin through multiple enzymatic reactions with an α-glucan phosphorylase, a phosphoglucomutase, a D-glucose-6-phosphate-isomerase, a 4-α-glucanotransferase, a D-fructose-6-phosphate-3-epimerase, and a psicose-6-phosphate phosphatase.
Figure 4B:
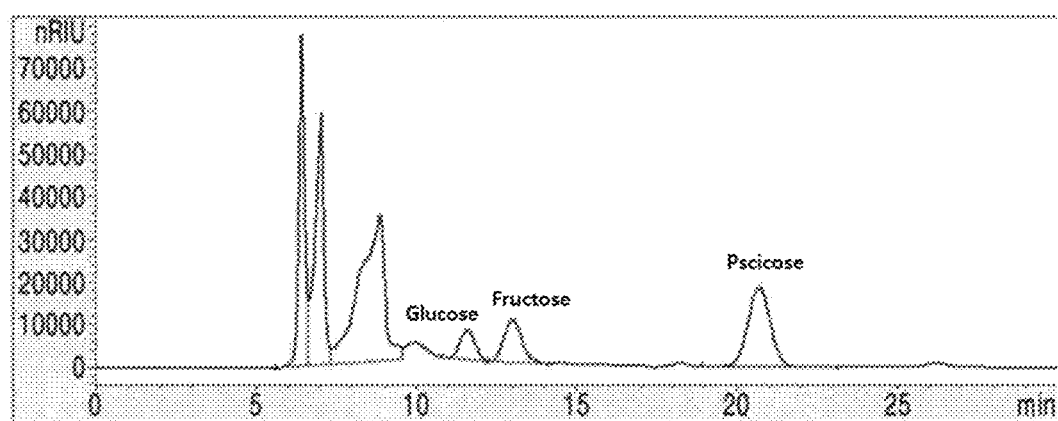
FIG. 4b shows HPLC chromatograms confirming the production of D-psicose through selective dephosphorylation of D-psicose-6-phosphate in a reaction solution containing D-glucose-1-phosphate, D-glucose-6-phosphate, D-fructose-6-phosphate, and D-psicose-6-phosphate in the presence of an inositol-mono-phosphatase according to the present application.

As a result, the production of D-psicose from maltodextrin through the multiple enzymatic reactions was confirmed (FIG. 4a).

While the embodiment of the present application has been described in detail, it will be understood by those skilled in the art that the application can be implemented in other specific forms without changing the spirit or essential features of the application. Therefore, it should be noted that the forgoing embodiments are merely illustrative in all aspects and are not to be construed as limiting the application. The scope of the application is defined by the appended claims rather than the detailed description of the application. All changes or modifications or their equivalents made within the meanings and scope of the claims should be construed as falling within the scope of the application.

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __9__, line __3__.

B. IDENTIFICATION OF DEPOSIT  Further deposits are identified on an additional sheet☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| July 10, 2017 | KCCM12057P |

C. ADDITIONAL INDICATIONS *(leave blank if not applicable)*   This information is continued on an additional sheet☐

D. DESIGNATED STATES FOR WHICH INDICATIONS ARE MADE *(if the indications are not for all designated States)*

E. SEPARATE FURNISHING OF INDICATIONS *(leave blank if not applicable)*
The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1998; reprint January 2004)

| Applicant's or agent's file reference | P18-6064 | International application No. |
|---|---|---|

INDICATIONS RELATING TO DEPOSITED MICROORGANISM
OR OTHER BIOLOGICAL MATERIAL (PCT Rule 13*bis*)

| A. The indications made below relate to the deposited microorganism or other biological material referred to in the description on page __9__ , line __4__ . |
|---|
| B. IDENTIFICATION OF DEPOSIT  Further deposits are identified on an additional sheet ☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |

| Date of deposit | Accession Number |
|---|---|
| July 10, 2017 | KCCM12058P |

| C. ADDITIONAL INDICATIONS *(leave blank if not applicable)*    This information is continued on an additional sheet ☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. |
|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __9__ , line __5__ . |
|---|
| B. IDENTIFICATION OF DEPOSIT  Further deposits are identified on an additional sheet☐ |
| Name of depositary institution Korean Culture Center of Microorganisms (KCCM) |
| Address of depositary institution *(including postal code and country)* Yurim Building, Hongjenae-2ga-gil 45, Seodaemun-Gu, Seoul, 120-091, Republic of Korea |

| Date of deposit July 10, 2017 | Accession Number KCCM12059P |
|---|---|

| C. ADDITIONAL INDICATIONS *(leave blank if not applicable)* This information is continued on an additional sheet☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only ☐ This sheet was received with the international application | For International Bureau use only ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page ___9___ , line ___6___ .

B. IDENTIFICATION OF DEPOSIT      Further deposits are identified on an additional sheet ☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| July 10, 2017 | KCCM12060P |

C. ADDITIONAL INDICATIONS *(leave blank if not applicable)*      This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __9__ , line __7__ .

B. IDENTIFICATION OF DEPOSIT — Further deposits are identified on an additional sheet ☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| July 10, 2017 | KCCM12061P |

C. ADDITIONAL INDICATIONS *(leave blank if not applicable)* — This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*
The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description |
|---|
| on page ___9___ , line ___8___ . |
| B. IDENTIFICATION OF DEPOSIT      Further deposits are identified on an additional sheet ☐ |
| Name of depositary institution <br> Korean Culture Center of Microorganisms (KCCM) |
| Address of depositary institution *(including postal code and country)* <br> Yurim Building, Hongjenae-2ga-gil 45, Seodaemun-Gu, Seoul, 120-091, Republic of Korea |

| Date of deposit | Accession Number |
|---|---|
| July 10, 2017 | KCCM12062P |

| C. ADDITIONAL INDICATIONS *(leave blank if not applicable)*    This information is continued on an additional sheet ☐ |
|---|
| |
| D. DESIGNATED STATES FOR WHICH INDICATIONS ARE MADE *(if the indications are not for all designated States)* |
| |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only <br> ☐ This sheet was received with the international application | For International Bureau use only <br> ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page 9 , line 9 . |
|---|
| B. IDENTIFICATION OF DEPOSIT  Further deposits are identified on an additional sheet ☐ |
| Name of depositary institution  Korean Culture Center of Microorganisms (KCCM) |
| Address of depositary institution *(including postal code and country)*  Yurim Building, Hongjenae-2ga-gil 45, Seodaemun-Gu, Seoul, 120-091, Republic of Korea |

| Date of deposit | Accession Number |
|---|---|
| July 10, 2017 | KCCM12063P |

| C. ADDITIONAL INDICATIONS *(leave blank if not applicable)*  This information is continued on an additional sheet ☐ |
|---|
|  |

| D. DESIGNATED STATES FOR WHICH INDICATIONS ARE MADE *(if the indications are not for all designated States)* |
|---|
|  |

| E. SEPARATE FURNISHING OF INDICATIONS *(leave blank if not applicable)* |
|---|
| The indications listed below will be submitted to the International Bureau later *(specify the general nature of the indications e.g., "Accession Number of Deposit")* |

| For receiving Office use only  ☐ This sheet was received with the international application | For International Bureau use only  ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. |
|---|---|---|

INDICATIONS RELATING TO DEPOSITED MICROORGANISM
OR OTHER BIOLOGICAL MATERIAL (PCT Rule 13*bis*)

| A. The indications made below relate to the deposited microorganism or other biological material referred to in the description on page __9__, line __10__. |||
|---|---|---|
| B. IDENTIFICATION OF DEPOSIT || Further deposits are identified on an additional sheet ☐ |
| Name of depositary institution<br>Korean Culture Center of Microorganisms (KCCM) |||
| Address of depositary institution *(including postal code and country)*<br>Yurim Building, Hongjenae-2ga-gil 45, Seodaemun-Gu, Seoul, 120-091, Republic of Korea |||
| Date of deposit<br>July 10, 2017 | Accession Number<br>KCCM12064P ||
| C. ADDITIONAL INDICATIONS *(leave blank if not applicable)*   This information is continued on an additional sheet ☐ |||
|  |||
| D. DESIGNATED STATES FOR WHICH INDICATIONS ARE MADE *(if the indications are not for all designated States)* |||
|  |||
| E. SEPARATE FURNISHING OF INDICATIONS *(leave blank if not applicable)* |||
| The indications listed below will be submitted to the International Bureau later *(specify the general nature of the indications e.g., "Accession Number of Deposit")* |||

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __9__ , line __11__ . |  |
|---|---|
| B. IDENTIFICATION OF DEPOSIT Further deposits are identified on an additional sheet ☐ |  |
| Name of depositary institution Korean Culture Center of Microorganisms (KCCM) |  |
| Address of depositary institution *(including postal code and country)* Yurim Building, Hongjenae-2ga-gil 45, Seodaemun-Gu, Seoul, 120-091, Republic of Korea |  |
| Date of deposit July 10, 2017 | Accession Number KCCM12065P |
| C. ADDITIONAL INDICATIONS *(leave blank if not applicable)* This information is continued on an additional sheet ☐ |  |
|  |  |
| D. DESIGNATED STATES FOR WHICH INDICATIONS ARE MADE *(if the indications are not for all designated States)* |  |
|  |  |
| E. SEPARATE FURNISHING OF INDICATIONS *(leave blank if not applicable)* |  |
| The indications listed below will be submitted to the International Bureau later *(specify the general nature of the indications e.g., "Accession Number of Deposit")* |  |

| For receiving Office use only ☐ This sheet was received with the international application | For International Bureau use only ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page ___9___ , line ___12___ . |
|---|
| B. IDENTIFICATION OF DEPOSIT  Further deposits are identified on an additional sheet☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |

| Date of deposit<br>July 10, 2017 | Accession Number<br>KCCM12066P |
|---|---|

| C. ADDITIONAL INDICATIONS *(leave blank if not applicable)*   This information is continued on an additional sheet☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page   9  , line   13  . |
|---|
| B. IDENTIFICATION OF DEPOSIT      Further deposits are identified on an additional sheet ☐ |
| Name of depositary institution <br> Korean Culture Center of Microorganisms (KCCM) |
| Address of depositary institution *(including postal code and country)* <br> Yurim Building, Hongjenae-2ga-gil 45, Seodaemun-Gu, Seoul, 120-091, Republic of Korea |

| Date of deposit <br> July 10, 2017 | Accession Number <br> KCCM12067P |
|---|---|

| C. ADDITIONAL INDICATIONS *(leave blank if not applicable)*     This information is continued on an additional sheet ☐ |
|---|
| |
| D. DESIGNATED STATES FOR WHICH INDICATIONS ARE MADE *(if the indications are not for all designated States)* |
| |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only <br> ☐ This sheet was received with the international application | For International Bureau use only <br> ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. |
|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __9__ , line __14__ .

B. IDENTIFICATION OF DEPOSIT          Further deposits are identified on an additional sheet☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| July 10, 2017 | KCCM12068P |

C. ADDITIONAL INDICATIONS *(leave blank if not applicable)*    This information is continued on an additional sheet☐

D. DESIGNATED STATES FOR WHICH INDICATIONS ARE MADE *(if the indications are not for all designated States)*

E. SEPARATE FURNISHING OF INDICATIONS *(leave blank if not applicable)*
The indications listed below will be submitted to the International Bureau later *(specify the general nature of the indications e.g., "Accession Number of Deposit")*

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __9__ , line __15__ . |
|---|
| B. IDENTIFICATION OF DEPOSIT   Further deposits are identified on an additional sheet☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |

| Date of deposit | Accession Number |
|---|---|
| July 10, 2017 | KCCM12069P |

| C. ADDITIONAL INDICATIONS *(leave blank if not applicable)*   This information is continued on an additional sheet☐ |
|---|
| |
| D. DESIGNATED STATES FOR WHICH INDICATIONS ARE MADE *(if the indications are not for all designated States)* |
| |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __9__, line __16__.

B. IDENTIFICATION OF DEPOSIT  Further deposits are identified on an additional sheet ☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| July 10, 2017 | KCCM12070P |

C. ADDITIONAL INDICATIONS *(leave blank if not applicable)*   This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page ___9___, line ___17___ . |
|---|
| B. IDENTIFICATION OF DEPOSIT    Further deposits are identified on an additional sheet☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |

| Date of deposit<br>July 10, 2017 | Accession Number<br>KCCM12071P |
|---|---|

| C. ADDITIONAL INDICATIONS *(leave blank if not applicable)*    This information is continued on an additional sheet☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __9__ , line __18__ . |
|---|
| B. IDENTIFICATION OF DEPOSIT   Further deposits are identified on an additional sheet☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |

| Date of deposit<br>July 10, 2017 | Accession Number<br>KCCM12072P |
|---|---|

| C. ADDITIONAL INDICATIONS *(leave blank if not applicable)*    This information is continued on an additional sheet☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page ___9___, line ___19___ . |  |
|---|---|
| B. IDENTIFICATION OF DEPOSIT | Further deposits are identified on an additional sheet ☐ |
| Name of depositary institution Korean Culture Center of Microorganisms (KCCM) | |
| Address of depositary institution *(including postal code and country)* Yurim Building, Hongjenae-2ga-gil 45, Seodaemun-Gu, Seoul, 120-091, Republic of Korea | |
| Date of deposit July 10, 2017 | Accession Number KCCM12073P |
| C. ADDITIONAL INDICATIONS *(leave blank if not applicable)* | This information is continued on an additional sheet ☐ |
|  | |
| D. DESIGNATED STATES FOR WHICH INDICATIONS ARE MADE *(if the indications are not for all designated States)* | |
|  | |
| E. SEPARATE FURNISHING OF INDICATIONS *(leave blank if not applicable)* | |
| The indications listed below will be submitted to the International Bureau later *(specify the general nature of the indications e.g., "Accession Number of Deposit")* | |

| For receiving Office use only ☐ This sheet was received with the international application | For International Bureau use only ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __9__ , line __20__ .

B. IDENTIFICATION OF DEPOSIT   Further deposits are identified on an additional sheet ☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| July 10, 2017 | KCCM12074P |

C. ADDITIONAL INDICATIONS *(leave blank if not applicable)*   This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __9__ , line __21__ . |
|---|
| B. IDENTIFICATION OF DEPOSIT  Further deposits are identified on an additional sheet ☐ |
| Name of depositary institution  Korean Culture Center of Microorganisms (KCCM) |
| Address of depositary institution *(including postal code and country)*  Yurim Building, Hongjenae-2ga-gil 45, Seodaemun-Gu, Seoul, 120-091, Republic of Korea |

| Date of deposit | Accession Number |
|---|---|
| July 10, 2017 | KCCM12075P |

| C. ADDITIONAL INDICATIONS *(leave blank if not applicable)*   This information is continued on an additional sheet ☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only  ☐ This sheet was received with the international application | For International Bureau use only  ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __9__, line __22__. |
|---|
| B. IDENTIFICATION OF DEPOSIT   Further deposits are identified on an additional sheet ☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |
| Date of deposit July 10, 2017 | Accession Number KCCM12076P |
| C. ADDITIONAL INDICATIONS *(leave blank if not applicable)*   This information is continued on an additional sheet ☐ |
| |
| D. DESIGNATED STATES FOR WHICH INDICATIONS ARE MADE *(if the indications are not for all designated States)* |
| |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __18__ , line __2__ . |
|---|
| B. IDENTIFICATION OF DEPOSIT  Further deposits are identified on an additional sheet ☐ |
| Name of depositary institution  Korean Culture Center of Microorganisms (KCCM) |
| Address of depositary institution *(including postal code and country)*  Yurim Building, Hongjenae-2ga-gil 45, Seodaemun-Gu, Seoul, 120-091, Republic of Korea |
| Date of deposit March 20, 2017      Accession Number KCCM11990P |
| C. ADDITIONAL INDICATIONS *(leave blank if not applicable)*  This information is continued on an additional sheet ☐ |
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only  ☐ This sheet was received with the international application | For International Bureau use only  ☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. |
|---|---|---|

INDICATIONS RELATING TO DEPOSITED MICROORGANISM OR OTHER BIOLOGICAL MATERIAL (PCT Rule 13*bis*)

| A. The indications made below relate to the deposited microorganism or other biological material referred to in the description on page __18__ , line __3__ . |
|---|
| B. IDENTIFICATION OF DEPOSIT   Further deposits are identified on an additional sheet☐ |
| Name of depositary institution<br>Korean Culture Center of Microorganisms (KCCM) |
| Address of depositary institution *(including postal code and country)*<br>Yurim Building, Hongjenae-2ga-gil 45, Seodaemun-Gu, Seoul, 120-091, Republic of Korea |

| Date of deposit<br>March 20, 2017 | Accession Number<br>KCCM11991P |
|---|---|

| C. ADDITIONAL INDICATIONS *(leave blank if not applicable)*   This information is continued on an additional sheet☐ |
|---|
|  |
| D. DESIGNATED STATES FOR WHICH INDICATIONS ARE MADE *(if the indications are not for all designated States)* |
|  |
| E. SEPARATE FURNISHING OF INDICATIONS *(leave blank if not applicable)* |
| The indications listed below will be submitted to the International Bureau later *(specify the general nature of the indications e.g., "Accession Number of Deposit")* |

| For receiving Office use only<br>☐ This sheet was received with the international application | For International Bureau use only<br>☐ This sheet was received by the International Bureau on: |
|---|---|
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __18__, line __4__.

B. IDENTIFICATION OF DEPOSIT     Further deposits are identified on an additional sheet ☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| March 20, 2017 | KCCM11992P |

C. ADDITIONAL INDICATIONS *(leave blank if not applicable)*     This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1998; reprint January 2004)

| Applicant's or agent's file reference | P18-6064 | International application No. | |
|---|---|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page __18__ , line __5__ .

B. IDENTIFICATION OF DEPOSIT  Further deposits are identified on an additional sheet ☐

Name of depositary institution
Korean Culture Center of Microorganisms (KCCM)

Address of depositary institution *(including postal code and country)*
Yurim Building, Hongjenae-2ga-gil 45, Seodaemun-Gu, Seoul, 120-091, Republic of Korea

| Date of deposit | Accession Number |
|---|---|
| June 23, 2016 | KCCM11848P |

C. ADDITIONAL INDICATIONS *(leave blank if not applicable)*   This information is continued on an additional sheet ☐

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July 1998; reprint January 2004)

The invention claimed is:

1. A method for producing D-psicose comprising contacting a psicose-6-phosphate phosphatase, a microorganism expressing the psicose-6-phosphate phosphatase or a culture of the microorganism expressing the psicose-6-phosphate phosphatase with D-psicose-6-phosphate to convert the D-psicose-6-phosphate to D-psicose;

wherein the psicose-6-phosphate phosphatase comprises:
   i) a motif A comprising at least one sequence selected from the group consisting of SEQ ID NOS: 79, 80, 81, 82, 83, 84, 85, 86, 87, 88, 89, 90, and 91;
   ii) a motif B comprising a sequence having at least 90% sequence identity to at least one sequence selected from the group consisting of SEQ ID NOS: 92, 93, 94, 95, 96, 97, 98, 99, 100, 101, 102, 103, 104, 105, 106, 107, and 108; and
   iii) A remainder sequence comprising remainder having at least 85% sequence identity to the amino acids sequence other than motif A and/or motif B in any sequence selected from the group consisting of SEQ ID NOS: 1, 2, 3, 4, 5, 6, 7, 8, 9, 10, 11, 12, 13, 14, 15, 16, 17, 18, 19 and 20.

2. The method according to claim 1, further comprising, prior to the conversion of D-psicose-6-phosphate to D-psicose, contacting a D-fructose-6-phosphate-3-epimerase, a microorganism expressing the D-fructose-6-phosphate-3-epimerase, or a culture of the microorganism expressing the D-fructose-6-phosphate-3-epimerase with D-fructose-6-phosphate to convert the D-fructose-6-phosphate to D-psicose-6-phosphate.

3. The method according to claim 1, further comprising, prior to the conversion of D-fructose-6-phosphate to D-psicose-6-phosphate, contacting a D-glucose-6-phosphate-isomerase, a microorganism expressing the D-glucose-6-phosphate-isomerase, or a culture of the microorganism expressing the D-glucose-6-phosphate-isomerase with D-glucose-6-phosphate to convert the D-glucose-6-phosphate to D-fructose-6-phosphate.

4. The method according to claim 3, further comprising, prior to the conversion of D-glucose-6-phosphate to D-fructose-6-phosphate, contacting a phosphoglucomutase, a microorganism expressing the phosphoglucomutase, or a culture of the microorganism expressing the phosphoglucomutase with D-glucose-1-phosphate to convert the D-glucose-1-phosphate to D-glucose-6-phosphate.

5. The method according to claim 4, further comprising, prior to the conversion of D-glucose-6-phosphate to D-fructose-6-phosphate, contacting a glucokinase, a microorganism expressing the glucokinase, or a culture of the microorganism expressing the glucokinase and a phosphate with glucose to convert the glucose to D-glucose-6-phosphate.

6. The method according to claim 5, further comprising, prior to the conversion of D-glucose-1-phosphate to D-glucose-6-phosphate, contacting (a) an α-glucan phosphorylase, a starch phosphorylase, a maltodextrin phosphorylase or a sucrose phosphorylase, (b) a microorganism expressing the α-glucan phosphorylase, the starch phosphorylase, the maltodextrin phosphorylase or the sucrose phosphorylase, or (c) a culture of the microorganism expressing the α-glucan phosphorylase, the starch phosphorylase, the maltodextrin phosphorylase or the sucrose phosphorylase, and a phosphate with starch, maltodextrin, sucrose or a combination thereof to convert the starch, maltodextrin, sucrose or combination thereof to D-glucose-1-phosphate.

7. The method according to claim 5, further comprising, prior to the conversion of glucose to D-glucose-6-phosphate, contacting an α-amylase, a pullulanase, a glucoamylase, a sucrase or an isoamylase, (b) a microorganism expressing the α-amylase, pullulanase, glucoamylase, sucrase or isoamylase, or (c) a culture of the microorganism expressing the α-amylase, the pullulanase, the glucoamylase, the sucrase or the isoamylase with starch, maltodextrin, sucrose or a combination thereof to convert the starch, maltodextrin, sucrose or combination thereof to glucose.

8. A method for producing D-psicose comprising contacting (a) enzymes of (i) a psicose-6-phosphate phosphatase, (ii) a D-fructose-6-phosphate-3-epimerase, (iii) a D-glucose-6-phosphate-isomerase, (iv) a phosphoglucomutase or a glucokinase and (v) one or more selected from the group consisting of an α-glucan phosphorylase, a starch phosphorylase, a maltodextrin phosphorylase, a sucrose phosphorylase, an α-amylase, a pullulanase, an isoamylase, a glucoamylase and a sucrase, (b) microorganisms expressing the enzymes listed in (a), or (c) a culture of microorganisms expressing the enzymes listed in (a) with (i) one or more selected from the group consisting of starch, maltodextrin, and sucrose, and (ii) a phosphate wherein the psicose-6-phosphate phosphatase comprises:
  i) a motif A comprising at least one sequence selected from the group consisting of SEQ ID NOS: 79, 80, 81, 82, 83, 84, 85, 86, 87, 88, 89, 90, and 91;
  ii) a motif B comprising a sequence having at least 90% sequence identity to at least one sequence selected from the group consisting of SEQ ID NOS: 92, 93, 94, 95, 96, 97, 98, 99, 100, 101, 102, 103, 104, 105, 106, 107, and 108; and
  iii) A remainder sequence comprising remainder having at least 85% sequence identity to the amino acids sequence other than motif A and/or motif B in any sequence selected from the group consisting of SEQ ID NOS: 1, 2, 3, 4, 5, 6, 7, 8, 9, 10, 11, 12, 13, 14, 15, 16, 17, 18, 19 and 20.

9. The method according to claim 1, wherein the contact reaction is carried out at a pH of 5.0 to 9.0, at a temperature of 40° C. to 80° C. and/or for 2 hours to 24 hours.

10. The method of producing D-psicose according to claim 1, wherein the psicose-6-phosphate phosphatase consists of the amino acid sequence set forth in SEQ ID NO: 1, 2, 3, 4, 5, 6, 7, 8, 9, 10, 11, 12, 13, 14, 15, 16, 17, 18, 19 or 20.

11. The method of producing D-psicose according to claim 1, wherein the psicose-6-phosphate phosphatase comprises an amino acid sequence comprising:
  i. the motif A comprising a sequence of SEQ ID No: 79, the motif B comprising a sequence having at least 90% sequence identity to SEQ ID NO: 92, and the sequence comprising the remainder having at least 85% sequence identity to amino acids sequence other than motif A and/or motif B in SEQ ID NO: 1;
  ii. the motif A comprising a sequence of SEQ ID No: 79, the motif B comprising a sequence having at least 90% sequence identity to SEQ ID NO: 93, and the sequence comprising the remainder having at least 85% sequence identity to amino acids sequence other than motif A and/or motif B in SEQ ID NO: 2;
  iii. the motif A comprising a sequence of SEQ ID No: 80, the motif B comprising a sequence having at least 90% sequence identity to SEQ ID NO: 94, and the sequence comprising the remainder having at least 85% sequence identity to amino acids sequence other than motif A and/or motif B in SEQ ID NO: 3;
  iv. the motif A comprising a sequence of SEQ ID No: 80, the motif B comprising a sequence having at least 90% sequence identity to SEQ ID NO: 95, and the sequence comprising the remainder having at least 85% sequence identity to amino acids sequence other than motif A and/or motif B in SEQ ID NO: 4;
  V. the motif A comprising a sequence of SEQ ID No: 81, the motif B comprising a sequence having at least 90% sequence identity to SEQ ID NO: 96, and the sequence comprising the remainder having at least 85% sequence identity to amino acids sequence other than motif A and/or motif B in SEQ ID NO: 5;
  vi. the motif A comprising a sequence of SEQ ID No: 82, the motif B comprising a sequence having at least 90% sequence identity to SEQ ID NO: 97, and the sequence comprising the remainder having at least 85% sequence identity to amino acids sequence other than motif A and/or motif B in SEQ ID NO: 6;
  vii. the motif A comprising a sequence of SEQ ID No: 83, the motif B comprising a sequence having at least 90% sequence identity to SEQ ID NO: 98, and the amino acids sequence comprising the remainder having at least 85% sequence identity to sequence other than motif A and/or motif B in SEQ ID NO: 7;
  viii. the motif A comprising a sequence of SEQ ID No: 84, the motif B comprising a sequence having at least 90% sequence identity to SEQ ID NO: 99, and the sequence comprising the remainder having at least 85% sequence identity to amino acids sequence other than motif A and/or motif B in SEQ ID NO: 8;
  ix. the motif A comprising a sequence of SEQ ID No: 85, the motif B comprising a sequence having at least 90% sequence identity to SEQ ID NO: 100, and the sequence comprising the remainder having at least 85% sequence identity to amino acids sequence other than motif A and/or motif B in SEQ ID NO: 9;
  x. the motif A comprising a sequence of SEQ ID No: 86, the motif B comprising a sequence having at least 90% sequence identity to SEQ ID NO: 101, and the sequence comprising the remainder having at least 85% sequence identity to amino acids sequence other than motif A and/or motif B in SEQ ID NO: 10;

xi. the motif A comprising a sequence of SEQ ID No: 87, the motif B comprising a sequence having at least 90% sequence identity to SEQ ID NO: 102, and the sequence comprising the remainder having at least 85% sequence identity to amino acids sequence other than motif A and/or motif B in SEQ ID NO: 11;

xii. the motif A comprising a sequence of SEQ ID No: 88, the motif B comprising a sequence having at least 90% sequence identity to SEQ ID NO: 103, and the sequence comprising the remainder having at least 85% sequence identity to amino acids sequence other than motif A and/or motif B in SEQ ID NO: 12;

xiii. the motif A comprising a sequence of SEQ ID No: 89, the motif B comprising a sequence having at least 90% sequence identity to SEQ ID NO: 104, and the sequence comprising the remainder having at least 85% sequence identity to amino acids sequence other than motif A and/or motif B in SEQ ID NO: 13;

xiv. the motif A comprising a sequence of SEQ ID No: 90, the motif B comprising a sequence having at least 90% sequence identity to SEQ ID NO: 105, and the sequence comprising the remainder having at least 85% sequence identity to amino acids sequence other than motif A and/or motif B in SEQ ID NO: 14;

xv. the motif A comprising a sequence of SEQ ID No: 91, the motif B comprising a sequence having at least 90% sequence identity to SEQ ID NO: 106, and the sequence comprising the remainder having at least 85% sequence identity to amino acids sequence other than motif A and/or motif B in SEQ ID NO: 15;

xvi. the motif A comprising a sequence of SEQ ID No: 80, the motif B comprising a sequence having at least 90% sequence identity to SEQ ID NO: 107, and the sequence comprising the remainder having at least 85% sequence identity to amino acids sequence other than motif A and/or motif B in SEQ ID NO: 16;

xvii. the motif A comprising a sequence of SEQ ID No: 80, the motif B comprising a sequence having at least 90% sequence identity to SEQ ID NO: 107, and the sequence comprising the remainder having at least 85% sequence identity to amino acids sequence other than motif A and/or motif B in SEQ ID NO: 17;

xviii. the motif A comprising a sequence of SEQ ID No: 80, the motif B comprising a sequence having at least 90% sequence identity to SEQ ID NO: 94, and the sequence comprising the remainder having at least 85% sequence identity to amino acids sequence other than motif A and/or motif B in SEQ ID NO: 18;

xix. the motif A comprising a sequence of SEQ ID No: 80, the motif B comprising a sequence having at least 90% sequence identity to SEQ ID NO: 98, and the sequence comprising the remainder having at least 85% sequence identity to amino acids sequence other than motif A and/or motif B in SEQ ID NO: 19; or xx. the motif A comprising a sequence of SEQ ID No: 80, the motif B comprising a sequence having at least 90% sequence identity to SEQ ID NO: 108, and the sequence comprising the remainder having at least 85% sequence identity to amino acids sequence other than motif A and/or motif B in SEQ ID NO: 20.

12. The method of producing D-psicose according to claim 8, wherein the psicose-6-phosphate phosphatase comprises an amino acid sequence comprising:

i. the motif A comprising a sequence of SEQ ID No: 79, the motif B comprising a sequence having at least 90% sequence identity to SEQ ID NO: 92, and the sequence comprising the remainder having at least 85% sequence identity to amino acids sequence other than motif A and/or motif B in SEQ ID NO: 1;

ii. the motif A comprising a sequence of SEQ ID No: 79, the motif B comprising a sequence having at least 90% sequence identity to SEQ ID NO: 93, and the sequence comprising the remainder having at least 85% sequence identity to amino acids sequence other than motif A and/or motif B in SEQ ID NO: 2;

iii. the motif A comprising a sequence of SEQ ID No: 80, the motif B comprising a sequence having at least 90% sequence identity to SEQ ID NO: 94, and the sequence comprising the remainder having at least 85% sequence identity to amino acids sequence other than motif A and/or motif B in SEQ ID NO: 3;

iv. the motif A comprising a sequence of SEQ ID No: 80, the motif B comprising a sequence having at least 90% sequence identity to SEQ ID NO: 95, and the sequence comprising the remainder having at least 85% sequence identity to amino acids sequence other than motif A and/or motif B in SEQ ID NO: 4;

V. the motif A comprising a sequence of SEQ ID No: 81, the motif B comprising a sequence having at least 90% sequence identity to SEQ ID NO: 96, and the sequence comprising the remainder having at least 85% sequence identity to amino acids sequence other than motif A and/or motif B in SEQ ID NO: 5;

vi. the motif A comprising a sequence of SEQ ID No: 82, the motif B comprising a sequence having at least 90% sequence identity to SEQ ID NO: 97, and the sequence comprising the remainder having at least 85% sequence identity to amino acids sequence other than motif A and/or motif B in SEQ ID NO: 6;

vii. the motif A comprising a sequence of SEQ ID No: 83, the motif B comprising a sequence having at least 90% sequence identity to SEQ ID NO: 98, and the sequence comprising the remainder having at least 85% sequence identity to amino acids sequence other than motif A and/or motif B in SEQ ID NO: 7;

viii. the motif A comprising a sequence of SEQ ID No: 84, the motif B comprising a sequence having at least 90% sequence identity to SEQ ID NO: 99, and the sequence comprising the remainder having at least 85% sequence identity to amino acids sequence other than motif A and/or motif B in SEQ ID NO: 8;

ix. the motif A comprising a sequence of SEQ ID No: 85, the motif B comprising a sequence having at least 90% sequence identity to SEQ ID NO: 100, and the sequence comprising the remainder having at least 85% sequence identity to amino acids sequence other than motif A and/or motif B in SEQ ID NO: 9;

x. the motif A comprising a sequence of SEQ ID No: 86, the motif B comprising a sequence having at least 90% sequence identity to SEQ ID NO: 101, and the sequence comprising the remainder having at least 85% sequence identity to amino acids sequence other than motif A and/or motif B in SEQ ID NO: 10;

xi. the motif A comprising a sequence of SEQ ID No: 87, the motif B comprising a sequence having at least 90% sequence identity to SEQ ID NO: 102, and the sequence comprising the remainder having at least 85% sequence identity to amino acids sequence other than motif A and/or motif B in SEQ ID NO: 11;

xii. the motif A comprising a sequence of SEQ ID No: 88, the motif B comprising a sequence having at least 90% sequence identity to SEQ ID NO: 103, and the sequence comprising the remainder having at least 85% sequence identity to amino acids sequence other than motif A and/or motif B in SEQ ID NO: 12;

xiii. the motif A comprising a sequence of SEQ ID No: 89, the motif B comprising a sequence having at least 90% sequence identity to SEQ ID NO: 104, and the sequence comprising remainder having at least 85% sequence identity to amino acids sequence other than motif A and/or motif B in SEQ ID NO: 13;

xiv. the motif A comprising a sequence of SEQ ID No: 90, the motif B comprising a sequence having at least 90% sequence identity to SEQ ID NO: 105, and the sequence comprising the remainder having at least 85% sequence identity to amino acids sequence other than motif A and/or motif B in SEQ ID NO: 14;

xv. the motif A comprising a sequence of SEQ ID No: 91, the motif B comprising a sequence having at least 90% sequence identity to SEQ ID NO: 106, and the sequence comprising the remainder having at least 85% sequence identity to amino acids sequence other than motif A and/or motif B in SEQ ID NO: 15;

xvi. the motif A comprising a sequence of SEQ ID No: 80, the motif B comprising a sequence having at least 90% sequence identity to SEQ ID NO: 107, and the sequence comprising the remainder having at least 85% sequence identity to amino acids sequence other than motif A and/or motif B in SEQ ID NO: 16;

xvii. the motif A comprising a sequence of SEQ ID No: 80, the motif B comprising a sequence having at least 90% sequence identity to SEQ ID NO: 107, and the sequence comprising the remainder having at least 85% sequence identity to amino acids sequence other than motif A and/or motif B in SEQ ID NO: 17;

xviii. the motif A comprising a sequence of SEQ ID No: 80, the motif B comprising a sequence having at least 90% sequence identity to SEQ ID NO: 94, and the sequence comprising the remainder having at least 85% sequence identity to amino acids sequence other than motif A and/or motif B in SEQ ID NO: 18;

xix. the motif A comprising a sequence of SEQ ID No: 80, the motif B comprising a sequence having at least 90% sequence identity to SEQ ID NO: 98, and the sequence comprising the remainder having at least 85% sequence identity to amino acids sequence other than motif A and/or motif B in SEQ ID NO: 19; or xx. the motif A comprising a sequence of SEQ ID No: 80, the motif B comprising a sequence having at least 90% sequence identity to SEQ ID NO: 108, and the sequence comprising the remainder having at least 85% sequence identity to amino acids sequence other than motif A and/or motif B in SEQ ID NO: 20.

13. The method according to claim 1, wherein the psicose-6-phosphate phosphatase is encoded by a nucleotide sequence set forth as SEQ ID NO: 21, 22, 23, 24, 25, 26, 27, 28, 29, 30, 31, 32, 33, 34, 35, 36, 37, 38, 39 or 40.

14. The method according to claim 8, wherein the psicose-6-phosphate phosphatase consists of the amino acid sequence set forth as SEQ ID NO: 1, 2, 3, 4, 5, 6, 7, 8, 9, 10, 11, 12, 13, 14, 15, 16, 17, 18, 19 or 20.

15. The method according to claim 8, wherein the psicose-6-phosphate phosphatase is encoded by a nucleotide sequence set forth as SEQ ID NO: 21, 22, 23, 24, 25, 26, 27, 28, 29, 30, 31, 32, 33, 34, 35, 36, 37, 38, 39 or 40.

\* \* \* \* \*

SEQUENCE LISTING

<160> NUMBER OF SEQ ID NOS: 108

<210> SEQ ID NO 1
<211> LENGTH: 272
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Rhodothermus marinus

<400> SEQUENCE: 1

```
Met Met Asp Ala Tyr Thr Leu Tyr Glu Glu Ala Arg Glu Val Ala Ala
1               5                   10                  15

Arg Leu Ala Arg Asp Ala Gly Gln Ile Ala Arg Tyr Tyr Ala Gly Arg
            20                  25                  30

Val Thr Val Arg Glu Lys Gly Tyr Asn Glu Leu Val Thr Gln Ala Asp
        35                  40                  45

Glu Glu Val Gln Arg Phe Leu Ile Glu Gln Ile His Arg His Phe Pro
    50                  55                  60

Glu His Ala Ile Leu Ala Glu Glu Asn Leu Ser Asp Met Gln Asp Gly
65                  70                  75                  80

Arg Glu Gly Ala Ser Phe Arg Trp Ile Ile Asp Pro Ile Asp Gly Thr
                85                  90                  95

Thr Asn Phe Thr His Gly Val Pro Pro Tyr Gly Ile Ser Leu Ala Leu
            100                 105                 110

Gln His Glu Gly Arg Thr Val Val Gly Val Val Tyr Asp Val Pro His
        115                 120                 125

Asp Glu Leu Phe Thr Ala Val Arg Gly Gly Leu Tyr Val Asn Gly
    130                 135                 140

Val Arg Ala Arg Val Ser Gln Thr Glu Thr Leu Arg Glu Ala Leu Ile
145                 150                 155                 160

Thr Thr Gly Phe Pro Tyr Arg Glu Val Val His Leu Glu Glu Tyr Leu
                165                 170                 175

Glu Ala Leu Gly Arg Val Ile Arg Ala Thr Arg Gly Val Arg Arg Pro
            180                 185                 190

Gly Ala Ala Ser Val Asp Leu Ala Trp Val Ala Cys Gly Arg Phe Asp
        195                 200                 205

Gly Phe Phe Glu Thr Gly Leu Ser Pro Trp Asp Val Ala Ala Gly Ile
    210                 215                 220

Leu Leu Val Glu Glu Gly Gly Gly Arg Val Thr Asp Phe His Gly Arg
225                 230                 235                 240

Pro Asp Pro Ile Phe Ala Arg Gln Met Leu Ala Thr Asn Gly Arg Ile
                245                 250                 255

His Glu Ala Leu Cys Glu Leu Val Ala Pro Leu His His Val Tyr Ala
            260                 265                 270
```

<210> SEQ ID NO 2
<211> LENGTH: 255
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Thermotoga lettingae

<400> SEQUENCE: 2

```
Met Asp Arg Met Asp Phe Ser Ile Lys Ile Ala Arg Lys Val Gly Leu
1               5                   10                  15
```

Tyr Leu Met Glu His Trp Gly Asn Ala Glu Asn Val Arg Gln Lys Ser
            20                  25                  30

Ser Phe Gln Asp Leu Val Ser Asp Cys Asp Lys Gln Ala Gln Lys Met
        35                  40                  45

Ile Val Gln Lys Ile Lys Asp His Phe Pro Asp Ala Ile Leu Ala
    50                  55                  60

Glu Gly Leu Phe Glu Lys Gly Asp Arg Met Trp Ile Ile Asp Pro
65                  70                  75                  80

Ile Asp Gly Thr Met Asn Tyr Val His Gly Leu Pro Ser Phe Ala Ile
                85                  90                  95

Gly Ile Ala Tyr Val Lys Glu Gln Val Ile Leu Gly Val Ala His
            100                 105                 110

Asp Pro Val Leu Asn Glu Thr Tyr Tyr Ala Ile Lys Gly Gln Gly Ala
        115                 120                 125

Tyr Lys Asn Gly Glu Arg Ile Asn Val Ser Glu Asn Ser Leu Leu Lys
130                 135                 140

Asp Ser Ile Gly Asn Thr Gly Phe Tyr Thr Asp Phe Thr Gly Ile Phe
145                 150                 155                 160

Ile Ser Ala Ile Glu Lys Lys Val Arg Arg Val Arg Met Thr Gly Ser
                165                 170                 175

Ala Ile Leu Ala Gly Ala Tyr Val Ala Cys Gly Arg Phe Asp Phe Phe
            180                 185                 190

Ile Ala Lys Arg Ala Asn Ser Trp Asp Val Ala Pro Leu Phe Val Leu
        195                 200                 205

Val Pro Glu Ala Gly Gly Ile Val Thr Asp Leu Ser Gly Asn Gln Ala
    210                 215                 220

His Leu Asn Thr Gly Asn Phe Leu Phe Ser Asn Gly Leu Leu His Asp
225                 230                 235                 240

Gln Val Leu Glu Val Ile Arg Glu Val Asn Lys Lys Val Arg Lys
                245                 250                 255

<210> SEQ ID NO 3
<211> LENGTH: 258
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Meiothermus ruber

<400> SEQUENCE: 3

Met Asp Leu Arg Ala Tyr Leu Gln Thr Ala Leu Asp Ala Ala Tyr Leu
1               5                   10                  15

Ala Lys Gly Ile His Gln Tyr Tyr Gln Glu Lys Gly Phe Thr Gln Ser
            20                  25                  30

Thr Lys Ser Thr Pro Thr Asp Leu Val Thr Gln Ala Asp His Glu Ser
        35                  40                  45

Glu Ala Ala Ile Arg Glu Leu Ile Ala Ser Arg His Pro Asp His Val
    50                  55                  60

Val Leu Gly Glu Glu Gln Gly Gln Asp Lys Glu Gly Ala Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Gly Leu Glu Ala His Gly Glu Val Val Leu
            100                 105                 110

```
Gly Val Val Leu Asp Thr Ala Arg Gly Glu Leu Phe Thr Ala Thr Lys
            115                 120                 125

Gly Gly Gly Ala Tyr Leu Asn Gly Arg Pro Ile Arg Val Ser Thr Arg
        130                 135                 140

Ser Thr Leu Val Gly Ser Leu Leu Ala Thr Gly Phe Pro Tyr Asp Val
145                 150                 155                 160

Ser Lys Asp Thr Glu Asn Leu Val Tyr Phe Gln Arg Ala Leu Thr Lys
                165                 170                 175

Gly Leu Met Val Arg Arg Pro Gly Ala Ala Leu Asp Leu Ala Tyr
                180                 185                 190

Val Ala Ala Gly Arg Leu Asp Gly Phe Trp Glu Val Lys Leu Asn Pro
                195                 200                 205

Trp Asp Val Ala Ala Gly Trp Leu Ile Val Ser Glu Ala Gly Gly Arg
            210                 215                 220

Ile Thr Gly Leu Gln Gly Glu Asp Tyr Arg Leu Gly Asn Arg Tyr Leu
225                 230                 235                 240

Val Ala Ser Asn Gly Leu Ile His Gly Pro Leu Leu Asp Thr Ile His
                245                 250                 255

Gly Arg

<210> SEQ ID NO 4
<211> LENGTH: 265
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Dictyoglomus turgidum

<400> SEQUENCE: 4

Met Lys Arg Ile Leu Glu Val Ala Ile Lys Thr Ile Lys Glu Ser Gly
1               5                   10                  15

Asn Ile Leu Leu Asn Tyr Ile Gly Glu Glu Lys Glu Ile Glu Leu Lys
                20                  25                  30

Gly Ile Ser Asn Leu Val Thr Gln Val Asp Lys Leu Ser Glu Arg His
            35                  40                  45

Ile Leu Lys Ser Ile Glu Glu Asn Phe Pro Asp His Ser Ile Leu Thr
50                  55                  60

Glu Glu Thr Gly Phe Ile Asn Lys Asn Ser Glu Tyr Thr Trp Ile Val
65                  70                  75                  80

Asp Pro Leu Asp Gly Thr Thr Asn Tyr Ala His Asn Phe Pro Phe Phe
                85                  90                  95

Gly Ile Ser Ile Ala Leu Ile Lys Asn Lys Glu Ile Ile Leu Gly Leu
            100                 105                 110

Ile Tyr Asp Pro Ile Arg Asp Glu Leu Phe Tyr Ala Ile Lys Asn Glu
        115                 120                 125

Gly Ala Tyr Leu Asn Asp Arg Arg Ile Glu Val Ser Lys Thr Glu Ser
    130                 135                 140

Leu Glu Asn Ser Leu Ile Ser Phe Ala Phe Pro Tyr Glu Leu Ser Leu
145                 150                 155                 160

Glu Glu Lys Asn Phe Ile Pro Phe Ile Asn Phe Ser Ser Arg Thr His
                165                 170                 175

Gly Ile Arg Arg Thr Gly Ser Ala Ala Ile Glu Ile Ala Tyr Val Gly
            180                 185                 190

Cys Gly Arg Leu Asp Gly Phe Trp Ala Lys Lys Leu Lys Pro Trp Asp
        195                 200                 205
```

Ile Ser Ala Gly Ile Leu Ile Val Glu Glu Ala Lys Gly Lys Val Thr
    210                 215                 220

Asp Phe Ser Gly Asn Asn Ile Asp Ile His Thr Asp Asn Ile Leu Phe
225                 230                 235                 240

Ser Asn Gly Lys Ile His Gln Glu Met Ile Lys Ile Leu Asn Leu Gly
            245                 250                 255

Lys Ile Phe Ile Arg Asn Glu Lys Phe
            260                 265

<210> SEQ ID NO 5
<211> LENGTH: 251
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositiol-mono-
      phosphatase from Pyrobaculum ferrireducens

<400> SEQUENCE: 5

Met Leu Gly Val Leu Glu Ala Val Ala Val Arg Ala Ser His Phe Leu
1               5                   10                  15

Met Glu Tyr Phe Arg Ala Gly Arg Gly Val Asp Val Val Ser Arg Lys
            20                  25                  30

Glu Asp Asp Val Thr Arg Glu Val Asp Ile Ala Ala Glu Thr Leu Ile
        35                  40                  45

Tyr Lys Met Leu Arg Glu Ala Phe Lys Glu Gly Val Leu Tyr Ala
    50                  55                  60

Glu Glu Gly Gly Ile Tyr Arg Trp Gly Asp Glu Arg Tyr Ile Phe Val
65                  70                  75                  80

Leu Asp Pro Leu Asp Gly Ser Leu Asn Tyr Ala Val Gly Val Pro Phe
                85                  90                  95

Phe Ala Val Ser Ile Ala Ala Gly Lys His Arg Glu Gly Thr Leu Ala
            100                 105                 110

Asp Leu Glu Tyr Ala Val Val Ala Ile Pro Pro Thr Gly Asp Val Tyr
        115                 120                 125

Thr Ala Ala Pro Gly Val Gly Ala Arg Lys Asn Gly Lys Pro Leu Arg
    130                 135                 140

Arg Thr Pro Arg Ser Asn Ile Val Phe Val Ala Val Ser Asn Ser Phe
145                 150                 155                 160

Pro Pro Lys Thr Cys Glu Val Val Arg Arg Leu Gly Leu Arg Gly Arg
                165                 170                 175

Ser Leu Gly Ser Ser Ala Ala Glu Leu Ala Tyr Thr Val Glu Gly Ile
            180                 185                 190

Ala Arg Gly Phe Leu Asp Leu Arg Gly Lys Leu Arg Leu Leu Asp Val
        195                 200                 205

Ala Gly Ala Leu Thr Ile Gly Lys Tyr Val Asp Gly Phe Arg Tyr Val
    210                 215                 220

Val Met Gly Asp Thr Lys Pro His Ser Lys Val Ser Leu Val Ala Gly
225                 230                 235                 240

Asp Val Asp Phe Val Asn Ala Ala Thr Thr Asp
                245                 250

<210> SEQ ID NO 6
<211> LENGTH: 257
<212> TYPE: PRT
<213> ORGANISM: Artificial Sequence
<220> FEATURE:

<223> OTHER INFORMATION: Protein having the activity of psicose-6-
phosphate phosphatase Amino acid sequence of inositol-mono-
phosphatase from Thermoanaerobacter wiegelii

<400> SEQUENCE: 6

```
Met Lys Asp Glu Lys Gly Ile Val Val Asp Ile Ile Lys Lys Ala Gly
1               5                   10                  15

Glu Ile Leu Gln Asp Gly Trp Asn Lys Lys Asn Phe Lys Ile Tyr Arg
            20                  25                  30

Lys Gly Thr Ile Asn Leu Val Thr Glu Ile Asp Lys Lys Ile Glu Phe
        35                  40                  45

Leu Ile Ile Gln Leu Leu Lys Gln Tyr Phe Pro Asp Tyr Gly Ile Leu
    50                  55                  60

Thr Glu Glu Ser Lys Glu Ile Asn Ser Lys Ala Asn Val Arg Trp Ile
65                  70                  75                  80

Ile Asp Pro Leu Asp Gly Thr Thr Asn Tyr Ile Lys Gln Tyr Pro Phe
                85                  90                  95

Val Ala Ile Ser Ile Ala Leu Glu Lys Glu Gly Glu Leu Ile Leu Gly
            100                 105                 110

Val Val Tyr Asn Pro Ile Leu Asn Glu Met Phe Ile Ala Gln Lys Gly
        115                 120                 125

Cys Gly Ala Thr Tyr Asn Gly Lys Ser Ile His Val Ser Lys Ile Lys
    130                 135                 140

Glu Leu Gly Ser Ala Val Leu Ala Ser Gly Phe Pro Tyr Asp Ala Trp
145                 150                 155                 160

Glu Asn Pro Asp Asn Asn Ala Lys Gln Trp Arg Gln Phe Leu Thr Arg
                165                 170                 175

Ser Leu Ser Leu Arg Cys Asp Gly Ser Ala Ala Leu Asp Leu Cys Arg
            180                 185                 190

Val Ala Cys Gly Gln Leu Asp Gly Tyr Trp Glu Lys Gly Ile Ser Pro
        195                 200                 205

Trp Asp Val Ala Ala Gly Ile Val Ile Leu Arg Glu Ala Gly Gly Ile
    210                 215                 220

Ile Thr Asp Tyr Leu Gly Glu Glu Asn Phe Phe Lys Arg Gly Glu Val
225                 230                 235                 240

Val Ala Ala Asn Pro Val Leu His Ala Gln Met Leu Lys Val Leu Asn
                245                 250                 255

Asn
```

<210> SEQ ID NO 7
<211> LENGTH: 264
<212> TYPE: PRT
<213> ORGANISM: Artificial Sequence
<220> FEATURE:
<223> OTHER INFORMATION: Protein having the activity of psicose-6-
phosphate phosphatase Amino acid sequence of inositol-mono-
phosphatase from Thermus thermophilus

<400> SEQUENCE: 7

```
Met Ile Gly Arg Arg His Pro Tyr Tyr Pro Tyr Leu Glu Ala Ala Leu
1               5                   10                  15

Glu Ala Ala Ser Leu Ala Arg Gly Ile His Leu Tyr Tyr Leu Glu Lys
            20                  25                  30

Gly Phe Thr Glu Gly Thr Lys Ser Gly Pro Thr Asp Leu Val Thr Gln
        35                  40                  45

Ala Asp Arg Glu Ala Glu Glu Ala Val Lys Gly Leu Leu Leu Ser Arg
    50                  55                  60
```

Phe Pro Glu Ala Gly Phe Leu Gly Glu Glu Gly Ser Glu Gly Gly
65                  70                  75                  80

Lys Ala Leu Arg Phe Ile Val Asp Pro Leu Asp Gly Thr Val Asn Tyr
            85                  90                  95

Ala His Gly Phe Pro Phe Phe Ala Val Ser Ile Ala Leu Glu Ala Glu
                100                 105                 110

Gly Ala Ile Gln Met Gly Val Val Met Asp Thr Ala Arg Gly Glu Val
            115                 120                 125

Phe Tyr Ala Leu Arg Gly Gly Ala Tyr Leu Asn Gly Arg Pro Ile
130                 135                 140

Arg Val Thr Gly Arg Glu Ser Leu Val Gly Ser Leu Leu Ala Thr Gly
145                 150                 155                 160

Phe Pro Tyr Asp Val Ala Lys Asp Pro Glu Asn Leu Thr Tyr Phe Glu
                165                 170                 175

Arg Ala Leu Gly Lys Gly Leu Leu Val Arg Arg Pro Gly Ala Ala Ala
            180                 185                 190

Leu Asp Leu Ala Tyr Val Ala Ala Gly Arg Leu Glu Gly Phe Trp Glu
            195                 200                 205

Val Lys Leu Asn Pro Trp Asp Val Ala Ala Gly Trp Leu Leu Val Glu
210                 215                 220

Glu Ala Gly Gly Arg Val Thr Asp Leu Glu Gly Asn Pro Tyr Arg Leu
225                 230                 235                 240

Gly Ser Arg Tyr Ile Leu Ala Thr Asn Gly Arg Val His Glu Ala Leu
                245                 250                 255

Arg Arg Thr Leu Leu Gly Leu Asp
            260

<210> SEQ ID NO 8
<211> LENGTH: 251
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Thermococcus litoralis

<400> SEQUENCE: 8

Met Tyr Glu Trp Asn Glu Ile Ala Leu Asn Leu Ala Lys Asp Ile Glu
1               5                   10                  15

Arg Glu Val Met Pro Leu Phe Gly Thr Lys Lys Ala Gly Glu Phe Ile
            20                  25                  30

Gly Phe Ser Pro Ser Gly Asp Lys Thr Lys Leu Val Asp Lys Val Ala
        35                  40                  45

Glu Asp Val Val Leu Glu Tyr Leu Arg Pro Leu Gly Val Asn Val Val
    50                  55                  60

Ser Glu Glu Ile Gly Asn Ile Glu Ala Gly Ser Glu Tyr Thr Ile Val
65                  70                  75                  80

Val Asp Pro Ile Asp Gly Ser Phe Asn Phe Ile Gln Gly Ile Pro Ile
                85                  90                  95

Phe Gly Phe Ser Phe Ala Val Phe Lys Asn Glu Lys Pro Val Tyr Ala
                100                 105                 110

Met Ile Tyr Glu Phe Ile Thr Lys Asn Val Tyr Glu Gly Ile Pro Gly
            115                 120                 125

Glu Gly Ala Tyr Leu Asn Gly Glu Arg Ile Arg Val Arg His Leu Asn
    130                 135                 140

Glu Lys Ser Ile Ser Ile Ser Phe Tyr Thr Arg Gly Arg Gly Ala Arg
145                 150                 155                 160

Leu Val Glu Lys Val Lys Arg Thr Arg Val Leu Gly Ala Ile Ala Val
            165                 170                 175

Glu Leu Ala Tyr Leu Ala Arg Gly Ser Leu Asp Gly Val Ile Asp Ile
            180                 185                 190

Arg Asn Tyr Val Arg Pro Thr Asp Ile Ala Ala Gly Tyr Ile Ile Ala
            195                 200                 205

Lys Glu Ala Gly Ala Ile Ile Thr Asp Asp Ser Gly Glu Glu Ile Lys
            210                 215                 220

Phe Arg Leu Asp Ala Arg Glu Lys Leu Asn Ile Ile Ala Val Asn Asp
225                 230                 235                 240

Lys Arg Leu Leu Lys Leu Ile Leu Glu Val Ile
            245                 250

<210> SEQ ID NO 9
<211> LENGTH: 264
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Geobacillus stearothermophilus

<400> SEQUENCE: 9

Met Ala Glu Lys Trp Glu Glu Ile Asp Arg Tyr Ala Arg Gln Trp Ile
1               5                   10                  15

Asp Glu Ala Gly Lys Arg Ile Arg Ala Ser Phe Ala Lys Gln Leu Thr
            20                  25                  30

Val Glu Ala Lys Glu Asn Pro Asn Asp Leu Val Thr Asn Val Asp Arg
        35                  40                  45

Ala Ile Glu Gln Phe Phe Ala Glu His Ile Arg Arg Gln Phe Pro Ser
    50                  55                  60

His Arg Leu Leu Gly Glu Glu Gly Phe Gly Asp Arg Ile Asp Ala Leu
65                  70                  75                  80

Asp Gly Val Val Trp Val Ile Asp Pro Ile Asp Gly Thr Met Asn Phe
                85                  90                  95

Val His Gln Arg Arg His Phe Ala Val Ser Ile Gly Ile Phe Glu Asp
            100                 105                 110

Gly Ile Gly Gln Leu Gly Tyr Val Tyr Asp Val Val Phe Asp Glu Leu
        115                 120                 125

Tyr Ala Ala Gln Lys Gly Arg Gly Val Phe Leu Asn Gly Glu Pro Leu
    130                 135                 140

Gly Leu Leu Gln Pro Ala Pro Val Ala Glu Ser Ile Ile Ala Ile Asn
145                 150                 155                 160

Gly Thr Trp Leu Met Glu Asn Lys Arg Leu Asp His Arg Pro Leu Met
                165                 170                 175

Arg Leu Ala Lys Glu Ala Arg Gly Thr Arg Ser Tyr Gly Ser Ala Ala
            180                 185                 190

Leu Glu Leu Ala Tyr Val Ala Ala Gly Arg Leu Asp Ala Tyr Ile Ser
        195                 200                 205

Pro Arg Leu Ser Pro Trp Asp Phe Ala Gly Gly Met Ile Leu Ile Glu
    210                 215                 220

Glu Ala Gly Gly Met Val Thr Thr Leu Asp Gly Lys Pro Leu Asp Leu
225                 230                 235                 240

Leu Gly Arg Asn Ser Val Leu Ala Ala Lys Pro Gly Val His Glu Glu

```
                        245                 250                 255
Ile Leu Arg Arg Tyr Leu His Asp
            260

<210> SEQ ID NO 10
<211> LENGTH: 259
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Anaerolinea thermophila

<400> SEQUENCE: 10

Met Thr Thr Ser Leu Arg Asp Leu Leu Asp Phe Ala Val Glu Thr Ala
1               5                   10                  15

Tyr Leu Ala Gly Arg Thr Thr Leu Ala Tyr Phe Gln Thr Gly Val Gln
            20                  25                  30

Ala Glu Phe Lys Ala Asp Ser Ser Pro Val Thr Leu Ala Asp Arg Ala
        35                  40                  45

Ala Glu Gln Leu Ile Arg Gln Arg Ile Glu Lys Arg Phe Pro His His
    50                  55                  60

Ala Ile Val Gly Glu Glu Phe Gly Val Gln Gly Ser Ala Asp Ala Thr
65                  70                  75                  80

His Arg Trp Phe Ile Asp Pro Ile Asp Gly Thr Lys Ser Phe Leu Arg
                85                  90                  95

Gly Ile Pro Leu Tyr Ala Val Leu Leu Gly Leu Glu Ile Glu Gly Arg
            100                 105                 110

Val Gln Val Gly Val Ala Tyr Tyr Pro Ala Met Asp Glu Met Leu Ser
        115                 120                 125

Ala Ala Asp Gly Glu Gly Cys Trp Trp Asn Gly Arg Arg Ala Arg Val
    130                 135                 140

Ser Thr Ala Ser Arg Leu Ala Glu Ala Trp Val Thr Ser Thr Asp Pro
145                 150                 155                 160

Tyr Asn Phe Gln Lys Thr Gly Lys Asp Ala Ala Trp Gln Arg Ile Gln
                165                 170                 175

Ala Val Ser Tyr His Arg Gly Gly Trp Gly Asp Ala Tyr Gly Tyr Leu
            180                 185                 190

Leu Val Ala Thr Gly Arg Ala Glu Val Met Leu Asp Pro Ile Met Asn
        195                 200                 205

Glu Trp Asp Cys Ala Pro Phe Pro Pro Ile Phe Arg Glu Ala Gly Gly
    210                 215                 220

Phe Phe Gly Asp Trp Gln Gly Asn Glu Thr Ile Tyr Gly Gly Glu Ala
225                 230                 235                 240

Leu Ala Thr Thr Gln Val Leu Leu Pro Glu Val Leu Glu Cys Leu His
                245                 250                 255

Ser Ser Leu

<210> SEQ ID NO 11
<211> LENGTH: 267
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Sulfolobus acidocaldarius

<400> SEQUENCE: 11
```

-continued

Met Lys Arg Glu Asp Val Glu Lys Val Ala Ser Glu Ala Ser Lys Tyr
1               5                   10                  15

Ile Tyr Glu Glu Arg Glu Asn Lys Asp Val Asp Arg Val Ile Asn Val
                20                  25                  30

His Gly Asn Asp Val Thr Arg Ile Ile Asp Lys Arg Ser Glu Asp Phe
            35                  40                  45

Ile Val Asp Arg Leu Lys Ser Leu Gly Tyr Asn Ile Leu Ile Val Thr
50                  55                  60

Glu Glu Ser Gly Val Ile Asp Ser Tyr Gly Lys Asn Tyr Asp Tyr Ile
65                  70                  75                  80

Ala Ile Val Asp Pro Leu Asp Gly Ser Thr Asn Phe Val Ser Gly Ile
                85                  90                  95

Pro Trp Ser Ser Val Ser Ile Ala Ile Tyr Asn Arg Asp Glu Glu Asp
                100                 105                 110

Ile Leu Ser Ser Asn Val Gly Ala Val Ser Ser Ile Phe Thr Pro Tyr
            115                 120                 125

Thr Phe Ser Tyr Asp Glu Gly Ser Ala Tyr Val Asn Gly Val Lys Ile
        130                 135                 140

Ala Glu Ile Lys Lys Pro Glu Lys Ile Leu Leu Ala Tyr Phe Ser
145                 150                 155                 160

Arg Ser Lys Leu Pro Asn Leu Lys Leu Phe Phe Glu Lys Ile Gly Gln
                165                 170                 175

Gly Tyr Lys Ile Arg Ser Leu Gly Ser Ala Ser Leu Asp Met Ile Leu
            180                 185                 190

Val Cys Thr Gly Arg Ala Thr Met Phe Phe Asp Ile Arg Gly Lys Leu
        195                 200                 205

Arg Asn Val Asp Ile Ala Ala Ser Ser Asn Phe Cys Ser Arg Leu Gly
    210                 215                 220

Val Ile Pro Tyr Asp Ile Gly Leu Arg Lys Ile Lys Ser Ser Leu Thr
225                 230                 235                 240

Glu Val Ser Val Val Lys Asp Leu Val Ile Ser Leu Asp Glu Ser Leu
                245                 250                 255

Leu Arg Ser Phe Ser Leu Ala Leu Gln Thr Val
            260                 265

<210> SEQ ID NO 12
<211> LENGTH: 258
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Thermosulfidibacter takaii

<400> SEQUENCE: 12

Met Leu Glu Leu Leu Lys Asp Thr Ala Lys Lys Ala Gly Arg Leu Leu
1               5                   10                  15

Lys Ile Arg Phe Leu Glu Leu Leu Asn Gly Met Glu Thr Glu Val Arg
                20                  25                  30

Glu Lys Gly Lys Ser Asp Phe Val Thr Arg Val Asp Val Glu Val Glu
            35                  40                  45

Asn Tyr Ile Lys Glu Leu Leu Ala Asn Thr Asn Ile Ser Val Val Gly
        50                  55                  60

Glu Glu Ser Phe Lys Gly Glu Ile Pro Gly Thr Cys Ile Phe Ile Asp
65                  70                  75                  80

Pro Ile Asp Gly Thr Arg Asn Phe Met Arg Lys Asn Pro His Phe Ala

```
                     85                  90                  95
Ile Asn Leu Ala Tyr Gln Glu Lys Gly Lys Leu Leu Ala Gly Val Thr
                100                 105                 110

Tyr Asp Pro Met Lys Asn Glu Met Phe Ser Ala Ala Phe Ser Lys Gly
            115                 120                 125

Ala Phe Leu Asn Gly Glu Arg Ile Tyr Ala Ser Thr Asn Lys Asp Ile
        130                 135                 140

Gly Lys Ala Ile Ile Ala Ile Gly Leu Pro Tyr Arg Gly Arg Glu Leu
145                 150                 155                 160

Ile Asp Ile Gln Thr Asn Leu Tyr Arg Asn Ile Phe Leu Asn Gly Ala
                165                 170                 175

Ala Thr Arg His Thr Gly Ser Ala Ala Leu Asp Leu Ala Tyr Ile Ser
                180                 185                 190

Cys Gly Arg Tyr Asp Ala Ala Ile Tyr Phe Tyr Leu Ser Pro Trp Asp
            195                 200                 205

Val Ala Pro Gly Ile Leu Leu Val Glu Glu Ala Gly Gly Glu Val Glu
        210                 215                 220

Gly Thr Met Gly Arg Glu Pro Ile Gln Gly Trp Ile Ile Ala Ser Asn
225                 230                 235                 240

Lys Val Ile His Pro Glu Val Lys Asp Ile Leu Glu Gly Ser Leu Lys
                245                 250                 255

Ala Val
```

<210> SEQ ID NO 13
<211> LENGTH: 254
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Pyrococcus furiosus

<400> SEQUENCE: 13

```
Met Lys Leu Lys Phe Trp Arg Glu Val Ala Ile Asp Ile Ile Ser Asp
1               5                   10                  15

Phe Glu Thr Thr Ile Met Pro Phe Phe Gly Asn Pro Asp Gly Gly Lys
                20                  25                  30

Leu Val Lys Ile Ser Pro Ser Gly Asp Glu Thr Lys Leu Val Asp Lys
            35                  40                  45

Leu Ala Glu Asp Leu Ile Leu Ser Arg Ile Thr Glu Leu Gly Val Asn
        50                  55                  60

Val Val Ser Glu Glu Val Gly Val Ile Asp Asn Glu Ser Glu Tyr Thr
65                  70                  75                  80

Val Ile Val Asp Pro Leu Asp Gly Ser Tyr Asn Phe Ile Ala Gly Ile
                85                  90                  95

Pro Phe Phe Ala Leu Ser Leu Ala Val Phe Lys Lys Asp Lys Pro Ile
                100                 105                 110

Tyr Ala Ile Ile Tyr Glu Pro Met Thr Glu Arg Phe Phe Glu Gly Ile
            115                 120                 125

Pro Gly Glu Gly Ala Phe Leu Asn Gly Lys Arg Ile Lys Val Arg Lys
        130                 135                 140

Thr Pro Asp Glu Lys Pro Ser Ile Ser Phe Tyr Ser Arg Gly Lys Gly
145                 150                 155                 160

His Glu Ile Val Lys His Val Lys Arg Thr Arg Thr Leu Gly Ala Ile
                165                 170                 175
```

```
Ala Leu Glu Leu Ala Tyr Leu Ala Met Gly Ala Leu Asp Gly Val Val
            180                 185                 190

Asp Val Arg Lys Tyr Val Arg Pro Thr Asp Ile Ala Ala Gly Thr Ile
        195                 200                 205

Ile Ala Lys Glu Ala Gly Ala Leu Ile Lys Asp Ser Ala Gly Lys Asp
        210                 215                 220

Ile Asp Ile Ser Phe Asn Ala Thr Asp Arg Leu Asp Val Ile Ala Val
225                 230                 235                 240

Asn Ser Glu Glu Leu Leu Lys Thr Ile Leu Ser Leu Leu Glu
                245                 250
```

<210> SEQ ID NO 14
<211> LENGTH: 252
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Archaeoglobus fulgidus

<400> SEQUENCE: 14

```
Met Asp Glu Arg Asp Ala Leu Arg Ile Ser Arg Glu Ile Ala Gly Glu
1               5                   10                  15

Val Arg Lys Ala Ile Ala Ser Met Pro Leu Arg Glu Arg Val Lys Asp
            20                  25                  30

Val Gly Met Gly Lys Asp Gly Thr Pro Thr Lys Ala Ala Asp Arg Val
        35                  40                  45

Ala Glu Asp Ala Ala Leu Glu Ile Leu Arg Lys Glu Arg Val Thr Val
    50                  55                  60

Val Thr Glu Glu Ser Gly Val Leu Gly Glu Gly Asp Val Phe Val Ala
65                  70                  75                  80

Leu Asp Pro Leu Asp Gly Thr Phe Asn Ala Thr Arg Gly Ile Pro Val
                85                  90                  95

Tyr Ser Val Ser Leu Cys Phe Ser Tyr Ser Asp Lys Leu Lys Asp Ala
            100                 105                 110

Phe Phe Gly Tyr Val Tyr Asn Leu Ala Thr Gly Asp Glu Tyr Tyr Ala
        115                 120                 125

Asp Ser Ser Gly Ala Tyr Arg Asn Gly Glu Arg Ile Glu Val Ser Asp
    130                 135                 140

Ala Glu Glu Leu Tyr Cys Asn Ala Ile Ile Tyr Tyr Pro Asp Arg Lys
145                 150                 155                 160

Phe Pro Phe Lys Arg Met Arg Ile Phe Gly Ser Ala Ala Thr Glu Leu
                165                 170                 175

Cys Phe Phe Ala Asp Gly Ser Phe Asp Cys Phe Leu Asp Ile Arg Pro
            180                 185                 190

Gly Lys Met Leu Arg Ile Tyr Asp Ala Ala Ala Gly Val Phe Ile Ala
        195                 200                 205

Glu Lys Ala Gly Gly Lys Val Thr Glu Leu Asp Gly Glu Ser Leu Gly
    210                 215                 220

Asn Lys Lys Phe Asp Met Gln Glu Arg Leu Asn Ile Val Ala Ala Asn
225                 230                 235                 240

Glu Lys Leu His Pro Lys Leu Leu Glu Leu Ile Lys
                245                 250
```

<210> SEQ ID NO 15
<211> LENGTH: 265
<212> TYPE: PRT

<213> ORGANISM: Artificial Sequence
<220> FEATURE:
<223> OTHER INFORMATION: Protein having the activity of psicose-6-phosphate phosphatase Amino acid sequence of inositol-mono-phosphatase from Alicyclobacillus acidocaldarius

<400> SEQUENCE: 15

```
Met Asp Lys Ala Trp Leu Asp Gly Leu Ala Glu Val Val Arg Glu Ala
1               5                   10                  15

Gly Arg Leu Val Glu Glu Ile Ala Arg Gln Gly Phe Asp Thr Gln Phe
            20                  25                  30

Lys His Pro Glu Glu Arg Arg Asp Pro Val Thr Thr Ala Asp Leu Ala
        35                  40                  45

Cys Asp Ala Phe Leu Lys Glu Arg Leu Leu Thr Leu Leu Pro Glu Ala
    50                  55                  60

Gly Trp Leu Ser Glu Glu Thr Lys Asp Arg Pro Asp Arg Leu Glu Lys
65                  70                  75                  80

Arg Trp Val Trp Ile Val Asp Pro Ile Asp Gly Thr Arg Glu Phe Val
                85                  90                  95

Arg Arg Ile Pro Glu Tyr Ala Ile Ser Val Ala Leu Ala Arg Asp Gly
            100                 105                 110

Glu Pro Val Ala Gly Ala Val Val Asn Pro Ala Thr Gly Asp Leu Phe
        115                 120                 125

Leu Gly Ala Val Gly Val Gly Ala Trp Arg Asn Gly Thr Pro Met Val
    130                 135                 140

Cys Ser Arg Ile Arg Gly Glu Arg Leu Thr Ile Leu Gly Ser Arg Ser
145                 150                 155                 160

Glu Met Asn Arg Gly Glu Phe Glu Pro Phe Ala Gly Ile Leu Glu Val
                165                 170                 175

Arg Ala Val Gly Ser Ile Ala Tyr Lys Leu Ala Leu Val Ala Ala Gly
            180                 185                 190

Glu Ala Asp Gly Thr Phe Ser Leu Gly Pro Lys His Glu Trp Asp Ile
        195                 200                 205

Ala Ala Gly Val Ala Leu Val Leu Ala Ala Gly Gly Arg Val His Asp
    210                 215                 220

Gly Ala Gly Arg Pro Phe Arg Phe Asn Gln Pro His Thr Leu Thr Arg
225                 230                 235                 240

Gly Ile Val Ala Ala Thr Arg Glu Ala Tyr Gly Asp Leu Ala Leu Leu
                245                 250                 255

Ile Glu Arg His Ala Pro Arg Arg Ala
            260                 265
```

<210> SEQ ID NO 16
<211> LENGTH: 258
<212> TYPE: PRT
<213> ORGANISM: Artificial Sequence
<220> FEATURE:
<223> OTHER INFORMATION: Protein having the activity of psicose-6-phosphate phosphatase Amino acid sequence of inositol-mono-phosphatase from Meiothermus silvanus

<400> SEQUENCE: 16

```
Met Asp Leu Gln Arg Tyr Leu Glu Ala Ala Leu Asp Ala Ala Tyr Leu
1               5                   10                  15

Ala Arg Gly Ile His Leu Tyr Tyr Arg Glu Lys Gly Phe Ala Leu Glu
            20                  25                  30

Ser Lys Thr Ser Pro Thr Asp Leu Val Thr Gln Ala Asp Arg Glu Ser
        35                  40                  45
```

Glu Ala Ile Arg Ser Leu Leu Glu Arg Phe Pro Asp His Val
50                  55                  60

Val Leu Gly Glu Glu Gly Gln Glu Gly His Ser Asp Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Ala Leu Glu Val Gly Gly Glu Val Val Val
                100                 105                 110

Gly Ala Val Leu Asp Thr Ala Arg Gly Glu Leu Phe Thr Ala Leu Lys
                115                 120                 125

Gly Glu Gly Ala Phe Gln Asn Gly Arg Pro Ile Arg Val Ser Ser Thr
130                 135                 140

Ala Thr Leu Ile Gly Ser Leu Leu Ala Thr Gly Phe Pro Tyr Asp Val
145                 150                 155                 160

Ala Lys Asp Ala Glu Asn Leu Thr Tyr Phe Gln Arg Ala Leu Ala Lys
                165                 170                 175

Gly Leu Thr Val Arg Arg Pro Gly Ala Ala Ala Leu Asp Leu Ala Tyr
                180                 185                 190

Val Ala Ala Gly Arg Leu Glu Gly Phe Trp Glu Val Lys Leu Asn Pro
195                 200                 205

Trp Asp Val Ala Ala Gly Trp Leu Leu Ile Thr Glu Ala Gly Gly Thr
210                 215                 220

Val Ser Gly Ile Gln Gly Glu Pro Tyr Arg Leu Gly Asn Arg Tyr Leu
225                 230                 235                 240

Val Ala Ser Asn Gly Lys Ile His Glu Gln Leu Leu Asp Thr Leu His
                245                 250                 255

Gly Arg

<210> SEQ ID NO 17
<211> LENGTH: 258
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Meiothermus rufus

<400> SEQUENCE: 17

Met Asp Leu Arg Pro Tyr Leu Glu Ala Ala Leu Asp Ala Ala Tyr Leu
1               5                   10                  15

Ala Lys Gly Ile His Gln Tyr Tyr Gln Glu Lys Gly Phe Thr His Ser
                20                  25                  30

Thr Lys Ser Thr Pro Thr Asp Val Val Thr Gln Ala Asp His Glu Ala
            35                  40                  45

Glu Ala Ala Ile Arg Ala Leu Ile Ala Glu Arg Phe Pro Asp His Val
50                  55                  60

Val Leu Gly Glu Glu Gln Gly Gln Glu Gly Gly Glu Phe Arg Trp
65                  70                  75                  80

Ile Val Asp Pro Leu Asp Gly Thr Val Asn Tyr Ala His Gly Phe Pro
                85                  90                  95

Phe Tyr Gly Val Ser Ile Gly Leu Glu Val Arg Gly Glu Val Val Leu
                100                 105                 110

Gly Val Val Leu Asp Thr Ala Arg Gly Asp Leu Phe Thr Ala Thr Lys
                115                 120                 125

Gly Gly Gly Ala Tyr Leu Asn Gly Arg Pro Leu Arg Val Ser Gln Arg

```
             130                 135                 140
Thr Thr Leu Val Gly Ser Leu Leu Ala Thr Gly Phe Pro Tyr Asp Val
145                 150                 155                 160

Ala Arg Asp Pro Glu Asn Leu Thr Tyr Phe Gln Arg Ala Leu Ala Lys
                165                 170                 175

Gly Leu Thr Val Arg Arg Pro Gly Ala Ala Leu Asp Leu Ala Asn
                180                 185                 190

Val Ala Ala Gly Arg Leu Asp Gly Phe Trp Glu Val Lys Leu Asn Pro
            195                 200                 205

Trp Asp Val Ala Ala Gly Trp Leu Leu Ile Thr Glu Ala Gly Gly Gln
        210                 215                 220

Val Thr Gly Phe Gln Gly Glu Ala Tyr Arg Leu Gly Asn Arg Tyr Leu
225                 230                 235                 240

Val Ala Ser Asn Gly Arg Ile His Gln Ala Leu Leu Glu Ala Leu Gln
                245                 250                 255

Gly Arg

<210> SEQ ID NO 18
<211> LENGTH: 258
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Meiothermus taiwanensis

<400> SEQUENCE: 18

Met Asp Leu Arg Ala Tyr Leu Gln Thr Ala Leu Asp Ala Ala Tyr Leu
1               5                   10                  15

Ala Lys Gly Ile His Gln Tyr Tyr Gln Glu Lys Gly Phe Thr Gln Ser
                20                  25                  30

Ser Lys Ser Thr Pro Thr Asp Leu Val Thr Gln Ala Asp His Glu Ser
            35                  40                  45

Glu Ala Ala Ile Arg Glu Leu Ile Ala Ala Arg His Pro Asp His Val
    50                  55                  60

Val Leu Gly Glu Glu Gln Gly Gln Asp Lys Glu Gly Ala Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Gly Leu Glu Ala His Gly Glu Val Val Leu
                100                 105                 110

Gly Val Val Leu Asp Thr Ala Arg Gly Glu Leu Phe Thr Ala Thr Lys
            115                 120                 125

Gly Gly Gly Ala Tyr Leu Asn Gly Arg Pro Ile Arg Val Ser Thr Arg
        130                 135                 140

Ser Thr Leu Val Gly Ser Leu Leu Ala Thr Gly Phe Pro Tyr Asp Val
145                 150                 155                 160

Ser Lys Asp Thr Glu Asn Leu Thr Tyr Phe Gln Arg Ala Leu Thr Lys
                165                 170                 175

Gly Leu Met Val Arg Arg Pro Gly Ala Ala Leu Asp Leu Ala Tyr
                180                 185                 190

Val Ala Ala Gly Arg Leu Asp Gly Phe Trp Glu Val Lys Leu Asn Pro
            195                 200                 205

Trp Asp Val Ala Ala Gly Trp Leu Ile Val Ser Glu Ala Gly Gly Arg
        210                 215                 220
```

Val Ser Gly Leu Gln Gly Glu Asp Tyr Arg Leu Gly Asn Arg Tyr Leu
225                 230                 235                 240

Val Ala Ser Asn Gly Leu Ile His Gln Pro Leu Leu Asp Thr Leu His
                245                 250                 255

Gly Arg

<210> SEQ ID NO 19
<211> LENGTH: 258
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Meiothermus chliarophilus

<400> SEQUENCE: 19

Met Asp Leu Arg Pro Phe Leu Glu Thr Ala Leu Ala Ala Ala Tyr Val
1               5                   10                  15

Ala Arg Gly Ile His Gln Leu Tyr Gln Asp Lys Gly Phe Thr Gln Ser
                20                  25                  30

Thr Lys Ser Thr Pro Thr Asp Val Val Thr Gln Ala Asp Lys Glu Ala
            35                  40                  45

Glu Ala Ala Ile Arg Ala Leu Ile Glu Gln Arg His Pro Gly His Val
    50                  55                  60

Val Leu Gly Glu Glu Gly Gln Gln Gly Gly Glu Tyr Arg Trp
65                  70                  75                  80

Ile Val Asp Pro Leu Asp Gly Thr Val Asn Tyr Ala His Gly Phe Pro
                85                  90                  95

Phe Tyr Cys Val Ser Ile Gly Leu Glu Val Arg Gly Glu Val Met Val
            100                 105                 110

Gly Val Val Leu Asp Thr Ala Arg Gly Asp Leu Phe Thr Ala Thr Arg
        115                 120                 125

Gly Gly Gly Ala Tyr Phe Asn Gly Arg Pro Met Arg Val Ser Arg Ser
    130                 135                 140

Pro Lys Leu Leu Gly Ser Leu Ile Ala Thr Gly Phe Pro Tyr Asp Val
145                 150                 155                 160

Ala Arg Asp Arg Glu Asn Leu Thr Tyr Leu Glu Arg Val Leu Phe Lys
                165                 170                 175

Gly Ile Thr Val Arg Arg Pro Gly Ala Ala Ala Leu Asp Leu Ala Tyr
            180                 185                 190

Val Ala Cys Gly Arg Leu Asp Gly Phe Trp Glu Val Lys Leu Asn Pro
        195                 200                 205

Trp Asp Val Ala Ala Gly Trp Leu Leu Val Glu Glu Ala Gly Gly Arg
    210                 215                 220

Ile Thr Gly Ile His Gly Glu Pro Tyr Arg Met Gly Asn Arg Tyr Leu
225                 230                 235                 240

Met Ala Ser Asn Gly His Ile His Glu Glu Leu Leu Ala Thr Ile His
                245                 250                 255

Gly Arg

<210> SEQ ID NO 20
<211> LENGTH: 258
<212> TYPE: PRT
<213> ORGANISM: Artificial Sequence
<220> FEATURE:
<223> OTHER INFORMATION: Protein having the activity of psicose-6-
      phosphate phosphatase Amino acid sequence of inositol-mono-
      phosphatase from Meiothermus cerbereus

<400> SEQUENCE: 20

```
Met Asp Leu Arg Val Tyr Leu Gln Thr Ala Leu Asp Ala Ala Tyr Leu
1               5                   10                  15

Ala Lys Gly Ile His Gln Tyr Tyr Gln Glu Lys Gly Phe Thr Leu Ser
            20                  25                  30

Ser Lys Ser Thr Pro Thr Asp Leu Val Thr Gln Ala Asp His Glu Ser
        35                  40                  45

Glu Ala Ala Ile Arg Glu Leu Ile Ala Ala Arg His Pro Asp His Val
50                  55                  60

Val Leu Gly Glu Glu Gln Gly Gln Asp Arg Glu Gly Ala Phe Arg Trp
65                  70                  75                  80

Ile Val Asp Pro Leu Asp Gly Thr Val Asn Tyr Ala His Gly Phe Pro
                85                  90                  95

Phe Tyr Ala Val Ser Ile Gly Leu Glu Ala His Gly Glu Val Val Leu
            100                 105                 110

Gly Val Ile Leu Asp Thr Ala Arg Gly Asp Leu Phe Thr Ala Thr Lys
        115                 120                 125

Gly Gly Gly Ala Phe Met Asn Gly Arg Pro Ile Arg Val Ser Pro Arg
130                 135                 140

Ala Thr Leu Val Gly Ser Leu Leu Ala Thr Gly Phe Pro Tyr Asp Val
145                 150                 155                 160

Ser Lys Asp Thr Glu Asn Leu Val Tyr Phe Gln Arg Ala Leu Thr Arg
                165                 170                 175

Gly Leu Met Val Arg Arg Pro Gly Ala Ala Leu Asp Leu Ala Tyr
            180                 185                 190

Val Ala Ala Gly Arg Leu Asp Gly Phe Trp Glu Val Lys Leu Asn Pro
        195                 200                 205

Trp Asp Val Ala Ala Gly Trp Leu Ile Ile Arg Glu Ala Gly Gly Thr
210                 215                 220

Val Thr Gly Met Glu Gly Glu Ala Tyr Arg Leu Gly Asn Arg Tyr Leu
225                 230                 235                 240

Val Ala Ser Asn Gly Leu Ile His Gln Pro Leu Leu Asp Thr Ile His
                245                 250                 255

Gly Arg
```

<210> SEQ ID NO 21
<211> LENGTH: 819
<212> TYPE: DNA
<213> ORGANISM: Artificial Sequence
<220> FEATURE:
<223> OTHER INFORMATION: Nucleotide sequence encoding psicose-6-phosphate phosphatase Nucleotide sequence encoding inositol-monophosphatase from Rhodothermus marinus

<400> SEQUENCE: 21

```
atgatggatg cctacacgct ttacgaagaa gcccgtgagg tggcggcccg gctggcccgc    60
gatgccggac agatcgcccg ctactatgcc ggtcgggtga ccgtccgcga aaaaggctat   120
aacgagctgg tcacgcaggc cgacgaagaa gtacagcgct tcctgatcga gcagatccac   180
cggcatttcc ccgagcacgc gattctggcc gaggagaacc tgtccgacat gcaggacggc   240
agggaagggg cgtcgtttcg atggatcatc gatccgatcg acggcacgac gaacttcacg   300
cacggtgtgc cgcccctatgg catcagtctg gcactccagc atgaaggccg acggtcgtg   360
ggggtcgtct acgacgtgcc ccacgacgag ctgttcaccg cagtgcgggg cggcgggctg   420
```

| | |
|---|---|
| tacgtcaacg gggtgcgcgc ccgggttagc cagaccgaaa cgctccggga ggcgctcatc | 480 |
| acgaccggct tcccctaccg ggaagtcgtg catctggaag aatatctgga ggcgctcggg | 540 |
| cgtgtgattc gagcgacgcg aggggtgcgt cggccgggcg cggcttcggt cgatctggcc | 600 |
| tgggtggcct gcggacgctt cgacggattc ttcgagacgg gcctgagtcc ctgggatgta | 660 |
| gcggccggca tcctgctggt cgaagaaggc ggaggacggg tgacggactt tcacgggcgg | 720 |
| cccgatccga tctttgcccg ccagatgctg ccacgaacg ggcgcatcca cgaggcgctc | 780 |
| tgcgagctgg tcgcgccgct gcaccacgtc tacgcctga | 819 |

<210> SEQ ID NO 22
<211> LENGTH: 768
<212> TYPE: DNA
<213> ORGANISM: Artificial Sequence
<220> FEATURE:
<223> OTHER INFORMATION: Nucleotide sequence encoding psicose-6-phosphate phosphatase Nucleotide sequence encoding inositol-mono-phosphatase from Thermotoga lettingae

<400> SEQUENCE: 22

| | |
|---|---|
| atggacagaa tggattttc aataaagatc gccagaaaag tcggtctcta cctgatggaa | 60 |
| cactggggca atgcagaaaa tgttcggcaa aaaagctctt ttcaggacct ggtaagtgac | 120 |
| tgcgacaagc aagcacagaa atgattgtt cagaagataa agaccatttt ccagatgac | 180 |
| gctattttag ccgaggaagg gctattcgaa aaggagaca gaatgtggat aattgaccca | 240 |
| atagatggca caatgaacta cgtccatggt ctaccttctt ttgcgattgg aatcgcctac | 300 |
| gttgaaaaag agcaagttat ccttggcgta gcacacgatc cagttctcaa cgagacatac | 360 |
| tatgcaatca aagggcaggg tgcgtataaa atgggggaaa gaataaatgt ttcagaaaat | 420 |
| tcgcttttga aagactctat tggaaatact ggcttttata cagatttac agggatcttc | 480 |
| atcagcgcaa tcgaaaagaa agtcaggcgg gtgagaatga caggcagtgc tatacttgct | 540 |
| ggcgcttatg ttgcctgtgg aagtttgat ttctttatag caaaaagagc caattcttgg | 600 |
| gatgtagctc ctttatcgt cctcgtccca gaagctggtg gaatcgtaac ggacctgtcc | 660 |
| ggaaaccagg cacatctcaa caccggtaat ttcttttca gtaacggtct attacacgat | 720 |
| caggtcttag aagtcataag agaggtgaat aaaaaagtaa gaaaatga | 768 |

<210> SEQ ID NO 23
<211> LENGTH: 777
<212> TYPE: DNA
<213> ORGANISM: Artificial Sequence
<220> FEATURE:
<223> OTHER INFORMATION: Nucleotide sequence encoding psicose-6-phosphate phosphatase Nucleotide sequence encoding inositol-mono-phosphatase from Meiothermus ruber

<400> SEQUENCE: 23

| | |
|---|---|
| atggacttgc gtgcctatct gcaaaccgcc ctcgacgccg cctatttagc caaaggcatc | 60 |
| caccagtact accaggaaaa aggctttacc cagagcacca gtccacccc caccgatcta | 120 |
| gtcacccagg ccgaccacga gtcggaggcg gccatccgag aactcattgc ttcgcgccac | 180 |
| cccgaccacg tggtgctggg cgaggaacaa ggccaggaca agaggggggc cttccgctgg | 240 |
| attgtagacc ccctggacgg caccgtaaac tacgcccatg gcttcccttt ttatgcggtg | 300 |
| agcatcggcc tggaagccca cggcgaggtg gtgctggggg tggttctgga taccgcccgg | 360 |
| ggcgagctat ttaccgctac caagggggc ggggcctacc tgaatggtcg tcccattcgg | 420 |
| gtatccaccc gttcaacct ggtgggcagc cttctagcca ccggattccc ctacgatgtg | 480 |

| | | | | |
|---|---|---|---|---|
| agcaaggaca | ccgaaaacct | ggtctacttt | cagcgggccc | tgaccaaggg gctcatggtg | 540 |
| cggcgaccgg | gcgcggcagc | cctcgacctg | gcttatgtgg | ccgctgggcg cctggacggc | 600 |
| ttctgggaag | tgaagctcaa | cccctgggat | gtggccgcgg | gctggctcat cgttagcgag | 660 |
| gccggagggc | ggataaccgg | ccttcaaggg | gaggattacc | ggctgggcaa ccgctaccta | 720 |
| gtggcctcca | acggcctgat | ccacgggccg | ctgctggaca | ccatccacgg gcgatag | 777 |

<210> SEQ ID NO 24
<211> LENGTH: 798
<212> TYPE: DNA
<213> ORGANISM: Artificial Sequence
<220> FEATURE:
<223> OTHER INFORMATION: Nucleotide sequence encoding psicose-6-
phosphate phosphatase Nucleotide sequence encoding inositol-mono-
phosphatase from Dictyoglomus turgidum

<400> SEQUENCE: 24

| | | | | |
|---|---|---|---|---|
| atgaagagaa | tacttgaagt | agctataaaa | acaattaaag | aatctggtaa tatactttg | 60 |
| aactacatag | gcgaggaaaa | agaaatagaa | cttaaaggaa | tttccaattt agtcactcaa | 120 |
| gtagataaac | tctcagaaag | acatatacta | aaatccatag | aagaaaattt tccggatcat | 180 |
| tcaatcttga | cagaagaaac | aggctttata | aataaaaatt | ctgaatatac ctggattgta | 240 |
| gatcccttag | atggaaccac | aaattatgcc | cataatttcc | cttttttgg aattagtatt | 300 |
| gccctcataa | aaaataaaga | aataatactt | ggattaatct | atgatcccat aagagacgag | 360 |
| ttattttatg | ccataaaaaa | tgaaggtgca | tacctaaatg | ataggagaat agaggtatca | 420 |
| aaaacagaaa | gtcttgaaaa | ttctctcatt | agttttgcct | ttccttacga attaagtctt | 480 |
| gaggagaaaa | attttattcc | ttttataaat | ttttcctcta | gaactcatgg tataagaagg | 540 |
| acaggttcgg | cagcaataga | aatagcctat | gtagggtgtg | aagacttga tggattttgg | 600 |
| gcaaagaaac | taaaaccatg | ggatattagt | gcaggcattc | taatagtgga gaggcaaaa | 660 |
| ggtaaagtta | cagattttag | tggaaacaat | attgatattc | atacagacaa tattttgttt | 720 |
| tcaaacggta | aaatacacca | agagatgata | aaaatcttaa | atttaggtaa aatattcatt | 780 |
| agaaatgaaa | aattttga | | | | 798 |

<210> SEQ ID NO 25
<211> LENGTH: 756
<212> TYPE: DNA
<213> ORGANISM: Artificial Sequence
<220> FEATURE:
<223> OTHER INFORMATION: Nucleotide sequence encoding psicose-6-
phosphate phosphatase Nucleotide sequence encoding inositiol-mono-
phosphatase from Pyrobaculum ferrireducens

<400> SEQUENCE: 25

| | | | | |
|---|---|---|---|---|
| atgctcggcg | tcttggaggc | cgtggcggtc | cgcgcctcgc | attttttaat ggagtacttc | 60 |
| agagccggca | gaggcgtaga | cgtcgtgtcg | cgtaaagagg | acgacgtcac cagggaggtg | 120 |
| gacatcgccg | cggagacgct | catatacaaa | atgctcagag | aggcctttaa agaaggcggc | 180 |
| gtcctatacg | cagaggaagg | cggcatctac | aggtggggag | acgagcgcta catcttcgtc | 240 |
| ctagacccac | tcgacgggtc | gctgaactac | gccgtgggcg | tgcccttctt cgccgtatct | 300 |
| atcgcggcag | ggaaacatag | agagggcacc | ctggccgatt | tagaatacgc cgtcgtggcg | 360 |
| ataccccca | cggagacgt | ctacacggcg | gcccccggcg | tcggcgcccg caaaaacgga | 420 |
| aagccgttga | ggaggacccc | gaggagcaat | atagtattcg | tagcggtgag caacagcttc | 480 |

```
ccccaaaga cctgcgaagt cgtgaggcgg ctggggctca gggggaggag cctcggcagc    540
tccgccgccg agctggcgta cacggtggaa ggcatagccc gcggcttcct agacctccgg    600
ggcaagctca gactgctcga cgtggcgggg gcattgacga taggcaaata cgtagacggc    660
ttccggtacg tggtgatggg cgacaccaag ccgcactcca aggtgtctct agtggcgggc    720
gacgtagatt tcgtaaatgc cgcaaccaca gattga                              756
```

<210> SEQ ID NO 26
<211> LENGTH: 774
<212> TYPE: DNA
<213> ORGANISM: Artificial Sequence
<220> FEATURE:
<223> OTHER INFORMATION: Nucleotide sequence encoding psicose-6-
    phosphate phosphatase Nucleotide sequence encoding inositol-mono-
    phosphatase from Thermoanaerobacter wiegelii

<400> SEQUENCE: 26

```
atgaaagatg agaaaggaat tgtagtagat attataaaaa aagcaggaga gattcttcaa     60
gatgggtgga ataaaaaaaa tttaaaatt tatcggaaag gaacaattaa tttagttaca    120
gaaatagata agaaaattga atttcttata atacaacttt taaaacaata ttttcctgat    180
tatggtattc ttacagaaga aagcaaagaa attaacagca aagcaaacgt gcgatggatt    240
atagatcccc tagatggtac tactaattat ataaaacaat atccgtttgt agccatatca    300
attgctttag agaagaagg agaattaatt ttgggagttg tttataatcc gattttaaat    360
gaaatgttta tagctcaaaa aggatgtggt gcgacttata tgggaagtc aattcatgtt    420 tctaaaataa agaattggg atcggcagtt ctagcatcgg gctttcctta tgatgcgtgg    480
gaaaatcctg ataataatgc taaacaatgg aggcaatttc ttactcgtag tttatctctt    540
cgatgcgatg gatcagcagc tctcgatctt tgtagagtag cttgtggaca attggatggt    600
tattgggaaa agggaattag cccgtgggat gttgcagctg gtattgtaat attgcgcgaa    660
gcaggaggaa taattactga ttatttgggt gaggaaaatt tctttaaacg tggagaagtt    720
gttgctgcaa atcctgttct ccacgcacaa atgttgaaag ttttaaataa ttag          774
```

<210> SEQ ID NO 27
<211> LENGTH: 795
<212> TYPE: DNA
<213> ORGANISM: Artificial Sequence
<220> FEATURE:
<223> OTHER INFORMATION: Nucleotide sequence encoding psicose-6-
    phosphate phosphatase Nucleotide sequence encoding inositol-mono-
    phosphatase from Thermus thermophilus

<400> SEQUENCE: 27

```
atgatcggga ggcgccaccc ctactacccg tacctggagg cggccctgga ggcggcgagc     60
ctcgcccggg gcatccacct ctactacctg gaaaagggct tcaccgaggg gaccaagtcc    120
ggccccaccg acctggtgac ccaggcggac cgggaggcgg aagaggcggt gaagggcctc    180
ctcctctccc gcttccccga ggcggggttt ctggggaggag aaggggaag cgagggcggg    240 aaggccctcc gcttcatcgt ggacccgctg gacgggacgg tgaactacgc ccacggcttc    300
cccttcttcg ccgtatccat cgccctcgag gccgagggcg ccatccagat gggcgtggtg    360
atggacaccg cccggggga ggtcttctac gccctgaggg gggaagggc ctacctcaac    420 ggccgcccca tccgggtcac ggggcgggag agcctcgtgg ggagcctcct cgccacgggc    480
ttcccctacg acgtggccaa ggacccggaa aacctcacct actttgaacg ggccctgggc    540
aagggcctgc tcgtccgcag gcctgggcg gcggccctgg acctggccta cgtggccgcg    600
```

```
gggcggctgg agggcttctg ggaggtgaag ctgaaccccct gggacgtggc ggcggggtgg    660
ctcctcgtgg aagaggcggg aggaagggtg acggacctcg aggggaaccc ctaccgcctg    720
ggcagccgct acatcctcgc caccaacggg cgggtccacg aggccctgcg ccggaccctc    780
ctgggcctgg actga                                                    795

<210> SEQ ID NO 28
<211> LENGTH: 756
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Thermococcus litoralis

<400> SEQUENCE: 28
atgtatgaat ggaatgaaat agccctaaat ctcgcaaagg atattgaaag agaagtaatg     60
cctctctttg aacaaagaa ggctggagaa ttcatcgggt ttagcccgag cggggacaaa    120
actaaactcg tagataaagt tgcagaagac gttgttctgg agtatctcag accccttggc    180
gtaaacgtag taagtgagga gattgggaac atagaggctg gaagtgaata cactattgtt    240
gtcgacccca tcgatggttc tttcaacttt atccaaggca tccctatctt tggattcagc    300
tttgcagttt tcaaaaatga aaaacccgtc tatgctatga tttacgagtt catcacaaag    360
aacgtttatg aaggaattcc cggtgaggga gcctatctaa acggggagag aatacgagtt    420
aggcatttaa atgaaaagtc catctcaata agcttctaca caagaggtag gggagcgagg    480
cttgttgaaa aagttaagag aacgagggtt ttaggtgcta tagcagttga gcttgcttat    540
ctcgctagag gttctctaga cggtgtaata gacataagga actatgtaag gccgacagac    600
atagcagcag gttacataat cgcaaaagaa gctggagcta ttataaccga cgatagcgga    660
gaggaaataa agtttagatt agatgcaagg gaaaagctca acataatagc ggtaaatgat    720
aagagactcc ttaagctcat acttgaagtt atttaa                              756

<210> SEQ ID NO 29
<211> LENGTH: 795
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Geobacillus stearothermophilus

<400> SEQUENCE: 29
atggcagaaa atgggaaga atcgaccga tacgcccggc aatggatcga cgaagcagga      60
aagcgcatcc gcgcctcgtt tgccaaacag ctgacggtgg aagcgaaaga gaacccgaac    120
gacttagtga cgaatgttga ccgcgccatt gagcagtttt tcgccgagca catccgtcgc    180
cagttcccta gccaccgcct gttgggggaa aaggatttg gcgaccggat cgatgccttg    240
gacggcgttg tttgggtgat tgacccgatc gacggcacga tgaatttcgt tcatcagcgg    300
cgccattttg ctgtatcgat cggcattttt gaagatggca tcgggcagct cggctacgtg    360
tatgacgtcg tgtttgacga actgtatgcg gcgcaaaaag gcggggggt gttttgaac     420 ggggagccgc tcggcctcct gcagcccgcg ccagtggcgg agtcgatcat cgccatcaac    480
gggacatggc tcatggaaaa caagcgcctc gaccatcgcc cgctcatgag gctggcgaaa    540
gaggcgcgcg gcacgcgctc gtatggttca gcggcgcttg agctcgcgta tgttgccgcc    600
```

```
ggccgtttgg acgcctacat ttcgccgcgc ctgtcgccgt gggatttcgc cggcgggatg    660
attttgattg aagaagcggg cggaatggtg acgacccttg acgggaagcc gctggatctg    720
cttggccgca attcggtgct tgccgcgaaa cctggggtgc acgaagaaat tttgcggcgc    780
tatcttcacg attga                                                     795

<210> SEQ ID NO 30
<211> LENGTH: 780
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Anaerolinea thermophila

<400> SEQUENCE: 30
atgaccactt cccttcgcga tttgctcgat tttgctgtgg aaacggcgta tctggcagga     60
cgaaccaccc tggcgtattt tcagacgggt gttcaggcgg agttcaaagc cgattcttcc    120
cccgtgactc ttgccgaccg cgccgccgag caattgattc gtcaacgcat tgaaaaacgc    180
ttccctcatc atgccattgt gggtgaggaa tttggtgttc agggaagcgc tgatgctacc    240
caccgctggt tcattgaccc gattgacggc accaaatcct tcctgcgcgg cattcccctg    300
tacgctgtgc tgttgggctt ggagattgaa ggcagggtgc aggtgggagt ggcttattac    360
cccgctatgg acgagatgct gtctgccgcc gatggcgagg gatgctggtg aacgggcgg    420 cgggcgcgtg tctccacggc gagccgcctg gcagaagcct gggtgaccag caccgacccc    480
tacaatttcc agaaaaccgg caaagatgcc gcctggcagc gcattcaggc ggtgtcttat    540
caccgcggcg gctggggggga tgcctacggc tatctgctgg ttgctactgg gagagccgaa    600
gtgatgctcg atcccatcat gaacgagtgg gattgcgcgc cgttcccgcc catcttccgc    660
gaagccggtg gttttttcgg agactggcag ggtaacgaaa ccatctatgg cggcgaggcg    720
ctggcaacaa ctcaggttct tctccctgag gtgctggagt gtttacattc ttccctttga    780

<210> SEQ ID NO 31
<211> LENGTH: 804
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Sulfolobus acidocaldarius

<400> SEQUENCE: 31
atgaaaagag aagatgtaga gaaggtagct agcgaagctt ctaaatatat atatgaagag     60
agagaaaaca aggacgtcga cagagtaatt aatgtacatg gtaatgacgt gactagaatt    120
atagataaga gatctgaaga ctttattgtg gacaggttaa aaagtctagg atataatata    180
ctcatagtta cagaagaatc aggtgtaatt gacagttatg ggaaaaatta cgattacatt    240
gcaattgtag atccactgga tggaagtaca aattttgtat caggaatacc atggtcttca    300
gtatctattg ctatatacaa tagggacgaa gaagatatac tcagttcaaa tgtaggtgct    360
gtaagcagta ttttcactcc ttacacattt tcctacgatg aaggaagcgc ttacgtaaat    420
ggcgtaaaga tagcagagat aaaaaagcct gaaaaaatac tattattagc ctatttctcc    480
aggtcaaagc tacctaatct gaaattattt tttgagaaga ttggtcaggg ttataaaata    540
agaagtttag gaagtgcatc cttagatatg atattagtgt gtacaggcag ggcaacaatg    600 tttttttgata agggggaaa actgagaaat gtggatattg cagcctcatc taacttctgt    660
```

```
tccagattag gggtaattcc atacgacata ggtttaagaa aaattaaaag tagtttgacg    720
gaagtaagtg ttgtaaaaga tttagttata agtcttgacg aaagtcttct aagatctttc    780
tctcttgctt tacagacggt ttaa                                           804
```

<210> SEQ ID NO 32
<211> LENGTH: 777
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Thermosulfidibacter takaii

<400> SEQUENCE: 32

```
atgctagaac tgctaaagga tacagcaaaa aaagcaggac gactgctaaa aataagattc     60
ttggaacttt tgaacggcat ggaaaccgag gtaagagaaa agggaaaaag cgattttgta    120
acaagggtag atgttgaagt ggaaaactac ataaaggaac tgcttgctaa cacaaatata    180
tcggtggtgg gagaagaaag ctttaaaggc gagataccgg gcacctgcat cttcatagac    240
cccatagatg gcacaagaaa cttcatgaga aagaaccccc acttcgccat taaccttgct    300
tatcaggaga agggaaagct tttggctgga gtgacctatg accctatgaa gaatgaaatg    360
ttttctgctg catttagcaa aggtgcattt taaacggag agcgcatcta cgcttccaca    420
aacaaggata ttggcaaagc catcatcgct ataggacttc catacagagg aagagaactc    480
atagatattc aaaccaacct ttacaggaac atcttcctaa acggcgctgc tacccgccac    540
acaggctcag cagcccttga tctggcctac atatcctgcg gaagatacga tgctgctatc    600
tatttttatc tttccccctg ggacgtagct ccgggcatac tgctggtaga agaggcaggc    660
ggagaagttg aaggcaccat gggacgagaa cccatccagg ggtggataat agcatctaac    720
aaagtcatcc accccgaagt taaagacatc cttgaaggct cttttaaagc ggtataa      777
```

<210> SEQ ID NO 33
<211> LENGTH: 765
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Pyrococcus furiosus

<400> SEQUENCE: 33

```
atgaagctta agttctggag ggaagtagcc attgacataa tctcagattt cgaaactaca     60
ataatgcctt tctttggaaa ccctgatggg ggaaagctcg taaagataag ccccagtgga    120
gatgagacaa agctggttga taagctcgcc gaggatttaa tactttcaag aatcacagag    180
cttggagtca acgttgtgag cgaggaagtt ggtgttattg ataacgagag tgaatacacc    240
gttatagtag acccactaga tggttcatat aacttcattg ctggaattcc ttttttttgct    300 ttgagtctag cagtatttaa aaaagataag ccaatatatg caattatcta tgaacctatg    360
acagagagat tctttgaggg aatcccagga gagggagctt ttttaaatgg aaaaagaata    420
aaggtaagaa aaaccccgga cgagaagcca tcaataagct tttattctcg aggtaaaggc    480
catgaaatcg ttaaacatgt aaagagaact agaaccttag gggcaatcgc tctagaattg    540 gcataccttag ctatgggtgc attagatgga gtagttgatg tgaggaaata cgtaaggcca    600
acggacatag ctgctggaac gataattgca aaagaggcag gagcccttat taaggactcc    660
```

| | |
|---|---|
| gcgggaaagg atatagatat ttcatttaat gcaactgata ggcttgatgt gatagccgtg | 720 |
| aacagcgaag agttgctaaa aacaattta agcttactgg agtag | 765 |

<210> SEQ ID NO 34
<211> LENGTH: 759
<212> TYPE: DNA
<213> ORGANISM: Artificial Sequence
<220> FEATURE:
<223> OTHER INFORMATION: Nucleotide sequence encoding psicose-6-phosphate phosphatase Nucleotide sequence encoding inositol-mono-phosphatase from Archaeoglobus fulgidus

<400> SEQUENCE: 34

| | |
|---|---|
| atggatgaaa gggatgcgct gagaatttcg agggagattg caggagaggt cagaaaggcc | 60 |
| attgcgtcaa tgcccttgag ggagagagta aaggacgtgg gaatggggaa ggatggcact | 120 |
| ccaaccaagg cagccgacag agttgcggaa gatgctgcgc ttgaaatttt gagaaaggag | 180 |
| agggttacgg tggttacaga ggagtcggga gttttggggg agggagatgt ctttgttgcc | 240 |
| ctcgaccccc tcgatggaac cttcaatgct acgagaggga ttccagttta ttcagtcagc | 300 |
| ctctgcttct cctattcgga taaactgaaa gacgccttct ttggctacgt ttacaacctc | 360 |
| gcaacagggg atgaatacta cgcggactcc agcggggctt acagaaacgg ggagaggatt | 420 |
| gaggtgagcg atgctgagga gctttactgc aacgccataa tctactatcc gacaggaag | 480 |
| tttcccttta agaggatgag gattttttgga agtgctgcaa cggagctttg cttctttgct | 540 |
| gacggctcct tgactgctt cctcgacatc cgccccggaa agatgcttag aatctacgat | 600 |
| gccgctgcgg gtgtttttat tgcagaaaag gcaggaggaa aggttaccga acttgatgga | 660 |
| gaaagcttgg ggaataaaaa atttgatatg caggaaaggc tcaatatcgt cgccgcaaat | 720 |
| gaaaaactcc atccaaagct gctggagctg attaaatga | 759 |

<210> SEQ ID NO 35
<211> LENGTH: 798
<212> TYPE: DNA
<213> ORGANISM: Artificial Sequence
<220> FEATURE:
<223> OTHER INFORMATION: Nucleotide sequence encoding psicose-6-phosphate phosphatase Nucleotide sequence encoding inositol-mono-phosphatase from Alicyclobacillus acidocaldarius

<400> SEQUENCE: 35

| | |
|---|---|
| atggacaagg catggctcga tggcctggcg gaggtcgtgc gggaggctgg ccgcctggtg | 60 |
| gaggagatcg ccaggcaggg cttcgatacg caattcaagc atccggaaga gaggcgagat | 120 |
| ccggtcacga cagccgatct cgcctgtgac gcgtttctga aagagcggct gctcacgctg | 180 |
| cttccggagg cgggctggct gtccgaggag acgaaggatc ggccggatcg attggagaaa | 240 |
| aggtgggtgt ggatcgtcga tcccatcgac ggcacgcggg agttcgtccg ccgcattccc | 300 |
| gagtacgcca tctcggtggc gctcgcgcgc gacggcgagc cggtggcggg cgcggtggtg | 360 |
| aatcccgcga cggggatct gtttctcggc gccgtgggcg tcggcgcatg gcggaatgga | 420 |
| acgcccatgg tttgttcccg catccgcggc gagcggctca cgattctcgg cagccggtcg | 480 |
| gagatgaacc gcgcgagtt cgagccgttt gccggcattc tcgaggtccg ggcggtgggc | 540 |
| tccatcgcgt ataagctcgc gctcgtcgcg gcgggcgagg cggatggcac gttcagcctc | 600 |
| ggcccgaaac acgagtggga tatcgcggcc ggcgtcgcgc tcgtcctggc ggcgggcggc | 660 |
| cgggtacacg atggcgccgg gcgccccgttt cgcttcaacc agccgcacac gctcacccgt | 720 |
| ggcatcgtcg cggccacgcg cgaggcgtat ggcgatctcg ccctgctcat cgagcggcac | 780 |

```
gccccacggc gcgcctag                                                 798
```

<210> SEQ ID NO 36
<211> LENGTH: 777
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Meiothermus silvanus

<400> SEQUENCE: 36

```
atggacttgc aacgctactt ggaagccgca ctcgatgctg cgtacttggc tcgaggcatc    60
cacctctact accgcgaaaa aggcttcgcc ctggagagca aaaccagtcc caccgacttg   120
gtcacccaag ccgaccggga gagcgaagaa gctatccgga gtttactgct cgagcgcttc   180
cccgatcatg tggtgctggg tgaagaaggt gggcaggaag ccacagcga ttttcgctgg   240 atcgtggacc cgctcgacgg cacggtcaac tacgcccacg gcttcccctt ctacgcggta   300
agcatcgccc tcgaggtggg gggcgaggtc gtggtggggg cagtgctgga caccgcacgg   360
ggcgagctgt ttaccgccct caaaggagag ggagcattcc aaaatggacg ccccattcgc   420
gtttcgagca ccgcgaccct catcggaagc ctgctggcaa ccggcttccc ctacgatgtg   480
gccaaggacg ccgagaacct gacctacttc agcgggctc ttgccaaagg ccttaccgtg   540
cgccgccccg gagccgccgc gctggatttg gcttacgtgg cggcagggcg gctggagggt   600
ttctgggagg tcaagctcaa cccctgggac gtggccgcgg gctggctcct catcaccgag   660
gcgggcggaa ccgtgagcgg catccagggc gagccttacc ggctaggaaa ccgctacttg   720
gtagccagca acgggaagat tcatgagcag ctcctcgaca cgctccacgg gcgatga      777
```

<210> SEQ ID NO 37
<211> LENGTH: 777
<212> TYPE: DNA
<213> ORGANISM: Artificial Sequence
<220> FEATURE:
<223> OTHER INFORMATION: Nucleotide sequence encoding psicose-6-
      phosphate phosphatase Nucleotide sequence encoding inositol-mono-
      phosphatase from Meiothermus rufus

<400> SEQUENCE: 37

```
atggatctgc gtccctacct cgaggccgct ctcgatgcgg cctacctagc caaaggcatt    60
caccagtact accaggaaaa aggcttcacc cacagcacca aatctacccc taccgatgtg   120
gtcacccagg ccgaccacga ggccgaggca gccatccggg tcttatcgc cgagcgcttc   180 cccgaccacg tggtgttagg cgaggagcag ggccaggaag ggagggcga gtttcgctgg   240 attgtagacc ccttggatgg cacggtgaac tacgcccacg gctttcccctt ctatggggtg   300 agcatcgggc tggaggtacg aggagaggtg gtgttggggg tggtgctgga taccgcccgg   360
ggcgatctct tcaccgctac caaaggcggc gggcctacc tgaatggccg cccgctgcgg   420
gtttcccagc gaaccacttt ggtgggcagt ctgctggcta ccggttttcc ctacgatgtg   480
gcacgagacc cggagaacct cacctacttc agcgggctt tggccaaggg gctgaccgtg   540
cggcggcccg gggcagcggc cctcgacctg gccaatgtgg ccgcgggccg gctggacggt   600
ttctgggagg ttaagctcaa cccctgggat gtggctgcgg gctggctcct catcaccgag   660
gcaggcggcc aggtcaccgg gttccagggc gaggcctacc gcctgggtaa ccgctatta   720 gtggcctcca atgggcggat tcaccaggcg ctgctcgagg cccttcaggg ccgatag      777
```

<210> SEQ ID NO 38
<211> LENGTH: 777
<212> TYPE: DNA
<213> ORGANISM: Artificial Sequence
<220> FEATURE:
<223> OTHER INFORMATION: Nucleotide sequence encoding psicose-6-
phosphate phosphatase Nucleotide sequence encoding inositol-mono-
phosphatase from Meiothermus taiwanensis

<400> SEQUENCE: 38

```
atggacttgc gtgcctacct gcaaaccgcc ctcgacgccg cctatttagc caaaggcatc      60
caccagtact accaggaaaa aggctttacc cagagcagca agtccacccc caccgatctg     120
gtcacccagg ccgaccacga gtcggaggcg gccatccgag aactcatcgc cgcgcgccac     180
cccgaccacg tggtgctggg cgaggagcag ggccaggaca agaaggggc cttccgctgg      240
attgtagacc ccctggacgg caccgtaaac tacgcccatg gttttccttt ttatgcggtg     300
agcattggcc tggaagccca cggcgaggtg gtgctggggg tggttctgga taccgctcga     360
ggcgagctgt ttaccgctac caaaggggt ggggcttacc tgaacggtcg tcccatccgg      420
gtttccactc gttcaaccct ggtgggcagc ctcctggcca ccggatttcc ctacgacgta     480
agcaaggata ccgaaaacct gacctacttc agcgggcat tgaccaaagg ctcatggta      540
cggcgccccg gcgcggcggc cctcgacctg gcctatgtgg ccgccgggcg cctggacggc     600
ttctgggagg tgaagctgaa ccctggggac gtggccgcgg gctggctcat cgtcagtgag     660
gcggggggc gggtaagcgg ccttcagggc gaggattacc ggctgggcaa ccgctacctg      720
gtggcctcca acggcctaat tcatcagccc ttgctggaca ccctccacgg gcgatag        777
```

<210> SEQ ID NO 39
<211> LENGTH: 777
<212> TYPE: DNA
<213> ORGANISM: Artificial Sequence
<220> FEATURE:
<223> OTHER INFORMATION: Nucleotide sequence encoding psicose-6-
phosphate phosphatase Nucleotide sequence encoding inositol-mono-
phosphatase from Meiothermus chliarophilus

<400> SEQUENCE: 39

```
atggacctgc gccccttcct cgagaccgcg ctcgccgcgg cttacgtggc tcgaggcatc      60
caccagctct accaggacaa aggcttcacc cagagcacca agtccacccc caccgacgtc     120
gtgacccaag ccgacaagga ggccgaggcc gccatccgcg ccctcatcga gcagcggcac     180
cccggccacg tggtgctcgg cgaggaggag ggccagcagg gcgagggcga gtaccgctgg     240
atcgtggacc cgctcgacgg caccgtgaat tacgcccacg gcttcccctt ctactgcgtg     300
agcatcgggc tcgaggtgcg cggcgaggtg atggtgggcg tggtgctcga caccgcccgc     360
ggcgacctct tcaccgcgac ccgcggcggc ggggcctact tcaacgggcg gcccatgcgg     420
gtctcgcggt cgcccaagct gctgggcagc ctcatcgcca ccggcttccc ctacgacgtc     480
gcccgcgacc gcgaaaacct gacctacctc gagcgcgtcc tcttcaaggg catcaccgtg     540
cgccgccccg gcgccgccgc cctcgacctc gcctacgtgg cctgcgggcg gctcgacggc     600
ttctgggagg tcaagctcaa ccctggggac gtggcggcgg gctggctgct ggtcgaggag     660
gcgggcggca ggatcaccgg catccacggc gagccctacc gcatgggcaa ccgctacctc     720
atggcctcca acggccacat ccacgaggaa ttgctggcga cgatccacgg ccggtag        777
```

<210> SEQ ID NO 40
<211> LENGTH: 777

<212> TYPE: DNA
<213> ORGANISM: Artificial Sequence
<220> FEATURE:
<223> OTHER INFORMATION: Nucleotide sequence encoding psicose-6-phosphate phosphatase Nucleotide sequence encoding inositol-mono-phosphatase from Meiothermus cerbereus

<400> SEQUENCE: 40

```
atggacttgc gtgtatacct gcagaccgcc ctcgatgcag cctatctggc caaaggcatt      60
caccagtact accaggagaa gggttttacc ctaagcagca agtccacccc cacagacctg     120
gttactcagg ccgaccacga gtcggaagcg gccatccgag aactcattgc cgcgcgccac     180
cccgaccacg tggtgctggg agaggagcag ggccaggaca gagaagggc ttttcgctgg      240
attgtagacc ccctggatgg caccgtaaac tacgcccacg gttttcccctt ttatgcggtg    300
agtatcggcc tcgaggccca cggcgaggtg gtgctgggag tgattctcga taccgcccgg    360
ggcgacctat tcaccgctac caaggggggc ggggccttca tgaatggccg ccccatccgg    420
gtttcccctc gagccaccct ggtgggaagc ctgctggcca ccggcttccc ctatgacgtt    480
agcaaagaca ccgaaaacct ggtctacttc agcgggccc tgaccagagg gcttatggtg     540
cggcgtcccg cgcgctgccgc cctcgacctg gcctacgtgg ccgccgggcg tctggatggt    600
ttctgggagg tgaagctcaa ccccctgggat gtggccgcag gctggctcat catccgcgag   660
gccgggggta cggttacggg catggagggg gaggcctacc ggctgggcaa ccgctacctg    720
gtagcctcca acggcctgat tcaccagcct ctgctggaca ccatacacgg gcgatag      777
```

<210> SEQ ID NO 41
<211> LENGTH: 26
<212> TYPE: DNA
<213> ORGANISM: Artificial Sequence
<220> FEATURE:
<223> OTHER INFORMATION: PCR primer; Forward primer DNA sequence for amplifying inositol-mono-phosphatase gene from Rhodothermus marinus

<400> SEQUENCE: 41

```
ctccgccata tgatggatgc ctacac                                          26
```

<210> SEQ ID NO 42
<211> LENGTH: 25
<212> TYPE: DNA
<213> ORGANISM: Artificial Sequence
<220> FEATURE:
<223> OTHER INFORMATION: PCR primer; Reverse primer DNA sequence for amplifying inositol-mono-phosphatase gene from Rhodothermus marinus

<400> SEQUENCE: 42

```
gccacctcga gggcgtagac gtggt                                           25
```

<210> SEQ ID NO 43
<211> LENGTH: 33
<212> TYPE: DNA
<213> ORGANISM: Artificial Sequence
<220> FEATURE:
<223> OTHER INFORMATION: PCR primer; Forward primer DNA sequence for amplifying inositol-mono-phosphatase gene from Thermotoga lettingae

<400> SEQUENCE: 43

```
gtgcaaatca tatggacaga atggattttt caa                                  33
```

<210> SEQ ID NO 44

```
<211> LENGTH: 34
<212> TYPE: DNA
<213> ORGANISM: Artificial Sequence
<220> FEATURE:
<223> OTHER INFORMATION: PCR primer; Reverse primer DNA sequence for
      amplifying inositol-mono-phosphatase gene from Thermotoga
      lettingae

<400> SEQUENCE: 44
gatattctcg agtttctta cttttttatt cacc                            34

<210> SEQ ID NO 45
<211> LENGTH: 27
<212> TYPE: DNA
<213> ORGANISM: Artificial Sequence
<220> FEATURE:
<223> OTHER INFORMATION: PCR primer; Forward primer DNA sequence for
      amplifying inositol-mono-phosphatase gene from Meiothermus ruber

<400> SEQUENCE: 45 tgacccata tggacttgcg tgcctat                                    27

<210> SEQ ID NO 46
<211> LENGTH: 25
<212> TYPE: DNA
<213> ORGANISM: Artificial Sequence
<220> FEATURE:
<223> OTHER INFORMATION: PCR primer; Reverse primer DNA sequence for
      amplifying inositol-mono-phosphatase gene from Meiothermus ruber

<400> SEQUENCE: 46
ttctgcctcg agtcgcccgt ggatg                                     25

<210> SEQ ID NO 47
<211> LENGTH: 34
<212> TYPE: DNA
<213> ORGANISM: Artificial Sequence
<220> FEATURE:
<223> OTHER INFORMATION: PCR primer; Forward primer DNA sequence for
      amplifying inositol-mono-phosphatase gene from Dictyoglomus
      turgidum

<400> SEQUENCE: 47
taagctcata tgaagagaat acttgaagta gcta                           34

<210> SEQ ID NO 48
<211> LENGTH: 34
<212> TYPE: DNA
<213> ORGANISM: Artificial Sequence
<220> FEATURE:
<223> OTHER INFORMATION: PCR primer; Reverse primer DNA sequence for
      amplifying inositol-mono-phosphatase gene from Dictyoglomus
      turgidum

<400> SEQUENCE: 48
acaaaagact cgagaaattt ttcatttcta atga                           34

<210> SEQ ID NO 49
<211> LENGTH: 34
<212> TYPE: DNA
<213> ORGANISM: Artificial Sequence
<220> FEATURE:
<223> OTHER INFORMATION: PCR primer; Forward primer DNA sequence for
      amplifying inositol-mono-phosphatase gene from Meiothermus
      silvanus

<400> SEQUENCE: 49
atatacatat ggacttgcaa cgctacttgg aagc                           34
```

<210> SEQ ID NO 50
<211> LENGTH: 31
<212> TYPE: DNA
<213> ORGANISM: Artificial Sequence
<220> FEATURE:
<223> OTHER INFORMATION: PCR primer; Reverse primer DNA sequence for
amplifying inositol-mono-phosphatase gene from Meiothermus
silvanus

<400> SEQUENCE: 50
tggtggtcga ctcgcccgtg gagcgtgtcg a                                  31

<210> SEQ ID NO 51
<211> LENGTH: 34
<212> TYPE: DNA
<213> ORGANISM: Artificial Sequence
<220> FEATURE:
<223> OTHER INFORMATION: PCR primer; Forward primer DNA sequence for
amplifying inositol-mono-phosphatase gene from Meiothermus rufus

<400> SEQUENCE: 51
atatacatat ggatctgcgt ccctacctcg aggc                               34

<210> SEQ ID NO 52
<211> LENGTH: 30
<212> TYPE: DNA
<213> ORGANISM: Artificial Sequence
<220> FEATURE:
<223> OTHER INFORMATION: PCR primer; Reverse primer DNA sequence for
amplifying inositol-mono-phosphatase gene from Meiothermus rufus

<400> SEQUENCE: 52
tggtggtcga ctcggccctg aagggcctcg                                    30

<210> SEQ ID NO 53
<211> LENGTH: 34
<212> TYPE: DNA
<213> ORGANISM: Artificial Sequence
<220> FEATURE:
<223> OTHER INFORMATION: PCR primer; Forward primer DNA sequence for
amplifying inositol-mono-phosphatase gene from Meiothermus
taiwanensis

<400> SEQUENCE: 53
atatacatat ggacttgcgt gcctacctgc aaac                               34

<210> SEQ ID NO 54
<211> LENGTH: 31
<212> TYPE: DNA
<213> ORGANISM: Artificial Sequence
<220> FEATURE:
<223> OTHER INFORMATION: PCR primer; Reverse primer DNA sequence for
amplifying inositol-mono-phosphatase gene from Meiothermus
taiwanensis

<400> SEQUENCE: 54
tggtggtcga ctcgcccgtg gagggtgtcc a                                  31

<210> SEQ ID NO 55
<211> LENGTH: 34
<212> TYPE: DNA
<213> ORGANISM: Artificial Sequence
<220> FEATURE:
<223> OTHER INFORMATION: PCR primer; Forward primer DNA sequence for
amplifying inositol-mono-phosphatase gene from Meiothermus
chliarophilus

<400> SEQUENCE: 55
atatacatat ggacctgcgc cccttcctcg agac                        34

<210> SEQ ID NO 56
<211> LENGTH: 31
<212> TYPE: DNA
<213> ORGANISM: Artificial Sequence
<220> FEATURE:
<223> OTHER INFORMATION: PCR primer; Reverse primer DNA sequence for
      amplifying inositol-mono-phosphatase gene from Meiothermus
      chliarophilus

<400> SEQUENCE: 56
tggtggtcga cccggccgtg gatcgtcgcc a                           31

<210> SEQ ID NO 57
<211> LENGTH: 34
<212> TYPE: DNA
<213> ORGANISM: Artificial Sequence
<220> FEATURE:
<223> OTHER INFORMATION: PCR primer; Forward primer DNA sequence for
      amplifying inositol-mono-phosphatase gene from Meiothermus
      cerbereus

<400> SEQUENCE: 57
atatacatat ggacttgcgt gtatacctgc agac                        34

<210> SEQ ID NO 58
<211> LENGTH: 31
<212> TYPE: DNA
<213> ORGANISM: Artificial Sequence
<220> FEATURE:
<223> OTHER INFORMATION: PCR primer; Reverse primer DNA sequence for
      amplifying inositol-mono-phosphatase gene from Meiothermus
      cerbereus

<400> SEQUENCE: 58
tggtggtcga ctcgcccgtg tatggtgtcc a                           31

<210> SEQ ID NO 59
<211> LENGTH: 823
<212> TYPE: PRT
<213> ORGANISM: Artificial Sequence
<220> FEATURE:
<223> OTHER INFORMATION: ??-glucan phosphorylase; Amino acid sequence of
      ??-glucan phosphorylase from Thermotoga neapolitana (CT1)

<400> SEQUENCE: 59

Met Leu Lys Lys Leu Pro Glu Asn Leu Glu His Leu Glu Glu Leu Ala
1               5                   10                  15

Tyr Asn Leu Trp Trp Ser Trp Ser Arg Pro Ala Gln Arg Leu Trp Arg
            20                  25                  30

Lys Ile Asp Pro Glu Gly Trp Glu Glu His Arg Asn Pro Val Lys Ile
        35                  40                  45

Leu Lys Glu Val Ser Asp Glu Arg Leu Glu Glu Leu Ser Lys Asp Asp
    50                  55                  60

Asp Phe Ile Ser Leu Tyr Glu Leu Thr Ile Glu Arg Phe Lys Asp Tyr
65                  70                  75                  80

Met Glu Lys Glu Asp Thr Trp Phe Asn Val Asn Tyr Pro Glu Trp Asp
                85                  90                  95

Glu Lys Ile Val Tyr Met Cys Met Glu Tyr Gly Leu Thr Lys Ala Leu
            100                 105                 110

Pro Ile Tyr Ser Gly Gly Leu Gly Ile Leu Ala Gly Asp His Leu Lys

```
              115                 120                 125
Ser Ala Ser Asp Leu Gly Leu Pro Leu Ile Ala Ile Gly Leu Leu Tyr
            130                 135                 140
Lys His Gly Tyr Phe Thr Gln Gln Ile Asp Arg Asp Gly Lys Gln Ile
145                 150                 155                 160
Glu Ile Phe Pro Asp Tyr Asn Pro Glu Asp Leu Pro Met Lys Pro Leu
                    165                 170                 175
Lys Asp Glu Lys Gly Asn Gln Val Ile Val Glu Val Pro Leu Asp Ser
                180                 185                 190
Thr Val Val Lys Ala Arg Val Phe Glu Val Lys Val Gly Arg Val Ser
            195                 200                 205
Leu Tyr Leu Leu Asp Pro Asp Ile Glu Glu Asn Glu Glu Arg Tyr Arg
        210                 215                 220
Lys Ile Cys Asn Tyr Leu Tyr Asn Pro Glu Pro Asp Val Arg Val Ser
225                 230                 235                 240
Gln Glu Ile Leu Leu Gly Ile Gly Gly Met Lys Leu Leu Arg Ala Leu
                    245                 250                 255
Asn Leu Lys Pro Gly Val Ile His Leu Asn Glu Gly His Pro Ala Phe
                260                 265                 270
Ser Ser Leu Glu Arg Ile Lys Asn Tyr Met Glu Glu Gly Tyr Ser Phe
            275                 280                 285
Thr Glu Ala Leu Glu Ile Val Arg Gln Thr Ser Val Phe Thr Thr His
        290                 295                 300
Thr Pro Val Pro Ala Gly His Asp Arg Phe Pro Phe Asp Leu Val Glu
305                 310                 315                 320
Lys Lys Leu Ser Lys Phe Phe Glu Gly Phe Glu Lys Arg Asn Leu Leu
                    325                 330                 335
Met Asp Leu Gly Lys Asp Glu Thr Gly Ser Phe Asn Met Thr Tyr Leu
                340                 345                 350
Ala Leu Arg Thr Ser Ser Phe Ile Asn Gly Val Ser Lys Leu His Ala
            355                 360                 365
Glu Val Ser Arg Arg Met Phe Lys Asn Val Trp Gln Gly Val Pro Val
        370                 375                 380
Glu Glu Ile Pro Ile Glu Gly Ile Thr Asn Gly Val His Met Gly Thr
385                 390                 395                 400
Trp Ile Asn Arg Glu Met Arg Lys Leu Tyr Asp Arg Tyr Leu Gly Arg
                    405                 410                 415
Val Trp Arg Asp His Thr Asp Leu Glu Gly Ile Trp Tyr Gly Val Asp
                420                 425                 430
Arg Ile Pro Asp Glu Glu Leu Trp Gln Ala His Leu Arg Ala Lys Lys
            435                 440                 445
Arg Phe Ile Glu Tyr Ile Lys Glu Ser Val Arg Arg Asn Glu Arg
        450                 455                 460
Leu Gly Ile Asp Glu Asp Val Pro Asn Ile Asp Glu Asn Ser Leu Ile
465                 470                 475                 480
Ile Gly Phe Ala Arg Arg Phe Ala Thr Tyr Lys Arg Ala Val Leu Leu
                    485                 490                 495
Leu Ser Asp Leu Glu Arg Leu Lys Lys Ile Leu Asn Asp Pro Glu Arg
                500                 505                 510
Pro Val Tyr Val Val Tyr Ala Gly Lys Ala His Pro Arg Asp Asp Ala
            515                 520                 525
Gly Lys Glu Phe Leu Lys Arg Ile Tyr Glu Val Ser Gln Met Pro Glu
        530                 535                 540
```

Phe Lys Asn Arg Ile Ile Val Leu Glu Asn Tyr Asp Ile Gly Met Ala
545                 550                 555                 560

Arg Leu Met Val Ser Gly Val Asp Val Trp Leu Asn Asn Pro Arg Arg
            565                 570                 575

Pro Met Glu Ala Ser Gly Thr Ser Gly Met Lys Ala Ala Ala Asn Gly
        580                 585                 590

Val Leu Asn Ala Ser Val Tyr Asp Gly Trp Val Glu Gly Tyr Asn
    595                 600                 605

Gly Arg Asn Gly Trp Val Ile Gly Asp Glu Ser Val Leu Pro Glu Thr
        610                 615                 620

Glu Val Asp Asp Pro Arg Asp Ala Glu Ala Leu Tyr Asp Leu Leu Glu
625                 630                 635                 640

Asn Glu Ile Ile Pro Thr Tyr Tyr Glu Asn Lys Glu Lys Trp Ile Phe
            645                 650                 655

Met Met Lys Glu Ser Ile Lys Ser Val Ala Pro Arg Phe Ser Thr Thr
            660                 665                 670

Arg Met Leu Lys Glu Tyr Thr Glu Lys Phe Tyr Ile Lys Gly Leu Val
        675                 680                 685

Asn Lys Glu Trp Leu Arg Lys Glu Asn Ala Glu Arg Phe Gly Ala
    690                 695                 700

Trp Lys Glu Arg Ile Leu Arg Asn Trp Ser Ser Val Ser Ile Glu Arg
705                 710                 715                 720

Ile Val Leu Glu Asp Thr Arg Ser Val Glu Val Thr Val Lys Leu Gly
            725                 730                 735

Asp Leu Ser Pro Asp Asp Val Leu Val Glu Leu Leu Ile Gly Arg Gly
            740                 745                 750

Glu Ser Met Glu Asp Leu Glu Ile Trp Lys Val Ile Gln Ile Arg Lys
        755                 760                 765

His Arg Arg Glu Gly Asp Leu Phe Ile Tyr Ser Tyr Val Asn Gly Ala
        770                 775                 780

Leu Gly His Leu Gly Ser Pro Gly Trp Phe Tyr Ala Val Arg Val Leu
785                 790                 795                 800

Pro Tyr His Pro Lys Leu Pro Thr Arg Phe Leu Pro Glu Ile Pro Val
            805                 810                 815

Val Trp Lys Lys Val Leu Gly
            820

<210> SEQ ID NO 60
<211> LENGTH: 2472
<212> TYPE: DNA
<213> ORGANISM: Artificial Sequence
<220> FEATURE:
<223> OTHER INFORMATION: ??-glucan phosphorylase; Nucleotide sequence
      encoding ??-glucan phosphorylase from Thermotoga neapolitana(CT1)

<400> SEQUENCE: 60
atgctgaaga aactcccgga gaatctggag catctggaag aactcgccta caacctctgg      60
tggagctggt ctaggcccgc tcagagactc tggagaaaga tagatccgga aggctgggag     120
gaacacagaa accccgttaa aatactgaaa gaagtttctg atgaaaggct cgaagaactt     180
tcaaaagatg atgatttcat atccctctac gaactcacca ttgaaaggtt caaggattac     240
atggagaaag aagacacctg gttcaacgtg aactacccCg aatgggacga gaagatcgtc     300
tacatgtgta tggagtacgg tttgaccaaa gcccttccga tctactccgg tggtcttgga     360
atcctcgcgg gagaccatct caaatccgca agcgatcttg acttcctct catagcgatc     420

```
ggacttctct acaaacatgg atatttcacc cagcagatcg acagagatgg aaaacagata      480
gagattttcc ctgattacaa cccagaggac ttacccatga agcccctgaa ggatgaaaag      540
ggaaaccagg tgatcgtgga ggttcctctc gacagtaccg tggtgaaggc acgtgttttt      600
gaagtgaagg taggaagggt gagtctgtac ctgctcgatc cggacatcga ggaaaacgag      660
gaacgataca gaaagatctg caactacctt tacaacccgg aacccgatgt gagggtctcc      720
caggagatac tcctcggaat tgggggaatg aagcttctca gggctctgaa cctgaaacca      780
ggagtcatcc atctgaacga aggacatccg gcgttctctt ccctcgaaag gataaagaac      840
tacatggaag aaggatattc cttcacagag gcccttgaga tcgtgagaca gacgagtgtg      900
tttacaaccc acacacccgt tcccgctgga cacgacagat ttccctttga cctcgtggaa      960
aagaaacttt cgaaattctt cgaaggattc gaaaagagaa atcttctcat ggatcttggg     1020
aaagatgaaa caggcagttt caacatgacg tatcttgccc tgagaacgtc ctctttcata     1080
aacggcgtga gcaaactgca tgcggaagtt tccagaagga tgttcaaaaa cgtgtggcag     1140
ggtgttcccg tggaggaaat accgatcgaa gggataacga acggcgttca catgggaacc     1200
tggatcaacc gtgagatgag aaaactgtac gacagatatc tcggaagggt atggagagat     1260
cacaccgacc ttgagggtat ctggtacggt gttgacagga ttccagatga agaactctgg     1320
caggctcacc tgagggcaaa gaagagattc atcgagtaca taaagaatc ggtaagaaga      1380 agaaacgaga gactgggaat cgacgaagat gtgccgaaca tcgatgaaaa ttcgctcatc     1440
ataggttttg caagaaggtt tgccacttac aagagggcag ttctcctgct cagcgatctg     1500
gagagactca agaagatcct caacgatcca gaaagacccg tttacgtggt ctatgcgggg     1560
aaggcccatc caagggacga tgcggggaag gaattttga  aacgcatcta cgaagtctcg      1620
cagatgcctg agttcaaaaa caggatcatc gtactggaaa actacgacat ggaatggca      1680 cggctcatgg tgtcgggagt ggatgtgtgg ctgaacaacc cgagaagacc catggaagca     1740
agtggaacaa gcggaatgaa ggcagcagcc aacggagttc ttaacgcgag tgtttacgat     1800
ggatggtggg ttgaagggta caacggcaga acggctggg  tcataggcga tgaaagcgtt      1860
cttccagaga cggaagtgga cgatcccagg gacgcagaag cactctacga tctcctcgaa     1920
aacgaaatca tcccaaccta ctacgaaaac aaagaaagt  ggatcttcat gatgaaagag      1980
agcataaaga gtgttgctcc aagattcagc accaccagaa tgctcaaaga atacacggag     2040
aagttctaca taaagggact tgtgaacaaa gaatggcttg aaagaaaaga aaacgccgaa     2100
aggtttggtg catggaagga aaggatcctc agaaactgga gcagcgtttc catagaaaga     2160
atcgtccttg aggacacaag gagtgttgag gtgacggtga aactgggaga cctttcacct     2220
gatgatgtac tggttgaact tttgattgga agaggagaaa gcatgaaga  tctggagatc      2280 tggaaggtga tacagataag aaagcacaga agggaagggg atctgttcat ctacagttat     2340
gtcaacggtg ccctcggtca tcttggctct ccgggatggt tctacgcggt gagggtgcta     2400
ccttatcatc cgaaacttcc caccagattc ttgccggaga tacctgtggt gtggaaaaag     2460
gttctcgggt ga                                                          2472
```

<210> SEQ ID NO 61
<211> LENGTH: 441
<212> TYPE: PRT
<213> ORGANISM: Artificial Sequence
<220> FEATURE:
<223> OTHER INFORMATION: phosphoglucomutase; Amino acid sequence of phosphoglucomutase from Thermotoga neapolitana (CT2)

<400> SEQUENCE: 61

```
Met Ile Gly Tyr Gln Ile Tyr Val Arg Ser Phe Arg Asp Gly Asn Phe
1               5                   10                  15

Asp Gly Val Gly Asp Phe Lys Gly Leu Lys Gly Ala Ile Ser Tyr Leu
            20                  25                  30

Lys Glu Leu Gly Val Asp Phe Val Trp Leu Met Pro Val Phe Ser Ser
        35                  40                  45

Ile Ser Phe His Gly Tyr Asp Val Val Asp Phe Tyr Ser Phe Lys Ala
    50                  55                  60

Glu Tyr Gly Asp Glu Lys Asp Phe Arg Glu Met Ile Glu Ala Phe His
65                  70                  75                  80

Asp Asn Gly Ile Lys Val Val Leu Asp Leu Pro Ile His His Thr Gly
                85                  90                  95

Phe Leu His Val Trp Phe Gln Lys Ala Leu Lys Gly Asp Pro His Tyr
            100                 105                 110

Arg Asp Tyr Tyr Val Trp Ala Ser Glu Lys Thr Asp Leu Asp Glu Arg
        115                 120                 125

Arg Glu Trp Asp Asn Glu Arg Ile Trp His Pro Leu Glu Asp Gly Arg
130                 135                 140

Phe Tyr Arg Gly Leu Phe Gly Pro Leu Ser Pro Asp Leu Asn Tyr Asp
145                 150                 155                 160

Asn Pro Gln Val Phe Glu Glu Met Lys Lys Val Val Tyr His Leu Leu
                165                 170                 175

Glu Met Gly Val Asp Gly Phe Arg Phe Asp Ala Ala Lys His Met Arg
            180                 185                 190

Asp Thr Leu Glu Gln Asn Val Arg Phe Trp Arg Tyr Phe Leu Ser Asp
        195                 200                 205

Ile Glu Gly Ile Phe Leu Ala Glu Ile Trp Ala Glu Ser Lys Val Val
    210                 215                 220

Asp Glu His Gly Arg Ile Phe Gly Tyr Met Leu Asn Phe Asp Thr Ser
225                 230                 235                 240

His Cys Ile Lys Glu Ala Val Trp Lys Glu Asn Phe Lys Val Leu Ile
                245                 250                 255

Glu Ser Ile Glu Arg Ala Leu Val Gly Lys Asp Tyr Leu Pro Val Asn
            260                 265                 270

Phe Thr Ser Asn His Asp Met Ser Arg Leu Ala Ser Phe Glu Gly Gly
        275                 280                 285

Leu Ser Glu Glu Lys Val Lys Leu Ser Leu Ser Ile Leu Phe Thr Leu
    290                 295                 300

Pro Gly Val Pro Leu Ile Phe Tyr Gly Asp Glu Leu Gly Met Lys Gly
305                 310                 315                 320

Ile Tyr Arg Lys Pro Asn Thr Glu Val Val Leu Asp Pro Phe Pro Trp
                325                 330                 335

Ser Glu Asn Met Cys Val Glu Gly Gln Thr Phe Trp Lys Trp Pro Ala
            340                 345                 350

Tyr Asn Asp Pro Phe Ser Gly Val Ser Val Glu Tyr Gln Arg Arg Asn
        355                 360                 365

Arg Asp Ser Ile Leu Ser His Thr Met Arg Trp Ala Gly Phe Arg Gly
    370                 375                 380

Glu Asn His Trp Leu Asp Arg Ala Asn Ile Glu Phe Leu Cys Lys Glu
385                 390                 395                 400

Glu Lys Leu Leu Val Tyr Arg Leu Val Asp Glu Gly Arg Ser Leu Lys
```

```
                405                 410                 415
Val Ile His Asn Leu Ser Asn Gly Glu Met Val Phe Glu Gly Val Arg
            420                 425                 430

Val Gln Pro Tyr Ser Thr Glu Val Val
            435                 440

<210> SEQ ID NO 62
<211> LENGTH: 1326
<212> TYPE: DNA
<213> ORGANISM: Artificial Sequence
<220> FEATURE:
<223> OTHER INFORMATION: phosphoglucomutase; Nucleotide sequence
      encoding phosphoglucomutase from Thermotoga neapolitana (CT2)

<400> SEQUENCE: 62
atgataggct accagatcta cgtgagatca ttcagggatg aaacttcga tggtgtgggg      60 gatttcaaag gattgaaagg tgcgatttcc tacctgaaag aactgggtgt tgattttgtc    120
tggctcatgc ccgtcttttc ctccatttcc ttccacgggt atgacgtggt ggattttat    180 tctttcaaag ccgagtacgg agacgagaaa gactttagag agatgatcga ggcgttccac    240
gacaacggta taaaagtcgt tctcgatctt cccatccatc atactggttt cctccatgtg    300
tggtttcaga aagccctgaa aggagatcca cactacaggg attattacgt atgggcgagt    360
gaaaaaacgg atctggacga agaagagag tgggacaacg aaaggatctg catcctctg     420 gaggacggaa ggttctacag aggactttc ggtcccctct cacccgatct gaactacgat    480
aacccgcagg tttttgaaga gatgaagaag gtggtttatc accttcttga atgggagtg    540 gacggattca gattcgacgc agcaaagcac atgagagata ctctggaaca gaacgttcgc    600
ttttggaggt atttcctctc cgatattgag ggaatattcc ttgcggaaat ctgggcagaa    660
tccaaagttg tggatgaaca cggcaggata ttcggctaca tgctaaattt cgatacctca    720
cactgtatta aggaagcggt gtggaaggaa aacttcaaag tgttgatcga gtcgatcgaa    780
agggccctgg ttggaaaaga ttatctgccg gtgaacttca catcgaacca tgatatgtca    840
aggcttgcga gtttcgaagg agggttgagt gaagagaagg tgaaactctc actttccatt    900
ctgttcacgc ttcccgggt tcctctcata ttctacggag acgaactggg aatgaaagga    960
atctatcgaa aaccgaacac ggaagtcgtg ctggatccgt tcccctggag cgaaaacatg   1020
tgtgttgaag gccagacatt ttggaaatgg cccgcgtata cgatccatt ctccggtgtt    1080 tctgttgagt atcagaggag aaatcgtgat tcgattctct cacacacgat gaggtgggca   1140
ggattcagag gggaaaatca ctggctggac agggcaaaca tcgaatttct gtgcaaagaa   1200
gaaaaactgc tcgtgtacag actggtcgat gaagggcgtt ctctgaaagt gatacacaac   1260
ctgtcgaatg gtgaaatggt gtttgaggga gtgcgcgtac aaccctacag cacggaggtg   1320
gtttga                                                              1326

<210> SEQ ID NO 63
<211> LENGTH: 451
<212> TYPE: PRT
<213> ORGANISM: Artificial Sequence
<220> FEATURE:
<223> OTHER INFORMATION: D-glucose-6-phosphate-isomerase; Amino acid
      sequence of D-glucose-6-phosphate-isomerase (TN1)

<400> SEQUENCE: 63

Met Lys Lys Met Ala Leu Lys Phe Asp Phe Ser Asn Leu Phe Glu Pro
1               5                   10                  15
```

```
Asn Ile Ser Gly Gly Leu Arg Glu Glu Asp Leu Glu Ser Thr Lys Glu
             20                  25                  30

Lys Val Ile Glu Ala Ile Lys Asn Phe Thr Glu Asn Thr Pro Asp Phe
         35                  40                  45

Ala Arg Leu Asp Arg Lys Trp Ile Asp Ser Val Lys Glu Leu Glu Glu
     50                  55                  60

Trp Val Val Asn Phe Asp Thr Val Val Leu Gly Ile Gly Gly Ser
 65                  70                  75                  80

Gly Leu Gly Asn Leu Ala Leu His Tyr Ser Leu Arg Pro Leu Asn Trp
                 85                  90                  95

Asn Glu Met Ser Arg Glu Arg Asn Gly Tyr Ala Arg Val Phe Val
            100                 105                 110

Val Asp Asn Val Asp Pro Asp Leu Met Ala Ser Val Leu Asp Arg Ile
        115                 120                 125

Asp Leu Lys Thr Thr Leu Phe Asn Val Ile Ser Lys Ser Gly Ser Thr
130                 135                 140

Ala Glu Val Met Ala Asn Tyr Ser Ile Ala Arg Gly Ile Leu Glu Ala
145                 150                 155                 160

Asn Gly Leu Asp Pro Lys Glu His Ile Leu Ile Thr Thr Asp Pro Glu
                165                 170                 175

Lys Gly Phe Leu Arg Lys Val Val Lys Glu Glu Gly Phe Arg Ser Leu
            180                 185                 190

Glu Val Pro Pro Gly Val Gly Arg Phe Ser Val Leu Thr Pro Val
        195                 200                 205

Gly Leu Phe Ser Ala Met Ala Glu Gly Ile Asp Ile Glu Glu Leu His
        210                 215                 220

Asp Gly Ala Arg Asp Ala Phe Glu Arg Cys Lys Lys Glu Asp Leu Phe
225                 230                 235                 240

Glu Asn Pro Ala Ala Met Ile Ala Leu Thr His Tyr Leu Tyr Leu Lys
                245                 250                 255

Arg Gly Lys Ser Ile Ser Val Met Met Ala Tyr Ser Asn Arg Met Thr
            260                 265                 270

Tyr Leu Val Asp Trp Tyr Arg Gln Leu Trp Ala Glu Ser Leu Gly Lys
        275                 280                 285

Arg Tyr Asn Leu Lys Gly Glu Glu Val Phe Thr Gly Gln Thr Pro Val
        290                 295                 300

Lys Ala Ile Gly Ala Thr Asp Gln His Ser Gln Ile Gln Leu Tyr Asn
305                 310                 315                 320

Glu Gly Pro Asn Asp Lys Val Ile Thr Phe Leu Arg Leu Glu Asn Phe
                325                 330                 335

Asp Arg Glu Ile Ile Pro Asp Thr Gly Arg Glu Glu Leu Lys Tyr
            340                 345                 350

Leu Ala Arg Lys Arg Leu Ser Glu Leu Leu Ala Glu Gln Thr Gly
        355                 360                 365

Thr Glu Glu Ala Leu Arg Lys Asn Asp Arg Pro Asn Met Lys Val Ile
        370                 375                 380

Phe Asp Arg Leu Thr Ser Tyr Asn Val Gly Gln Phe Ala Tyr Tyr
385                 390                 395                 400

Glu Ala Ala Thr Ala Phe Met Gly Tyr Leu Leu Glu Ile Asn Pro Phe
                405                 410                 415

Asp Gln Pro Gly Val Glu Leu Gly Lys Lys Ile Thr Phe Ala Leu Met
            420                 425                 430

Gly Arg Glu Gly Tyr Glu Tyr Glu Ile Lys Asp Arg Thr Lys Lys Val
```

```
                         435                 440                 445
Ile Ile Glu
    450

<210> SEQ ID NO 64
<211> LENGTH: 1356
<212> TYPE: DNA
<213> ORGANISM: Artificial Sequence
<220> FEATURE:
<223> OTHER INFORMATION: D-glucose-6-phosphate-isomerase; Nucleotide
      sequence encoding D-glucose-6-phosphate-isomerase (TN1)

<400> SEQUENCE: 64
atgaaaaaga tggctttgaa atttgatttt tcaaatcttt ttgaaccgaa catctccggt      60
ggactgagag aggaagatct ggaaagcaca aaagaaaagg tgatagaggc gataaagaat    120
ttcactgaga acacaccgga ttttgccaga ctggacagaa atggatcga ttcggtgaag     180 gaactcgagg agtgggtggt gaacttcgac acggtggtcg ttctgggaat tgggggatcc    240
ggtcttggaa accttgccct tcattattcg ttgagaccac tgaactggaa cgagatgtcg    300
agagaggaaa gaaacggtta tgcgagagtc ttcgtggtgg acaacgtaga tcccgatctc    360
atggcctccg tccttgatag gatagatctg aagacaacgc tgttcaacgt gatctcaaaa    420
tctggatcca cggctgaggt tatggcgaat tactcgatcg caaggggaat cctggaggct    480
aatggtctgg acccgaaaga acacatcctc atcacaacga tccagagaa gggcttttg     540 agaaaagtag tgaaagaaga gggcttcaga agtcttgagg tccctcccgg cgttggagga    600
aggttcagcg tgctgacgcc cgttggcctc ttctctgcca tggcgagggg tatcgacata    660
gaagaactcc acgacggtgc ccgggatgcg ttcgagagat gcaagaagga agacctgttc    720
gaaaatccag cggcgatgat cgccctcaca cactatctct atctgaagag aggaaagagc    780
atctccgtca tgatggccta ctccaacagg atgacctacc tcgtggactg gtacagacag    840
ctgtgggcag aaagtctggg aaagagatac aacctgaaag gagaggaggt cttcacgggt    900
cagaccccgg tgaaggcaat aggagccacc gatcagcact ctcagataca gctttacaac    960
gagggcccaa acgacaaagt gataacgttt ttgcggttgg aaaacttcga tagagagatc   1020
ataataccgg acaccggaag agaagagctc aaataccttg caagaaaaag actctctgaa   1080
cttctccttg cagaacagac aggaacagag gaagccctaa ggaaaaacga cagaccgaac   1140
atgaaggtga tcttcgacag actcacctct tacaatgtgg gccagttctt cgcttattat   1200
gaagccgcaa ctgctttcat ggggtatctc ctcgagatca cccgtttga tcagccgggt    1260 gtggaacttg aaagaagat cacgtttgcc ctcatgggaa gggaaggtta cgaatacgaa    1320
ataaaagatc gcaccaagaa ggtgatcata gaatga                             1356

<210> SEQ ID NO 65
<211> LENGTH: 221
<212> TYPE: PRT
<213> ORGANISM: Artificial Sequence
<220> FEATURE:
<223> OTHER INFORMATION: D-fructose-6-phosphate-3-epimerase; Amino acid
      sequence of D-fructose-6-phosphate-3-epimerase (FP3E)

<400> SEQUENCE: 65

Met Met Val Lys Ile Ala Ala Ser Ile Leu Ala Cys Asp Leu Ala Arg
1               5                   10                  15

Leu Ala Asp Glu Val Lys Arg Val Glu Glu His Ile Asp Met Val His
            20                  25                  30
```

Phe Asp Val Met Asp Gly His Phe Val Pro Asn Ile Ser Phe Gly Leu
             35                  40                  45

Pro Val Leu Lys Ala Leu Arg Lys Glu Thr Ser Leu Pro Ile Ser Val
 50                  55                  60

His Leu Met Ile Thr Asn Pro Glu Asp Tyr Val Asp Arg Phe Val Glu
 65                  70                  75                  80

Glu Gly Ala Asp Met Val Ala Val His Tyr Glu Thr Thr Pro His Leu
                 85                  90                  95

His Arg Ile Val His Arg Ile Lys Asp Leu Gly Ala Lys Ala Phe Val
            100                 105                 110

Ala Leu Asn Pro His Thr Pro Val Phe Leu Leu Ser Glu Ile Ile Thr
            115                 120                 125

Asp Val Asp Gly Val Leu Val Met Ser Val Asn Pro Gly Phe Ser Gly
130                 135                 140

Gln Arg Phe Ile Ala Arg Ser Leu Glu Lys Ile Arg Ser Leu Lys Lys
145                 150                 155                 160

Met Ile Arg Asp Leu Gly Leu Glu Thr Glu Ile Met Val Asp Gly Gly
                165                 170                 175

Val Asn Glu Glu Asn Ala Ser Ile Leu Ile Lys Asn Gly Ala Thr Ile
            180                 185                 190

Leu Val Met Gly Tyr Gly Ile Phe Lys Asn Glu Asn Tyr Val Glu Leu
            195                 200                 205

Val Arg Ser Ile Lys Gln Glu Arg Gly Glu Ser Ala Gly
            210                 215                 220

<210> SEQ ID NO 66
<211> LENGTH: 666
<212> TYPE: DNA
<213> ORGANISM: Artificial Sequence
<220> FEATURE:
<223> OTHER INFORMATION: D-fructose-6-phosphate-3-epimerase; Nucleotide
      sequence encoding D-fructose-6-phosphate-3-epimerase from
      Thermotoga neapolitana (FP3E)

<400> SEQUENCE: 66
atgatggtaa agatcgccgc ttcaatcctt gcgtgtgatc ttgcaagact cgccgatgag      60
gtaaaaaggg tggaagaaca catagacatg gttcacttcg atgtcatgga tggacacttc     120
gttccgaaca tctcgttcgg attgcccgtt ctcaaagccc tgagaaaaga aaccagcctt     180
cctataagtg ttcatctgat gatcacaaat ccagaggact atgtggaccg tttcgtggaa     240
gagggagcgg acatggtggc ggtccactac gagacaacgc cgcaccttca caggatagtg     300
cacaggataa aggatctcgg ggcgaaggcg ttcgtcgccc tcaacccaca cacccggtt      360 tttctcctgt ctgagatcat aacggatgtg gatggcgtac tcgtgatgag tgtgaacccg     420
ggcttttctg gtcagagatt cattgcaagg agtctggaaa aataaggag tctgaagaag      480 atgataaggg atctgggact cgaaacggag atcatggtcg atggtggtgt caacgaagaa     540
aacgcttcta tcttaataaa gaacggtgcg acgatccttg taatgggta cggtatcttc      600 aaaaacgaaa actatgtgga actggtgaga tccatcaagc aggaaagagg ggaatctgct     660
ggctga                                                                666

<210> SEQ ID NO 67
<211> LENGTH: 441
<212> TYPE: PRT
<213> ORGANISM: Artificial Sequence
<220> FEATURE:
<223> OTHER INFORMATION: 4-??-glucanotransferase; Amino acid sequences of 4-??-glucanotransferase (TN2)

<400> SEQUENCE: 67

```
Met Ile Gly Tyr Gln Ile Tyr Val Arg Ser Phe Arg Asp Gly Asn Phe
1               5                   10                  15

Asp Gly Val Gly Asp Phe Lys Gly Leu Lys Gly Ala Ile Ser Tyr Leu
            20                  25                  30

Lys Glu Leu Gly Val Asp Phe Val Trp Leu Met Pro Val Phe Ser Ser
        35                  40                  45

Ile Ser Phe His Gly Tyr Asp Val Val Asp Phe Tyr Ser Phe Lys Ala
    50                  55                  60

Glu Tyr Gly Asp Glu Lys Asp Phe Arg Glu Met Ile Glu Ala Phe His
65                  70                  75                  80

Asp Asn Gly Ile Lys Val Val Leu Asp Leu Pro Ile His His Thr Gly
                85                  90                  95

Phe Leu His Val Trp Phe Gln Lys Ala Leu Lys Gly Asp Pro His Tyr
            100                 105                 110

Arg Asp Tyr Tyr Val Trp Ala Ser Glu Lys Thr Asp Leu Asp Glu Arg
        115                 120                 125

Arg Glu Trp Asp Asn Glu Arg Ile Trp His Pro Leu Glu Asp Gly Arg
    130                 135                 140

Phe Tyr Arg Gly Leu Phe Gly Pro Leu Ser Pro Asp Leu Asn Tyr Asp
145                 150                 155                 160

Asn Pro Gln Val Phe Glu Glu Met Lys Lys Val Val Tyr His Leu Leu
                165                 170                 175

Glu Met Gly Val Asp Gly Phe Arg Phe Asp Ala Ala Lys His Met Arg
            180                 185                 190

Asp Thr Leu Glu Gln Asn Val Arg Phe Trp Arg Tyr Phe Leu Ser Asp
        195                 200                 205

Ile Glu Gly Ile Phe Leu Ala Glu Ile Trp Ala Glu Ser Lys Val Val
    210                 215                 220

Asp Glu His Gly Arg Ile Phe Gly Tyr Met Leu Asn Phe Asp Thr Ser
225                 230                 235                 240

His Cys Ile Lys Glu Ala Val Trp Lys Glu Asn Phe Lys Val Leu Ile
                245                 250                 255

Glu Ser Ile Glu Arg Ala Leu Val Gly Lys Asp Tyr Leu Pro Val Asn
            260                 265                 270

Phe Thr Ser Asn His Asp Met Ser Arg Leu Ala Ser Phe Glu Gly Gly
        275                 280                 285

Leu Ser Glu Glu Lys Val Lys Leu Ser Leu Ser Ile Leu Phe Thr Leu
290                 295                 300

Pro Gly Val Pro Leu Ile Phe Tyr Gly Asp Glu Leu Gly Met Lys Gly
305                 310                 315                 320

Ile Tyr Arg Lys Pro Asn Thr Glu Val Val Leu Asp Pro Phe Pro Trp
                325                 330                 335

Ser Glu Asn Met Cys Val Glu Gly Gln Thr Phe Trp Lys Trp Pro Ala
            340                 345                 350

Tyr Asn Asp Pro Phe Ser Gly Val Ser Val Glu Tyr Gln Arg Arg Asn
        355                 360                 365

Arg Asp Ser Ile Leu Ser His Thr Met Arg Trp Ala Gly Phe Arg Gly
    370                 375                 380

Glu Asn His Trp Leu Asp Arg Ala Asn Ile Glu Phe Leu Cys Lys Glu
385                 390                 395                 400
```

```
Glu Lys Leu Leu Val Tyr Arg Leu Val Asp Glu Gly Arg Ser Leu Lys
                405                 410                 415

Val Ile His Asn Leu Ser Asn Gly Glu Met Val Phe Glu Gly Val Arg
            420                 425                 430

Val Gln Pro Tyr Ser Thr Glu Val Val
        435                 440
```

<210> SEQ ID NO 68
<211> LENGTH: 1326
<212> TYPE: DNA
<213> ORGANISM: Artificial Sequence
<220> FEATURE:
<223> OTHER INFORMATION: 4-??-glucanotransferase; Nucleotide sequences
    encoding 4-??-glucanotransferase (TN2)

<400> SEQUENCE: 68

```
atgataggct accagatcta cgtgagatca ttcagggatg aaacttcga tggtgtgggg      60
gatttcaaag gattgaaagg tgcgattttcc tacctgaaag aactgggtgt tgattttgtc    120
tggctcatgc ccgtcttttc ctccattttcc ttccacgggt atgacgtggt ggattttat    180
tctttcaaag ccgagtacgg agacgagaaa gactttagag atgatcga ggcgttccac      240
gacaacggta taaaagtcgt tctcgatctt cccatccatc atactggttt cctccatgtg    300
tggtttcaga aagccctgaa aggagatcca cactacaggg attattacgt atgggcgagt    360
gaaaaaacgg atctggacga agaagagag tgggacaacg aaaggatctg gcatcctctg     420
gaggacggaa ggttctacag aggactttttc ggtcccctct cacccgatct gaactacgat   480
aacccgcagg tttttgaaga gatgaagaag gtggtttatc accttcttga atgggagtg     540
gacggattca gattcgacgc agcaaagcac atgagagata ctctggaaca gaacgttcgc    600
ttttggaggt atttcctctc cgatattgag ggaatattcc ttgcggaaat ctgggcagaa    660
tccaaagttg tggatgaaca cggcaggata ttcggctaca tgctaaatttt cgatacctca   720
cactgtatta aggaagcggt gtggaaggaa aacttcaaag tgttgatcga gtcgatcgaa    780
agggccctgg ttggaaaaga ttatctgccg gtgaacttca catcgaacca tgatatgtca   840
aggcttgcga gttcgaagg agggttgagt gaagagaagg tgaaactctc actttccatt    900
ctgttcacgc ttcccggggt tcctctcata ttctacggag acgaactggg aatgaaagga   960
atctatcgaa aaccgaacac ggaagtcgtg ctggatccgt tcccctggag cgaaaacatg   1020
tgtgttgaag gccagacatt ttggaaatgg cccgcgtata acgatccatt ctccggtgtt   1080
tctgttgagt atcagaggag aaatcgtgat tcgattctct cacacacgat gaggtgggca   1140
ggattcagag gggaaaatca ctggctggac agggcaaaca tcgaatttct gtgcaaagaa   1200
gaaaactgc tcgtgtacag actggtcgat gaagggcgtt ctctgaaagt gatacacaac    1260
ctgtcgaatg gtgaaatggt gtttgaggga gtgcgcgtac aaccctacag cacggaggtg    1320
gtttga                                                              1326
```

<210> SEQ ID NO 69
<211> LENGTH: 34
<212> TYPE: DNA
<213> ORGANISM: Artificial Sequence
<220> FEATURE:
<223> OTHER INFORMATION: ??-glucan phosphorylase; Forward primer DNA
    sequence for amplifying ??-glucan phosphorylase gene from
    Thermotoga neapolitana

<400> SEQUENCE: 69

```
aggagaaact catatgctga agaaactccc ggag                                 34
```

<210> SEQ ID NO 70
<211> LENGTH: 21
<212> TYPE: DNA
<213> ORGANISM: Artificial Sequence
<220> FEATURE:
<223> OTHER INFORMATION: ??-glucan phosphorylase; Reverse primer DNA
    sequence for amplifying ??-glucan phosphorylase gene from
    Thermotoga neapolitana

<400> SEQUENCE: 70
agccccctcg agcccgagaa c                                        21

<210> SEQ ID NO 71
<211> LENGTH: 26
<212> TYPE: DNA
<213> ORGANISM: Artificial Sequence
<220> FEATURE:
<223> OTHER INFORMATION: Phosphoglucomutase; Forward primer DNA sequence
    for amplifying Phosphoglucomutase gene from Thermotoga neapolitana

<400> SEQUENCE: 71
aaagggcata tgatcctgtt tggaac                                   26

<210> SEQ ID NO 72
<211> LENGTH: 27
<212> TYPE: DNA
<213> ORGANISM: Artificial Sequence
<220> FEATURE:
<223> OTHER INFORMATION: Phosphoglucomutase; Reverse primer DNA sequence
    for amplifying Phosphoglucomutase gene from Thermotoga neapolitana

<400> SEQUENCE: 72
ataccagtct cgagcagttt caggatc                                  27

<210> SEQ ID NO 73
<211> LENGTH: 34
<212> TYPE: DNA
<213> ORGANISM: Artificial Sequence
<220> FEATURE:
<223> OTHER INFORMATION: glucose-6-phosphate-isomerase; Forward primer
    DNA sequence for amplifying glucose-6-phosphate-isomerase gene
    from Thermotoga neapolitana

<400> SEQUENCE: 73
ttactgaggg catatgaaaa agatggcttt gaaa                          34

<210> SEQ ID NO 74
<211> LENGTH: 30
<212> TYPE: DNA
<213> ORGANISM: Artificial Sequence
<220> FEATURE:
<223> OTHER INFORMATION: glucose-6-phosphate-isomerase; Reverse primer
    DNA sequence for amplifying glucose-6-phosphate-isomerase gene
    from Thermotoga neapolitana

<400> SEQUENCE: 74
aagacgcgtc gacttctatg atcaccttct                               30

<210> SEQ ID NO 75
<211> LENGTH: 34
<212> TYPE: DNA
<213> ORGANISM: Artificial Sequence
<220> FEATURE:
<223> OTHER INFORMATION: fructose-6-phosphate-isomerase; Forward primer
    DNA sequence for amplifying fructose-6-phosphate-isomerase gene
    from Thermotoga neapolitana -continued

<400> SEQUENCE: 75
ggaacatatg atggtaaaga tcgccgcttc aatc                                34

<210> SEQ ID NO 76
<211> LENGTH: 27
<212> TYPE: DNA
<213> ORGANISM: Artificial Sequence
<220> FEATURE:
<223> OTHER INFORMATION: fructose-6-phosphate-isomerase; Reverse primer
      DNA sequence for amplifying fructose-6-phosphate-isomerase gene
      from Thermotoga neapolitana

<400> SEQUENCE: 76
catactcgag cttcccctct cctatct                                        27

<210> SEQ ID NO 77
<211> LENGTH: 270
<212> TYPE: PRT
<213> ORGANISM: Artificial Sequence
<220> FEATURE:
<223> OTHER INFORMATION: Polyphospate-dependent glucokinase; Amino acid
      sequence of Polyphospate-dependent glucokinase derived from
      Deinococcus geothermalis

<400> SEQUENCE: 77

Met Leu Ala Ala Ser Asp Ser Ser Gln His Gly Gly Lys Ala Val Thr
1               5                   10                  15

Leu Ser Pro Met Ser Val Ile Leu Gly Ile Asp Ile Gly Gly Ser Gly
            20                  25                  30

Ile Lys Gly Ala Pro Val Asp Thr Ala Thr Gly Lys Leu Val Ala Glu
        35                  40                  45

Arg His Arg Ile Pro Thr Pro Glu Gly Ala His Pro Asp Ala Val Lys
    50                  55                  60

Asp Val Val Val Glu Leu Val Arg His Phe Gly His Ala Gly Pro Val
65                  70                  75                  80

Gly Ile Thr Phe Pro Gly Ile Val Gln His Gly His Thr Leu Ser Ala
                85                  90                  95

Ala Asn Val Asp Lys Ala Trp Ile Gly Leu Asp Ala Asp Thr Leu Phe
            100                 105                 110

Thr Glu Ala Thr Gly Arg Asp Val Thr Val Ile Asn Asp Ala Asp Ala
        115                 120                 125

Ala Gly Leu Ala Glu Ala Arg Phe Gly Ala Gly Ala Gly Val Pro Gly
    130                 135                 140

Glu Val Leu Leu Leu Thr Phe Gly Thr Gly Ile Gly Ser Ala Leu Ile
145                 150                 155                 160

Tyr Asn Gly Val Leu Val Pro Asn Thr Glu Phe Gly His Leu Tyr Leu
                165                 170                 175

Lys Gly Asp Lys His Ala Glu Thr Trp Ala Ser Asp Arg Ala Arg Glu
            180                 185                 190

Gln Gly Asp Leu Asn Trp Lys Gln Trp Ala Lys Arg Val Ser Arg Tyr
        195                 200                 205

Leu Gln Tyr Leu Glu Gly Leu Phe Ser Pro Asp Leu Phe Ile Ile Gly
    210                 215                 220

Gly Gly Val Ser Lys Lys Ala Asp Lys Trp Gln Pro His Val Ala Thr
225                 230                 235                 240

Thr Arg Thr Arg Leu Val Pro Ala Ala Leu Gln Asn Glu Ala Gly Ile
                245                 250                 255

Val Gly Ala Ala Met Val Ala Ala Gln Arg Ser Gln Gly Asp

<210> SEQ ID NO 78
<211> LENGTH: 253
<212> TYPE: PRT
<213> ORGANISM: Artificial Sequence
<220> FEATURE:
<223> OTHER INFORMATION: Polyphospate-dependent glucokinase; Amino acid
      sequence of Polyphospate-dependent glucokinase derived from
      Anaerolinea thermophila

<400> SEQUENCE: 78

```
Met Gly Arg Gln Gly Met Glu Ile Leu Gly Ile Asp Ile Gly Gly Ser
1               5                   10                  15

Gly Ile Lys Gly Ala Pro Val Asp Val Glu Thr Gly Gln Leu Thr Ala
            20                  25                  30

Glu Arg Tyr Arg Leu Pro Thr Pro Glu Asn Ala Leu Pro Glu Glu Val
        35                  40                  45

Ala Leu Val Val Ala Gln Ile Val Glu His Phe Gln Trp Lys Gly Arg
    50                  55                  60

Val Gly Ala Gly Phe Pro Ala Ala Ile Lys His Gly Val Ala Gln Thr
65                  70                  75                  80

Ala Ala Asn Ile His Pro Thr Trp Ile Gly Leu His Ala Gly Asn Leu
                85                  90                  95

Phe Ser Glu Lys Cys Gly Cys Pro Val Ser Val Leu Asn Asp Ala Asp
            100                 105                 110

Ala Ala Gly Leu Ala Glu Met Ile Phe Gly Ala Gly Lys Gly Gln Lys
        115                 120                 125

Gly Val Val Leu Met Ile Thr Ile Gly Thr Gly Ile Gly Thr Ala Leu
    130                 135                 140

Phe Thr Asp Gly Ile Leu Val Pro Asn Thr Glu Leu Gly His Ile Glu
145                 150                 155                 160

Ile Arg Gly Lys Asp Ala Glu Gln Arg Ser Ser Glu Ala Ala Arg Gln
                165                 170                 175

Arg Lys Asp Trp Thr Trp Gln Gln Trp Ala Lys Arg Leu Asn Glu His
            180                 185                 190

Leu Glu Arg Leu Glu Ala Leu Phe Trp Pro Asp Leu Phe Ile Leu Gly
        195                 200                 205

Gly Gly Ala Val Lys Asn His Glu Lys Phe Phe Pro Tyr Leu Lys Leu
    210                 215                 220

Arg Thr Pro Phe Val Ala Ala Lys Leu Gly Asn Leu Ala Gly Ile Val
225                 230                 235                 240

Gly Ala Ala Trp Tyr Ala His Thr Gln Glu Thr Gln Ala
                245                 250
```

<210> SEQ ID NO 79
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 79

```
Trp Ile Ile Asp Pro Ile Asp Gly Thr
1               5
```

<210> SEQ ID NO 80
<211> LENGTH: 9
<212> TYPE: PRT

```
<213> ORGANISM: Artificial Sequence
<220> FEATURE:
<223> OTHER INFORMATION: Synthetic Sequence

<400> SEQUENCE: 80

Trp Ile Val Asp Pro Leu Asp Gly Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 81

Phe Val Leu Asp Pro Leu Asp Gly Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 82

Trp Ile Ile Asp Pro Leu Asp Gly Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 83

Phe Ile Val Asp Pro Leu Asp Gly Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 84

Ile Val Val Asp Pro Ile Asp Gly Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 85

Trp Val Ile Asp Pro Ile Asp Gly Thr
1               5

<210> SEQ ID NO 86
<211> LENGTH: 9
<212> TYPE: PRT
<213> ORGANISM: Artificial Sequence
```

```
<220> FEATURE:
<223> OTHER INFORMATION: Synthetic Sequence

<400> SEQUENCE: 86

Trp Phe Ile Asp Pro Ile Asp Gly Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 87

Ala Ile Val Asp Pro Leu Asp Gly Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 88

Ile Phe Ile Asp Pro Ile Asp Gly Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 89

Val Ile Val Asp Pro Leu Asp Gly Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 90

Val Ala Leu Asp Pro Leu Asp Gly Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 91

Trp Ile Val Asp Pro Ile Asp Gly Thr
1               5

<210> SEQ ID NO 92
<211> LENGTH: 15
<212> TYPE: PRT
<213> ORGANISM: Artificial Sequence
<220> FEATURE:
```

<223> OTHER INFORMATION: Synthetic Sequence

<400> SEQUENCE: 92

Trp Asp Val Ala Ala Gly Ile Leu Leu Val Glu Glu Gly Gly Gly
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 93

Trp Asp Val Ala Pro Leu Phe Val Leu Val Pro Glu Ala Gly Gly
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 94

Trp Asp Val Ala Ala Gly Trp Leu Ile Val Ser Glu Ala Gly Gly
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 95

Trp Asp Ile Ser Ala Gly Ile Leu Ile Val Glu Glu Ala Lys Gly
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 96

Leu Asp Val Ala Gly Ala Leu Thr Ile Gly Lys Tyr Val Asp Gly
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 97

Trp Asp Val Ala Ala Gly Ile Val Ile Leu Arg Glu Ala Gly Gly
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 98

Trp Asp Val Ala Ala Gly Trp Leu Leu Val Glu Glu Ala Gly Gly
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 99

Thr Asp Ile Ala Ala Gly Tyr Ile Ile Ala Lys Glu Ala Gly Ala
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 100

Trp Asp Phe Ala Gly Gly Met Ile Leu Ile Glu Glu Ala Gly Gly
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 101

Trp Asp Cys Ala Pro Phe Pro Pro Ile Phe Arg Glu Ala Gly Gly
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 102

Val Asp Ile Ala Ala Ser Ser Asn Phe Cys Ser Arg Leu Gly Val
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 103

Trp Asp Val Ala Pro Gly Ile Leu Leu Val Glu Glu Ala Gly Gly
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic Sequence

```
<400> SEQUENCE: 104

Thr Asp Ile Ala Ala Gly Thr Ile Ile Ala Lys Glu Ala Gly Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 105

Tyr Asp Ala Ala Ala Gly Val Phe Ile Ala Glu Lys Ala Gly Gly
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 106

Trp Asp Ile Ala Ala Gly Val Ala Leu Val Leu Ala Ala Gly Gly
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 107

Trp Asp Val Ala Ala Gly Trp Leu Leu Ile Thr Glu Ala Gly Gly
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 108

Trp Asp Val Ala Ala Gly Trp Leu Ile Ile Arg Glu Ala Gly Gly
1               5                   10                  15
```